(12) United States Patent
Kiani et al.

(10) Patent No.: US 9,364,657 B2
(45) Date of Patent: Jun. 14, 2016

(54) CUFF UNIT FOR A FUNCTIONAL ELECTRICAL STIMULATION SYSTEM

(71) Applicant: Ensilver Canada, Markham OT (CA)

(72) Inventors: Farsad Kiani, Richmond Hill (CA); Jinbiao Zheng, Scarborough (CA)

(73) Assignee: Ensilver Canada, Markham (CA)

( * ) Notice: Subject to any disclaimer, the term of this patent is extended or adjusted under 35 U.S.C. 154(b) by 0 days.

(21) Appl. No.: 14/529,854

(22) Filed: Oct. 31, 2014

(65) Prior Publication Data

US 2016/0121099 A1    May 5, 2016

(51) Int. Cl.
A61N 1/00    (2006.01)
*A61N 1/04*    (2006.01)
*A61N 1/36*    (2006.01)

(52) U.S. Cl.
CPC .......... *A61N 1/0472* (2013.01); *A61N 1/36003* (2013.01); *A61N 1/36014* (2013.01)

(58) Field of Classification Search
CPC . A61N 1/0452; A61N 1/0472; A61N 1/0456; A61N 1/0484; A61N 1/321; A61N 1/36014; A61N 1/36003
See application file for complete search history.

(56) References Cited

U.S. PATENT DOCUMENTS

| | | | |
|---|---|---|---|
| 5,014,705 A | 5/1991 | Graupe et al. | |
| 5,016,635 A | 5/1991 | Graupe | |
| 5,070,873 A | 12/1991 | Graupe et al. | |
| 5,092,329 A | 3/1992 | Graupe et al. | |
| 6,324,432 B1 | 11/2001 | Rigaux et al. | |
| 6,456,884 B1 | 9/2002 | Kenney | |
| 7,147,667 B2 | 12/2006 | Bedard | |
| 7,632,239 B2 | 12/2009 | Dar et al. | |
| 7,660,636 B2 | 2/2010 | Castel et al. | |
| 7,867,284 B2 | 1/2011 | Bedard | |
| 7,899,556 B2 | 3/2011 | Nathan et al. | |
| 7,949,403 B2 | 5/2011 | Palermo et al. | |
| 8,057,486 B2 | 11/2011 | Hansen | |
| 8,082,035 B2 | 12/2011 | Glukhovsky | |

(Continued)

FOREIGN PATENT DOCUMENTS

CA    2074532 A1    5/1992
CA    2794533 A1    5/2007

(Continued)

OTHER PUBLICATIONS

Bioness Inc., "Bioness LiveOn NESS H200 Wireless: User's Guide", 2011.

(Continued)

*Primary Examiner* — Scott Getzow
(74) *Attorney, Agent, or Firm* — Bereskin & Parr LLP/S.E.N.C.R.L., s.r.l.

(57) ABSTRACT

Various embodiments are described herein for a cuff unit that may be used with a Functional Electrical Stimulation (FES) orthotic system. One example embodiment includes a flexible housing that is releasably mountable on a user including a frame and a plurality of panels entirely contained within the frame. A battery module having one or more batteries is contained within a one or more of the panels. A stimulation module is coupled to the battery module and contained in one or more of the panels is operable to generate stimulation signals to be applied to the user. At least two contact members that are coupled to the frame and in electrical communication with the stimulation module are operable to apply the stimulation signals to the user.

25 Claims, 33 Drawing Sheets

(56) References Cited

U.S. PATENT DOCUMENTS

| | | | |
|---|---|---|---|
| D658,769 S | 5/2012 | Moser et al. | |
| 8,167,640 B2 | 5/2012 | Ochoa et al. | |
| 8,175,713 B1 | 5/2012 | Cywinski | |
| 8,209,022 B2 | 6/2012 | Dar et al. | |
| 8,209,036 B2 | 6/2012 | Nathan et al. | |
| 8,332,029 B2 | 12/2012 | Glukhovsky et al. | |
| 8,364,277 B2 | 1/2013 | Glukhovsky | |
| 8,382,688 B2 | 2/2013 | Dar et al. | |
| 8,463,390 B2 | 6/2013 | Muraoka | |
| 2003/0125781 A1 | 7/2003 | Dohno et al. | |
| 2003/0195586 A1 | 10/2003 | Rigaux et al. | |
| 2003/0195587 A1 | 10/2003 | Rigaux et al. | |
| 2004/0122483 A1 | 6/2004 | Nathan et al. | |
| 2005/0261609 A1 | 11/2005 | Collings et al. | |
| 2009/0030344 A1 | 1/2009 | Moser et al. | |
| 2009/0240313 A1 | 9/2009 | Buhlmann et al. | |
| 2010/0042180 A1 | 2/2010 | Mueller et al. | |
| 2010/0191316 A1 | 7/2010 | Buhlmann et al. | |
| 2011/0093035 A1 | 4/2011 | Moser et al. | |
| 2011/0125290 A1 | 5/2011 | Langlois | |
| 2011/0137429 A1 | 6/2011 | Bedard | |
| 2011/0152968 A1 | 6/2011 | Nathan et al. | |
| 2011/0282412 A1 | 11/2011 | Glukhovsky et al. | |
| 2012/0059298 A1* | 3/2012 | Hoffman | A61F 5/013 602/21 |
| 2012/0116478 A1 | 5/2012 | Bulhlmann et al. | |
| 2012/0203156 A1* | 8/2012 | Dar | A61F 5/01 602/16 |
| 2012/0239112 A1 | 9/2012 | Muraoka | |
| 2012/0330375 A1 | 12/2012 | Nathan et al. | |
| 2012/0330394 A1 | 12/2012 | Dar et al. | |
| 2012/0330395 A1 | 12/2012 | Dar et al. | |
| 2013/0013041 A1 | 1/2013 | Glukhovsky et al. | |
| 2014/0259799 A1 | 9/2014 | McDonnell et al. | |
| 2015/0100104 A1 | 4/2015 | Kiani et al. | |
| 2015/0100105 A1 | 4/2015 | Kiani et al. | |
| 2015/0100107 A1 | 4/2015 | Kiani et al. | |

FOREIGN PATENT DOCUMENTS

| | | |
|---|---|---|
| CA | 2649663 A1 | 11/2007 |
| CA | 2663030 A1 | 4/2008 |
| CA | 2697381 A1 | 2/2009 |
| CA | 2727812 A1 | 12/2009 |
| CA | 2732751 A1 | 2/2010 |
| CA | 2780328 A1 | 6/2011 |
| CA | 2782677 A1 | 6/2011 |
| CN | 202078650 U | 12/2011 |
| DE | 60 2004 005 692 T2 | 12/2007 |
| EP | 1201266 A1 | 5/2002 |
| EP | 1435891 A4 | 4/2003 |
| EP | 1530493 A1 | 3/2004 |
| EP | 1819395 A2 | 6/2006 |
| EP | 1874398 A4 | 10/2006 |
| EP | 1874404 A2 | 10/2006 |
| EP | 2037804 A2 | 12/2007 |
| EP | 1095670 B1 | 5/2008 |
| EP | 2120801 A1 | 7/2008 |
| EP | 1531767 B1 | 10/2008 |
| EP | 1980224 A2 | 10/2008 |
| EP | 2152359 A2 | 12/2008 |
| EP | 2180918 A2 | 2/2009 |
| EP | 2194862 A1 | 3/2009 |
| EP | 2247249 A1 | 8/2009 |
| EP | 2252242 A1 | 8/2009 |
| EP | 2291220 A1 | 12/2009 |
| EP | 2320993 A1 | 2/2010 |
| EP | 2506918 A1 | 6/2011 |
| EP | 2506919 A1 | 6/2011 |
| EP | 2392381 A2 | 12/2011 |
| EP | 1531766 B1 | 1/2012 |
| EP | 2097851 B1 | 2/2012 |
| EP | 2012669 B1 | 3/2013 |
| EP | 2586489 A1 | 5/2013 |
| JP | 201275933 A | 4/2012 |
| KR | 10-2005-0042793 A | 5/2005 |
| KR | 10-2005-0058417 A | 6/2005 |
| KR | 10-2006-0100427 A | 9/2006 |
| KR | 10-2009-0025184 A | 3/2009 |
| WO | 9209328 A1 | 6/1992 |
| WO | 2005-122740 A3 | 12/2005 |
| WO | 2006-061804 A8 | 6/2006 |
| WO | 2006-113802 A2 | 10/2006 |
| WO | 2007-125534 A2 | 11/2007 |
| WO | 2008-043065 A2 | 4/2008 |
| WO | 2008-086629 A1 | 7/2008 |
| WO | 2009-021157 A1 | 2/2009 |
| WO | 2009-026588 A2 | 2/2009 |
| WO | 2009-038861 A1 | 3/2009 |
| WO | 2009-052134 A1 | 4/2009 |
| WO | 2009-052135 A1 | 4/2009 |
| WO | 2009-088563 A1 | 7/2009 |
| WO | 2009-137234 A2 | 11/2009 |
| WO | 2009-155436 A1 | 12/2009 |
| WO | 2009-158389 A1 | 12/2009 |
| WO | 2010-002517 A1 | 1/2010 |
| WO | 2010-017004 A1 | 2/2010 |
| WO | 2010-107648 A1 | 9/2010 |
| WO | 2011-068823 A1 | 6/2011 |
| WO | 2011-068849 A1 | 6/2011 |
| WO | 2013-001526 A2 | 6/2012 |
| WO | 2012-107921 A1 | 8/2012 |
| WO | 2012-150500 A1 | 11/2012 |

OTHER PUBLICATIONS

Bioness Inc., "Bioness LiveOn NESS L300Plus: User's Guide", 2011.

Bioness Inc., "Bioness LiveOn NESS L300: Clinician's Guide", 2010.

Innovative Neurotronics, "WalkAide System: User Manual", 2010.

* cited by examiner

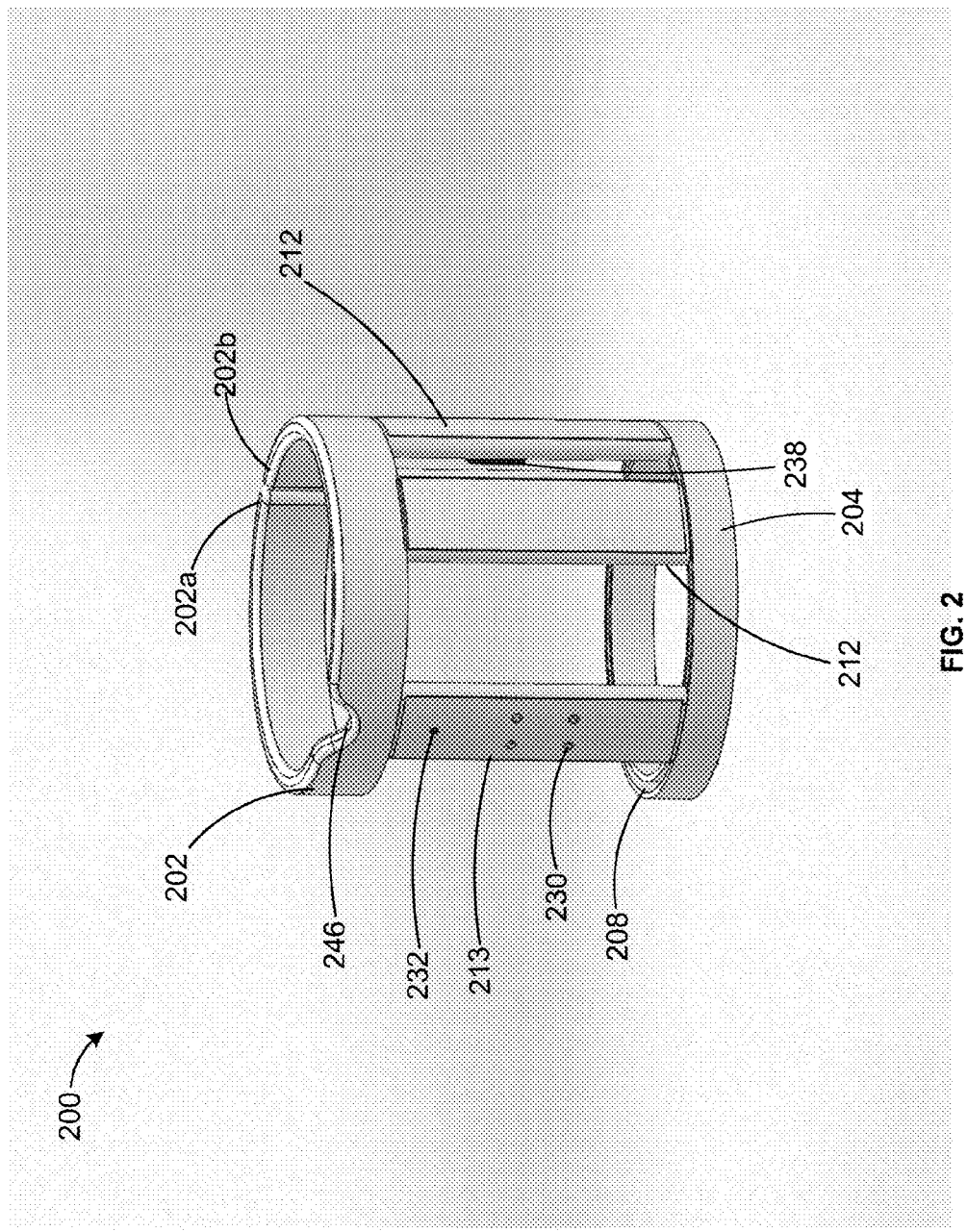

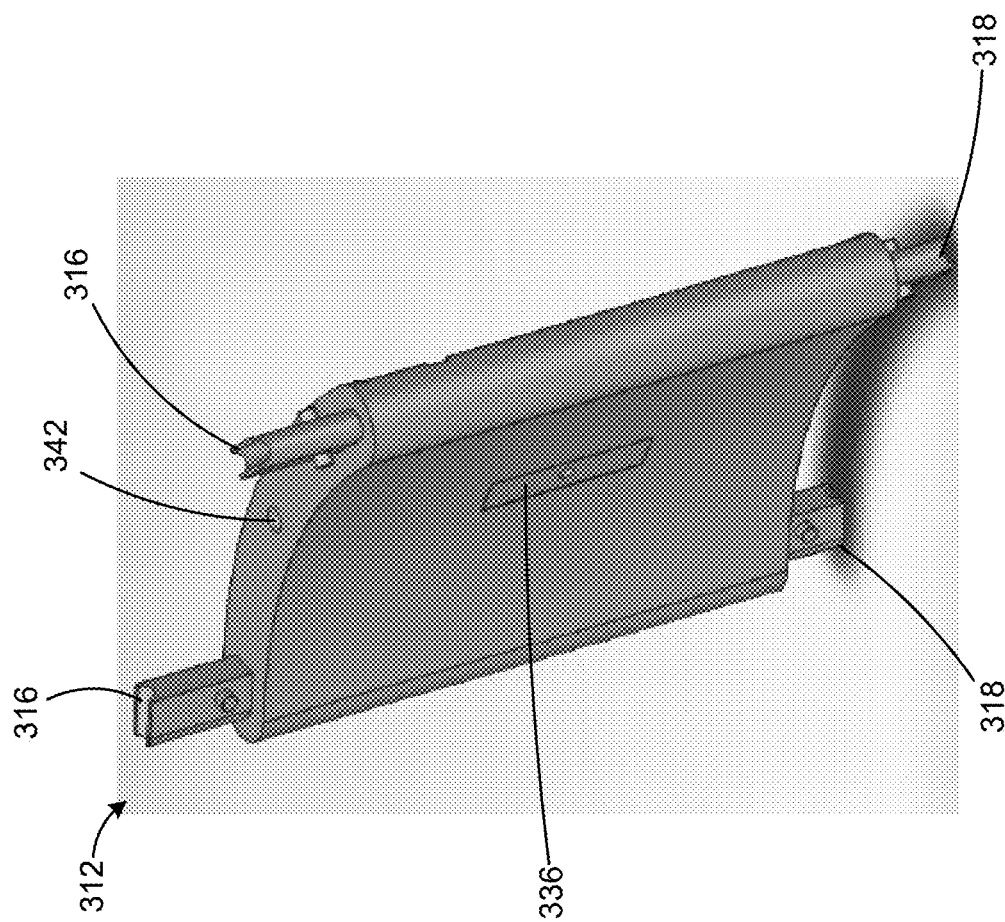

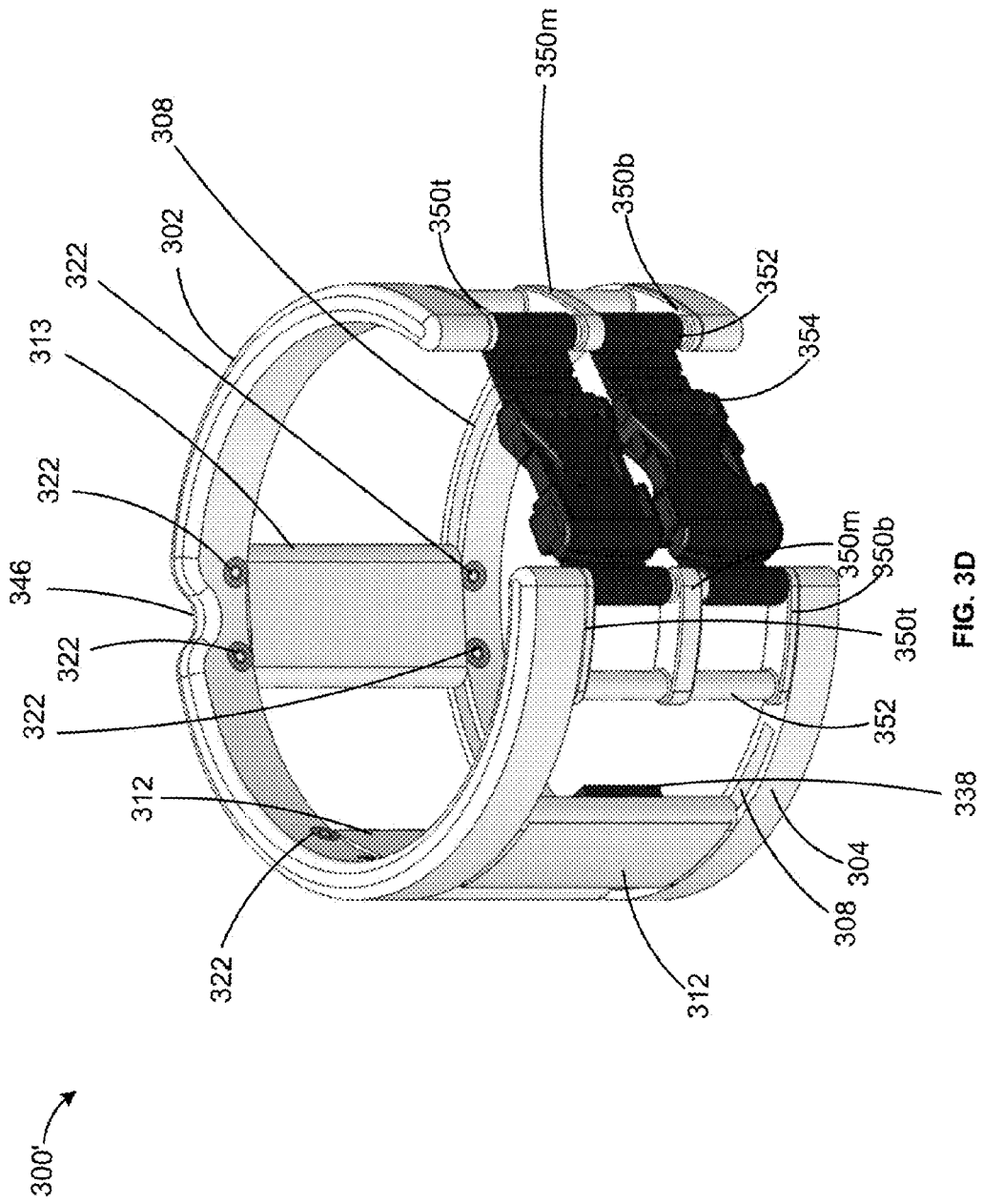

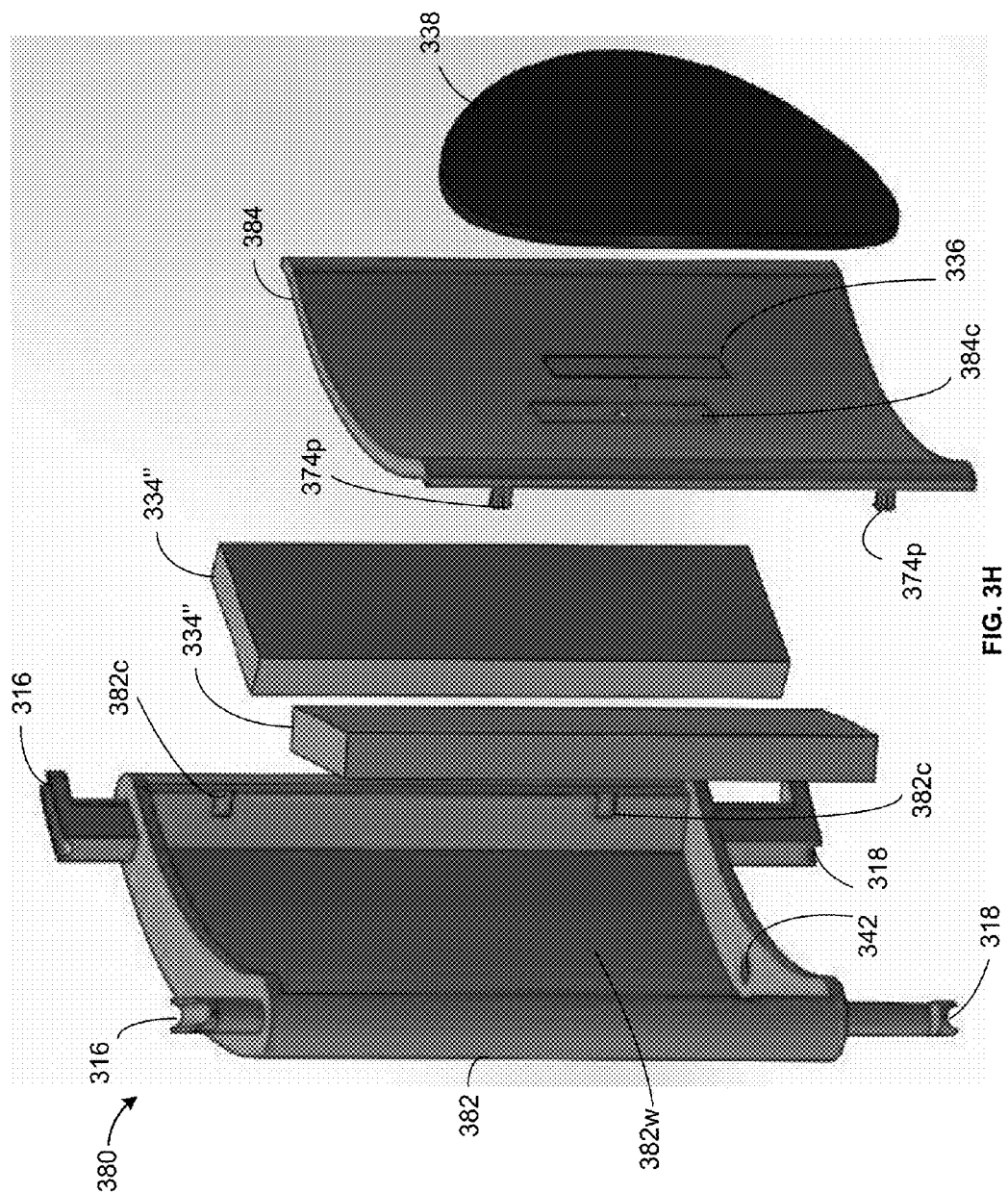

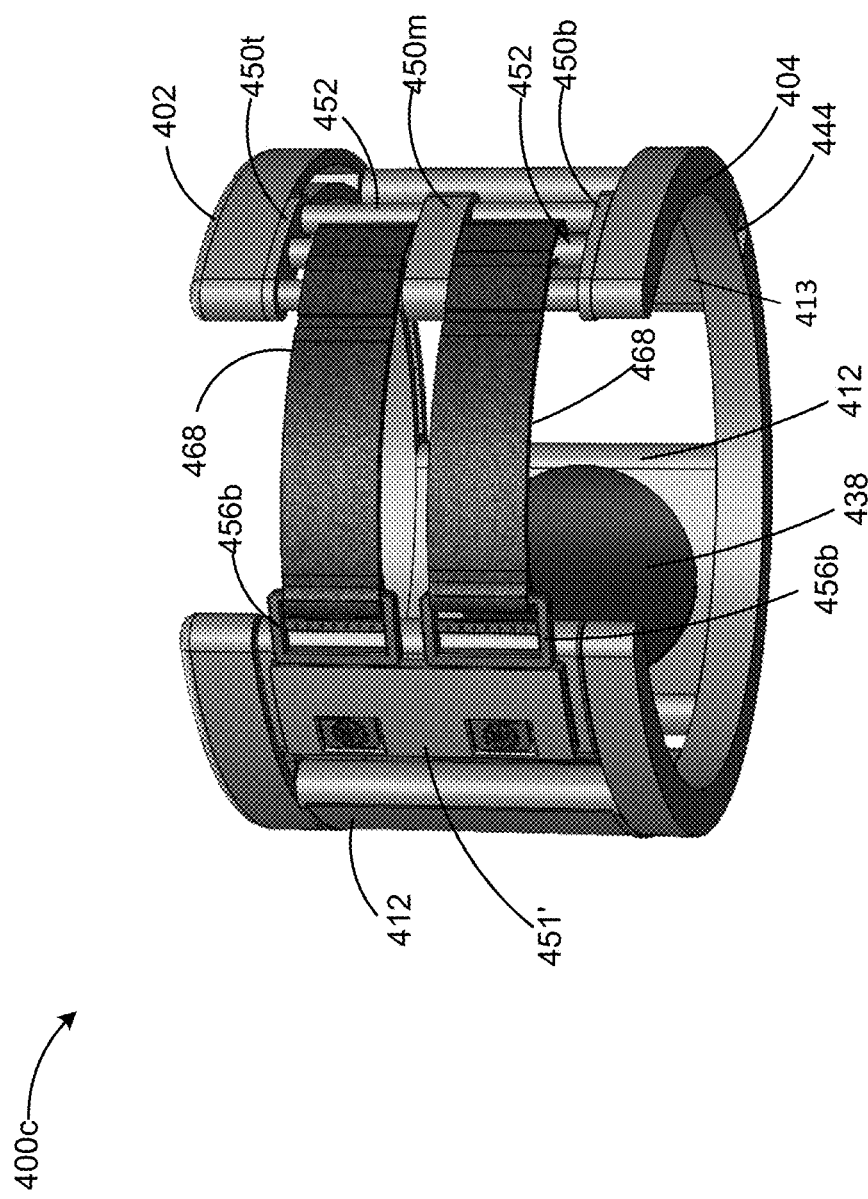

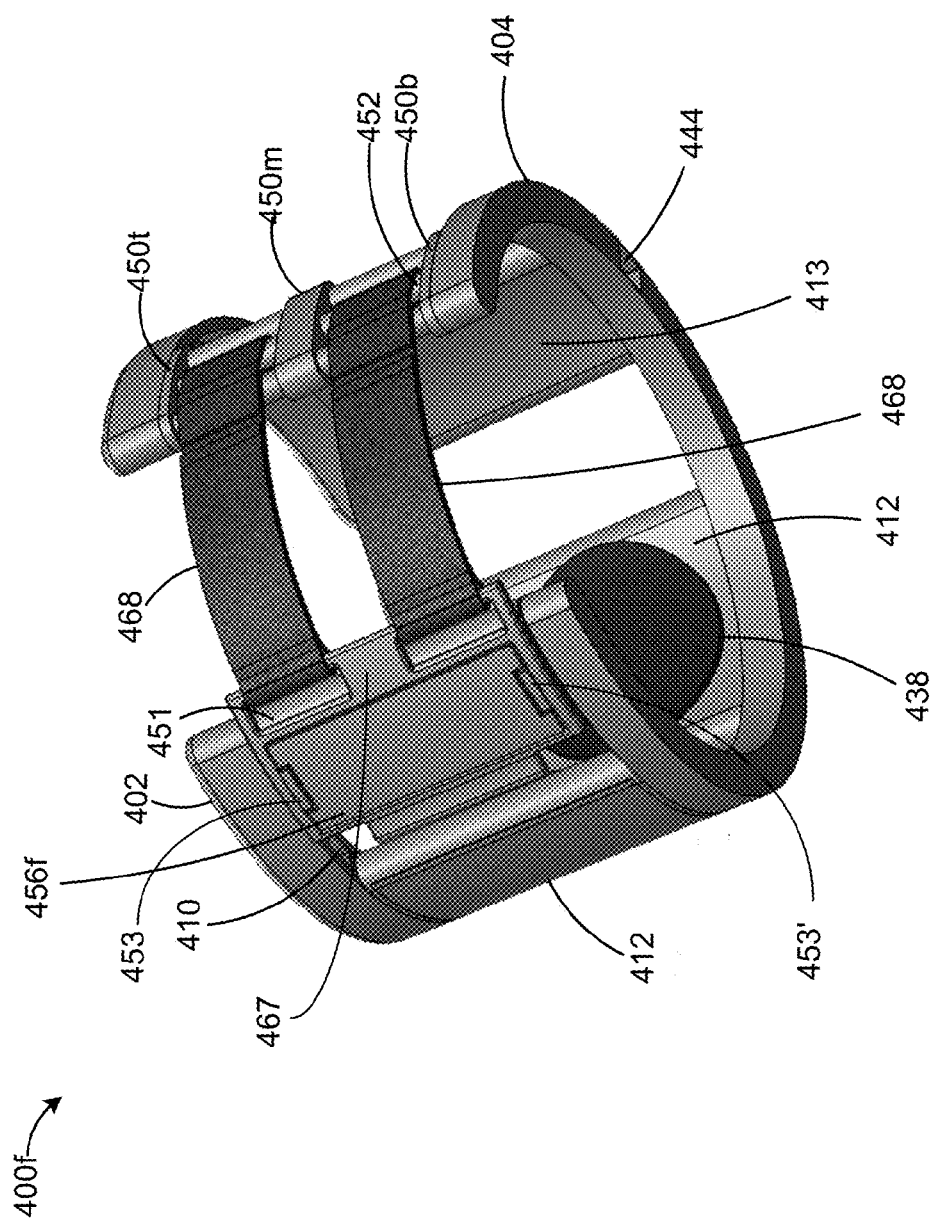

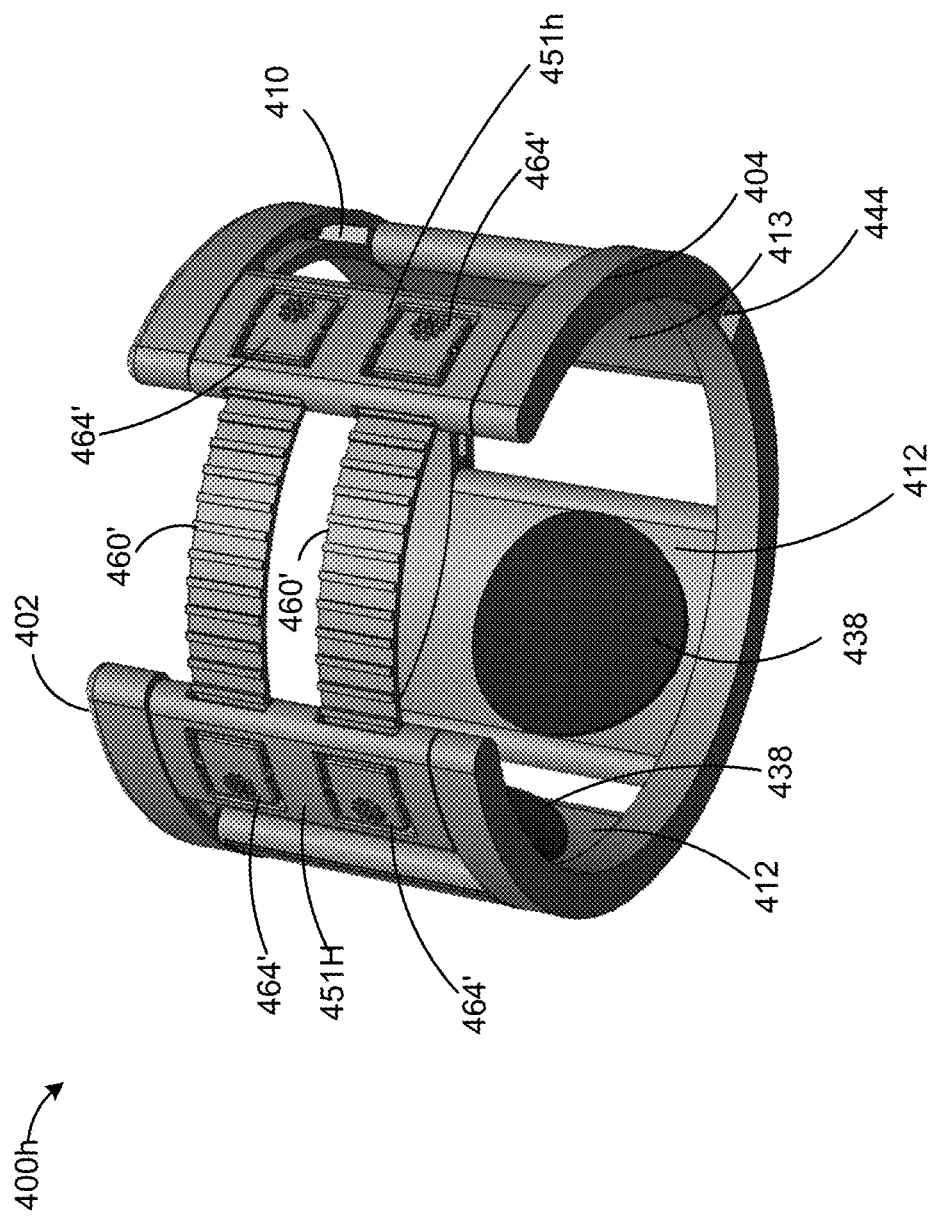

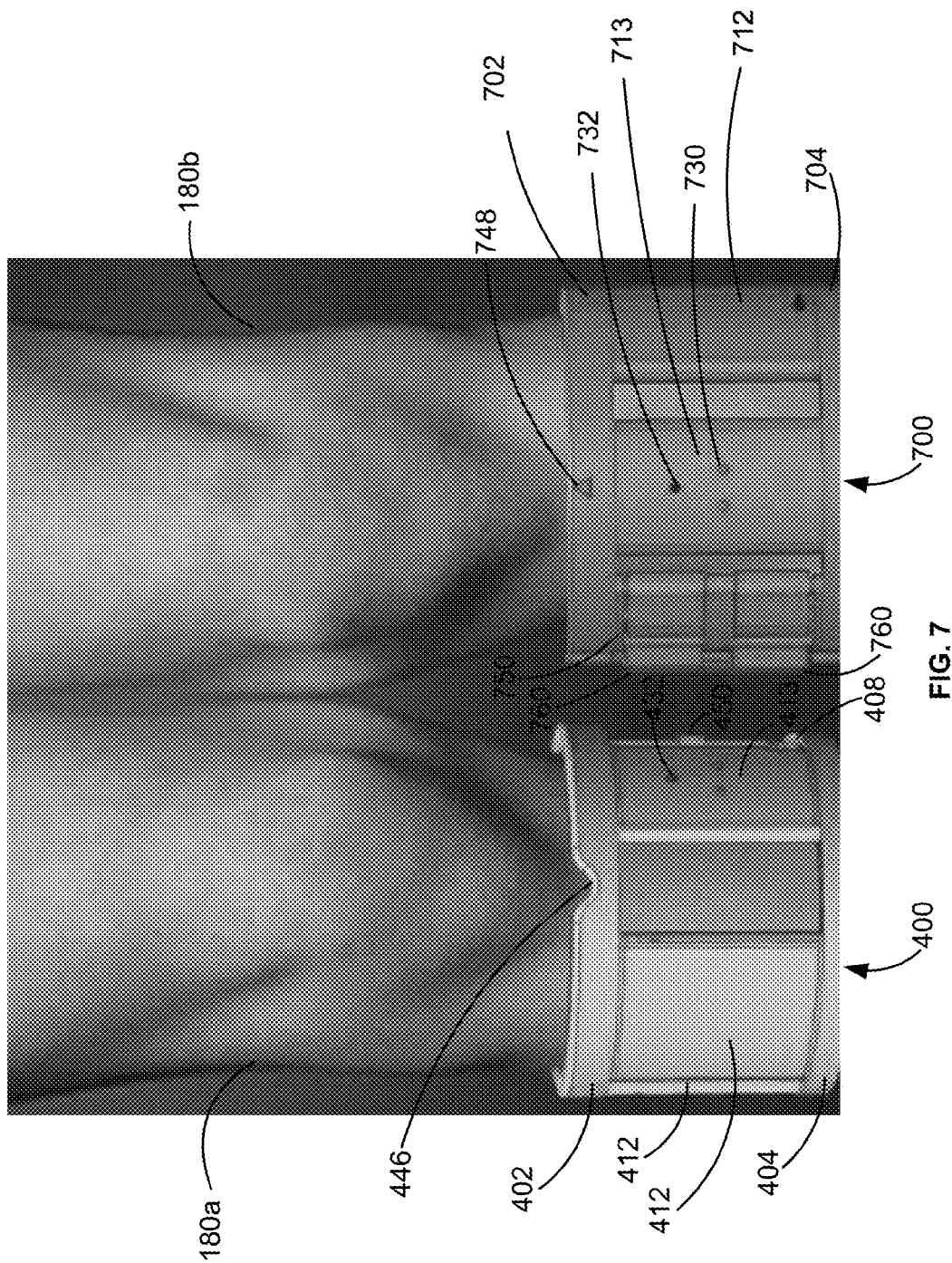

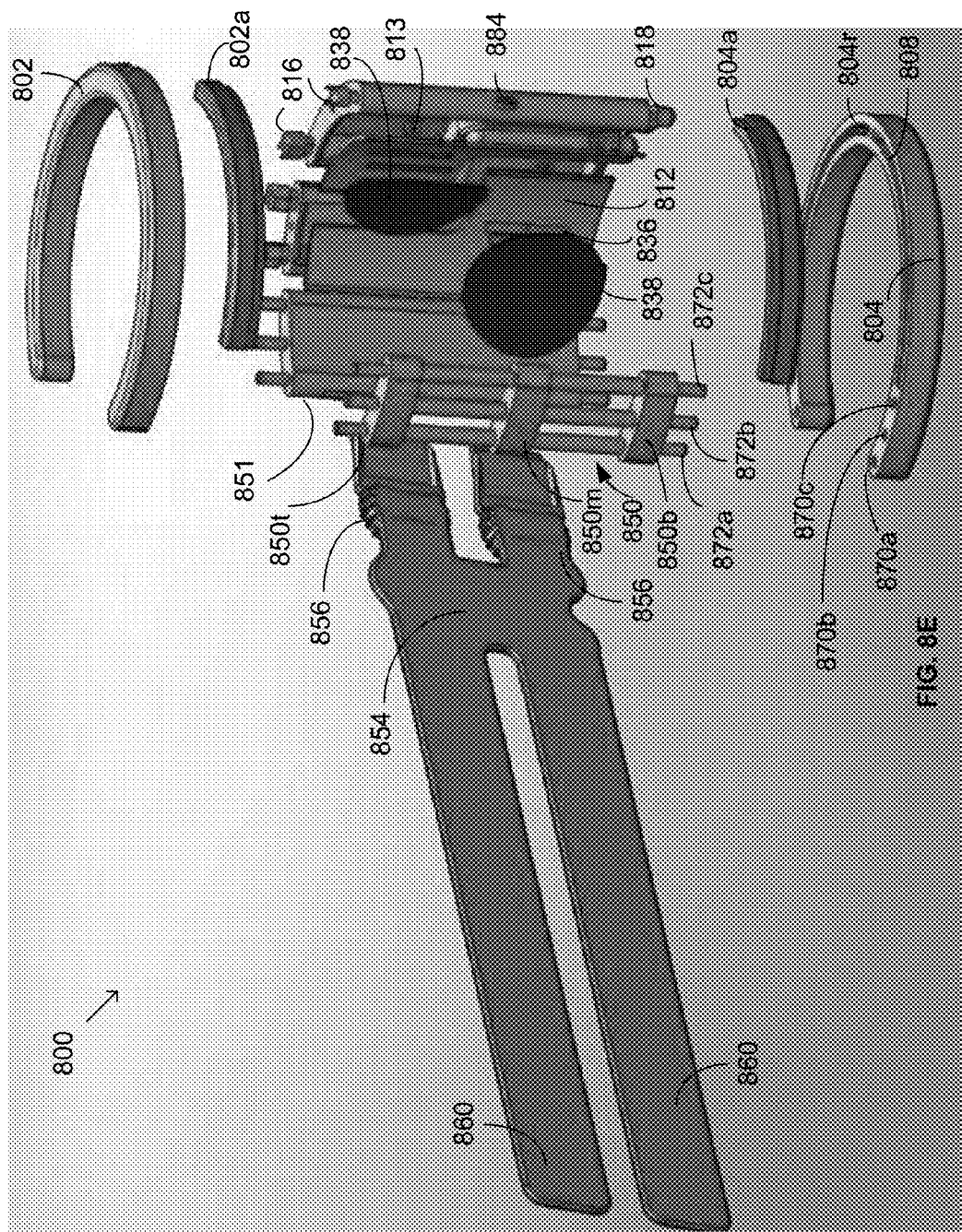

CUFF UNIT FOR A FUNCTIONAL ELECTRICAL STIMULATION SYSTEM

FIELD

The various embodiments described herein relate to an apparatus for a Functional Electrical Stimulation (FES) orthotic system, and more particularly are related to a cuff unit that may be used to apply stimulation signals to a user.

INTRODUCTION

Individuals suffering from a central nervous system injury, such as a stroke, a brain injury, multiple sclerosis, cerebral palsy or partial spinal cord injuries, or other medical conditions may have mobility problems due to that injury or medical condition. Functional electrical stimulation (FES) systems may assist those individuals in addressing those mobility problems.

Existing FES systems provide electrical stimulation to muscles that may have been paralyzed or otherwise affected due to the central nervous system injury or other medical condition. The electrical stimulation may facilitate motion in those affected muscles. In some cases, FES systems may also help reeducate muscle movement, retard atrophy of any affected muscles due to disuse, and maintain or increase a range of motion at nearby joints.

An example application of an FES system is to enhance ankle dorsiflexion for individuals experiencing foot drop. Foot drop is a gait abnormality that stems from a weakness in a foot, damage to a peroneal nerve, or paralysis of muscles in an anterior portion of a lower leg. Foot drop may be caused by various conditions, such as muscle or spinal nerve trauma, abnormal anatomy, toxins and disease. Individuals affected by foot drop are unable to properly lift their foot and toes during a swing phase of their gait thereby causing their toes to be caught by the ground and their foot to drag on the ground. The FES system can assist those individuals by sending electrical stimulation signals to the affected muscles during the swing phase of their gait in order to trigger movement in those muscles so that the foot is lifted and not dragged along the ground.

Although existing FES systems are generally portable, they tend to be bulky and cumbersome for users to carry around on a daily basis. Existing FES systems also tend to lack versatility in operation and offer limited functionality.

SUMMARY

In a broad aspect, at least one embodiment described herein provides an apparatus for a functional electrical stimulation (FES) system. The apparatus may comprise a flexible housing comprising a frame having a plurality of panels entirely contained within the housing, the housing being releasably mountable on a user; a battery module having one or more batteries, each battery module being contained within a first one or more of the panels; a stimulation module coupled to the battery module and contained within a second one or more of the panels, the stimulation module being operable to generate stimulation signals to be applied to the user; control circuitry disposed within the flexible housing and coupled to the battery module and the stimulation module to control the apparatus; and at least two contact members movably connected to the frame and in electrical contact with the stimulation module, the at least two contact members being operable to apply the stimulation signals to the user.

In at least some embodiments, each contact member may be associated with one of the panels and each contact member may comprise a conductive member disposed along a surface of the associated panel; and an electrode coupled to the conductive strip and mounted to the associated panel.

In at least some embodiments, the electrode may be translatable with respect to the panel to which it is mounted.

In at least some embodiments, the frame may comprise a set of horizontally extending peripheral members.

In at least some embodiments, the set of horizontally extending peripheral members may comprise: a first peripheral member defining an upper periphery of the frame; and a second peripheral member substantially parallel to and spaced apart from the first peripheral member, the second peripheral member defining a lower periphery of the frame; wherein each of the first and second peripheral members has a peripheral member width dimension defining a frame width for the frame.

In at least some embodiments, each panel may have a panel width and the frame width is at least equal to the panel width.

In at least some embodiments, each panel may extend in a substantially vertical direction between the first and second peripheral members.

In at least some embodiments, the panels may be movable with respect to the frame.

In at least some embodiments, at least some of the panels may be re-adjustably movable with respect to the frame.

In at least some embodiments, the panels that are re-adjustably movable may be initially movable with respect to the frame and subsequently fixed in place for later use by the user.

In at least some embodiments, the frame may comprise a track defined by an upper track portion provided on an edge of the first peripheral member and a lower track portion provided on a corresponding edge of the second peripheral member; and a first end of each panel is engageable with the upper track portion of the first peripheral member and a second end of each panel is engageable with the second track portion of the second peripheral member, the second end being opposite to the first end.

In at least some embodiments, the panels may be translatable along the track and the first and second end portions of the panels include connectors that engage connector portions in the upper and lower track portions respectively.

In at least some embodiments, the housing may further comprise a third peripheral member substantially parallel to the first peripheral member between the first and second peripheral members; a first set of panels of the plurality of panels positioned between the first peripheral member and the third peripheral member; and a second set of panels of the plurality of panels positioned between the second peripheral member and the third peripheral member.

In at least some embodiments, each panel in the second set of panels may extend in a substantially vertical direction between the second and third peripheral members.

In at least some embodiments, the frame may comprise a track defined by an upper track portion provided on an edge of the third peripheral member and a lower track portion provided on a corresponding edge of the second peripheral member; and a first end of each panel in the second set of panels is engageable with the upper track portion of the third peripheral member and a second end of each panel in the second set of panels is engageable with the lower track portion of the second peripheral member, the second end being opposite to the first end.

In at least some embodiments, each panel in the second set of panels may be translatable along the track.

In at least some embodiments, each contact member may be associated with one of the panels in the second set of panels.

In at least some embodiments, the batteries may be contained in one or more of the panels in the first set of panels.

In at least some embodiments, the panels may have a complementary shape to engage one another in an interlocking fashion.

In such embodiments, the panels may comprise an L shape.

In such embodiments, the panels may be arranged such that a first panel is flipped vertically and flipped horizontally to face a second panel.

In such embodiments, adjacent panels may have an L shape and an L-shape rotated 180 degrees.

In at least some embodiments, the panels may be spaced apart along the frame and air gaps are provided between the panels.

In at least some embodiments, a given panel may comprise at least one battery and a circuit board to provide the stimulation module.

Alternatively, in at least some embodiments, a given panel may comprise at least one circuit board to provide the stimulation module and the control circuitry.

In at least some embodiments, the given panel may further comprise a given electrode.

In at least some embodiments, one of the panels may be a control panel comprising control circuitry and control buttons to allow a user to control the apparatus.

In at least some embodiments, the control panel may further comprise an indicator light for providing a visual indication of a status of the apparatus. In at least some embodiments, there may be at least one indicator light that outputs a colored light during use.

In at least some embodiments, the frame may be releasably securable around a leg of the user.

In at least some embodiments, the apparatus may comprise fasteners for releasably securably mounting the frame on the leg of the user.

In at least some embodiments, the control circuitry may comprise a wireless communication module.

In at least some embodiments, the apparatus may further comprise a USB connector port coupled to at least one of the battery module and the stimulation module.

In another broad aspect, at least one embodiment described herein provides an apparatus for a functional electrical stimulation (FES) system. The apparatus may comprise a flexible housing comprising a frame that is releasably mountable on a user, the frame having: a first horizontally extending peripheral member; a second horizontally extending peripheral member substantially parallel to and spaced apart from the first horizontally extending peripheral member; and a track defined by an upper track portion provided on an edge of the first horizontally extending peripheral member and a lower track portion provided on a corresponding edge of the second horizontally extending peripheral member; at least two panels coupled to the frame, the at least two panels being translatable along the track; a battery module coupled to the frame and being contained in a first one or more of the panels; a stimulation module coupled to the frame and being contained in a second one or more of the panels; and control circuitry disposed within the flexible housing and coupled to the stimulation module and the battery module to control operation of the apparatus during use.

In yet another broad aspect, at least one embodiment described herein provides an apparatus for a functional electrical stimulation (FES) system. The apparatus may comprise a flexible housing comprising a frame that is releasably mountable on a user, the frame having: a first end; a second end opposite to the first end; a first peripheral member extending from the first end to the second end defining a top side; a second peripheral member extending from the first end to the second end substantially parallel to and spaced apart from the first peripheral member defining a bottom side; and a plurality of panels coupled to the frame and extending between the first peripheral member and the second peripheral member, the plurality of panels being adjustable and spaced apart to define at least one area that is substantially devoid of material; a battery module disposed within the frame; a stimulation module disposed within the frame; and control circuitry coupled to the battery module and the stimulation module.

In yet another broad aspect, at least one embodiment described herein provides a cuff unit for a functional electrical stimulation (FES) system, the cuff unit comprising a flexible housing comprising a frame that is releasably mountable on a user of the FES system; and a plurality of panels coupled to the frame, the plurality of panels being adjustable in location and at least one of the panels is configured to house a battery module, at least one of the panels is configured to house a stimulation module and at least one of the panels is configured to house control circuitry.

In at least some embodiments, at least some of the panels may be adjustably spaced apart to define at least one area that is substantially devoid of material between adjacent panels.

In at least some embodiments, the frame may comprise a first end; a second end opposite to the first end; a first peripheral member extending from the first end to the second end defining a top side of the frame; and a second peripheral member extending from the first end to the second end substantially parallel to and spaced apart from the first peripheral member defining a bottom side of the frame wherein the panels are arranged in a substantially vertical orientation between the first and second peripheral members.

It should be noted that the cuff units described herein may be used for an FES orthotic system. However, it may be possible for at least one of the cuff units described herein to be used with a different FES system for a different body part.

Other features and advantages of the present application will become apparent from the following detailed description taken together with the accompanying drawings. It should be understood, however, that the detailed description and the specific examples, while indicating preferred embodiments of the subject matter described in the application, are given by way of illustration only, since various changes and modifications within the spirit and scope of the application will become apparent to those skilled in the art from this detailed description.

DETAILED DESCRIPTION OF DRAWINGS

For a better understanding of the various embodiments described herein, and to show more clearly how these various embodiments may be carried into effect, reference will be made, by way of example, to the accompanying drawings which show at least one example embodiment, and which are now briefly described.

FIG. 2 illustrates an example embodiment of a cuff unit.

FIG. 3C illustrates an example embodiment of a panel that may include circuitry and/or batteries for the cuff unit shown in FIG. 3A.

FIG. 3D illustrates the cuff unit of FIG. 3A in a closed position.

FIG. 3H illustrates an exploded view of another example embodiment panel that houses batteries that may be used with the cuff unit of FIG. 3A.

FIG. 4C illustrates an example embodiment of fasteners in another cuff unit.

FIG. 4F illustrates another example embodiment of fasteners used with another cuff unit.

FIG. 4H illustrates another example embodiment of a cuff unit.

FIG. 7 illustrates an example of two ways of aligning a cuff unit on a user.

Figure 8A:
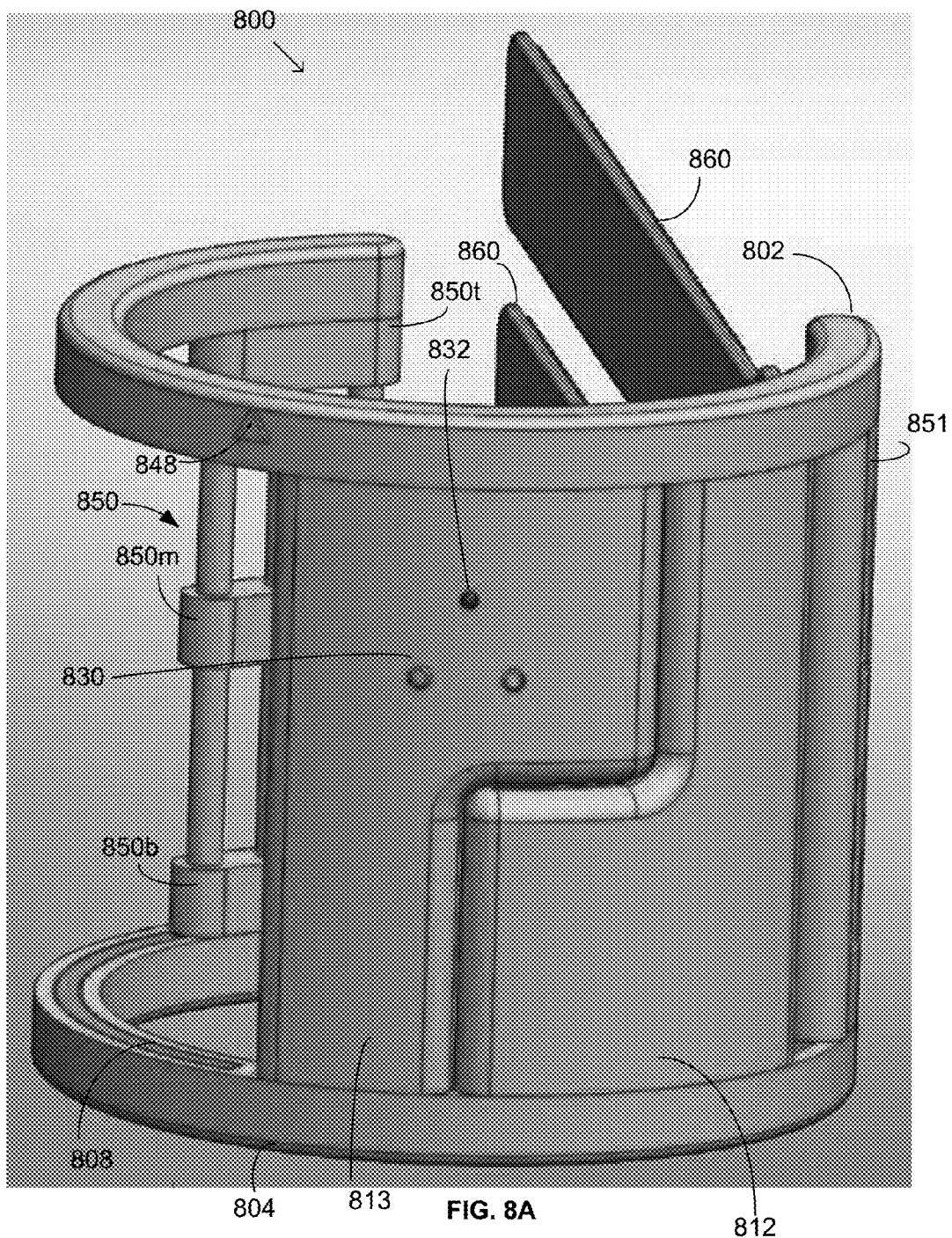
FIG. 8A illustrates another example embodiment of a cuff unit having adjustable panels.

FIG. 8E a rear exploded view of the cuff unit of FIG. 8A with the panels slightly apart.

Figure 8B:
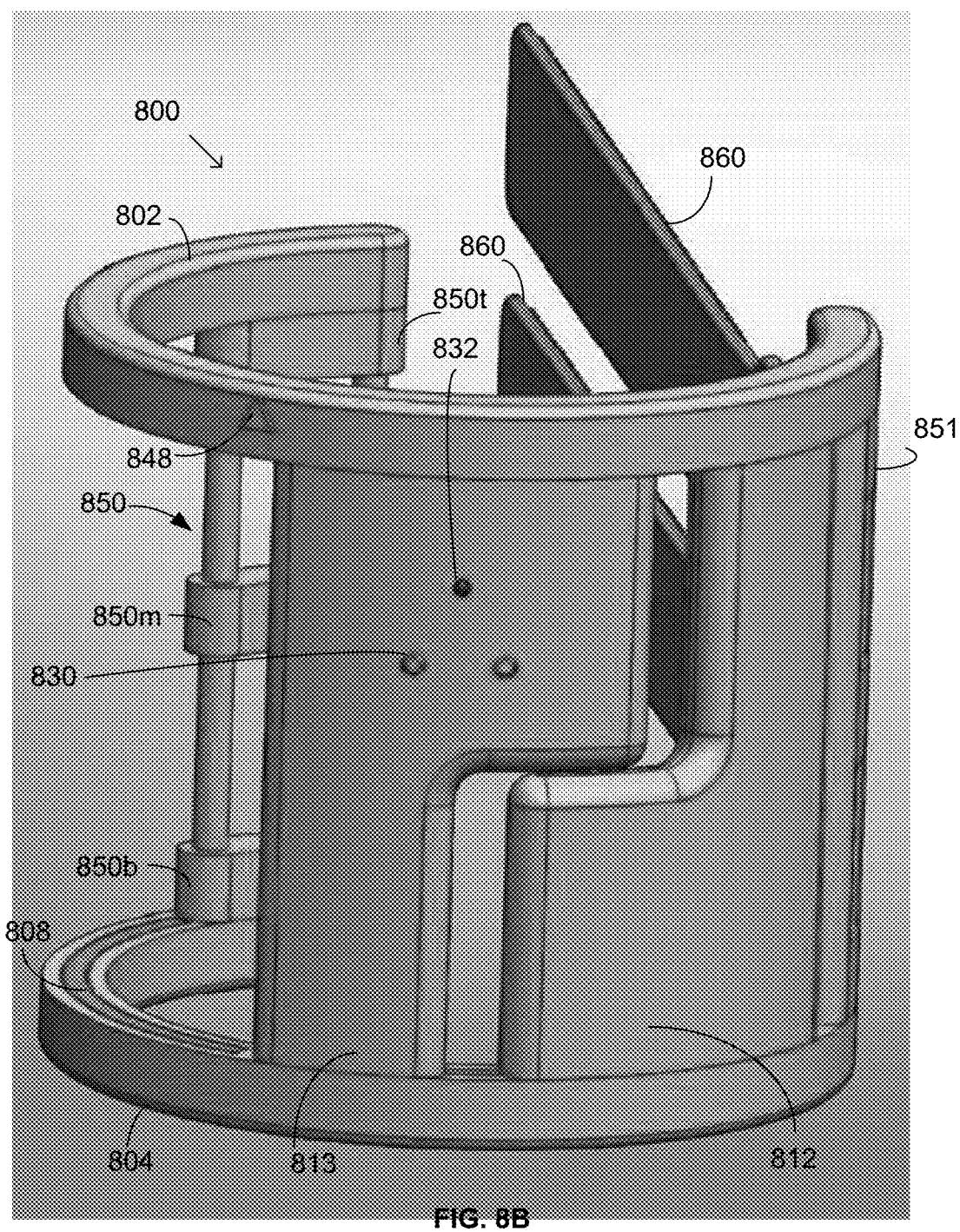
FIG. 8B is a view of the cuff unit of FIG. 8A with the panels slightly apart.
Figure 8C:
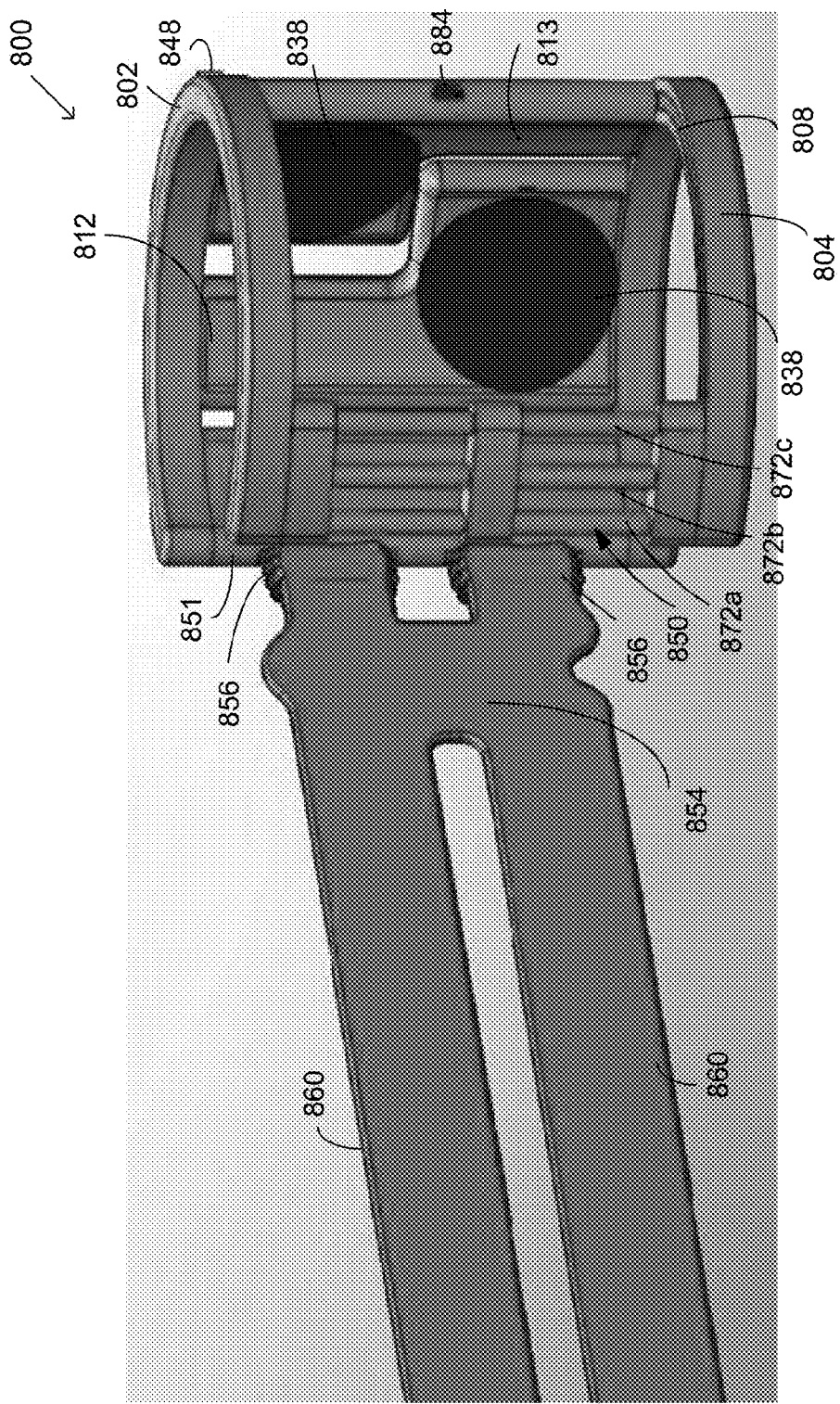
FIG. 8C is a rear view of the cuff unit of FIG. 8A with the panels slightly apart.
Figure 8D:
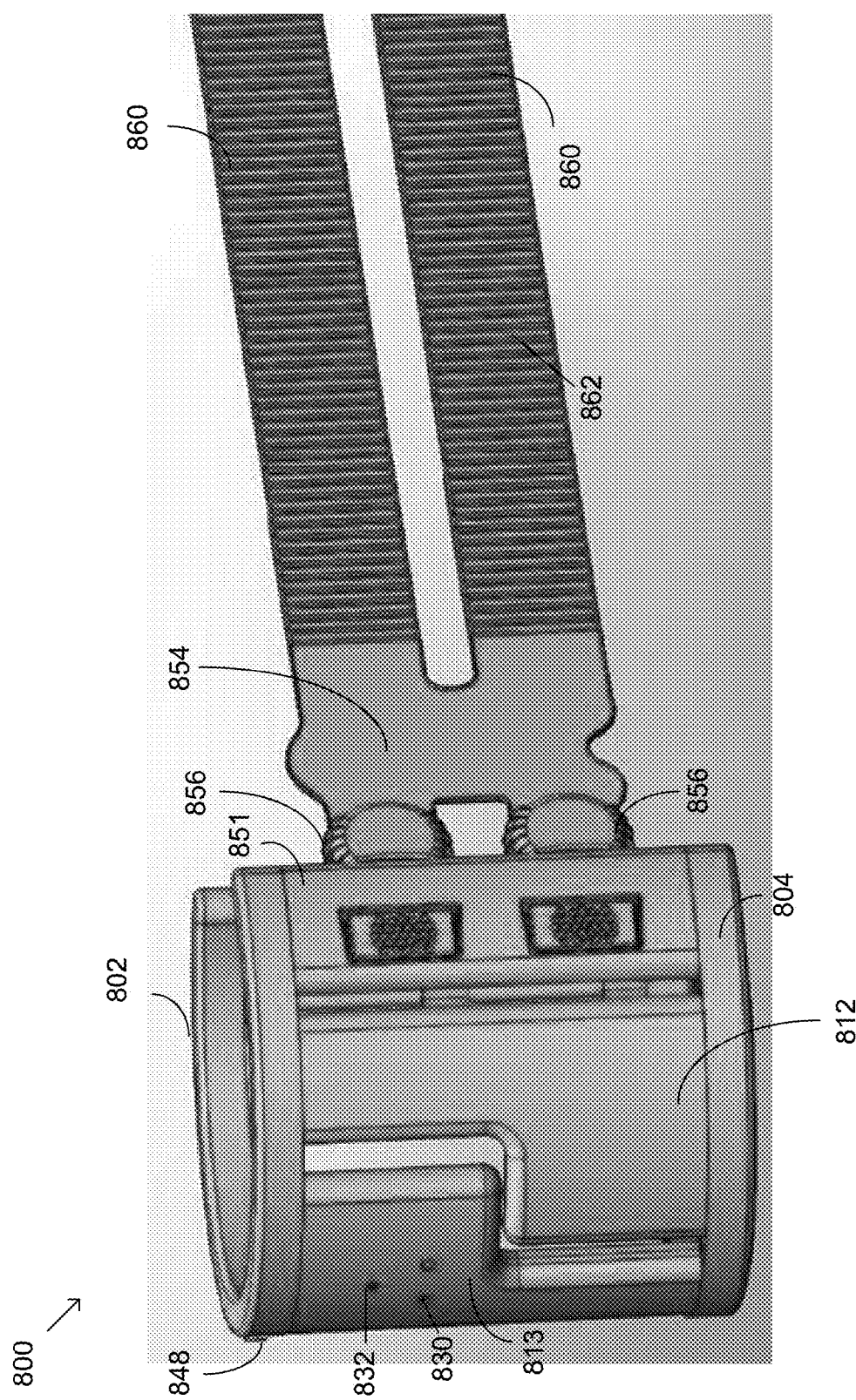
FIG. 8D is a side view of the cuff unit of FIG. 8A with the panels slightly apart.
Figure 8F:
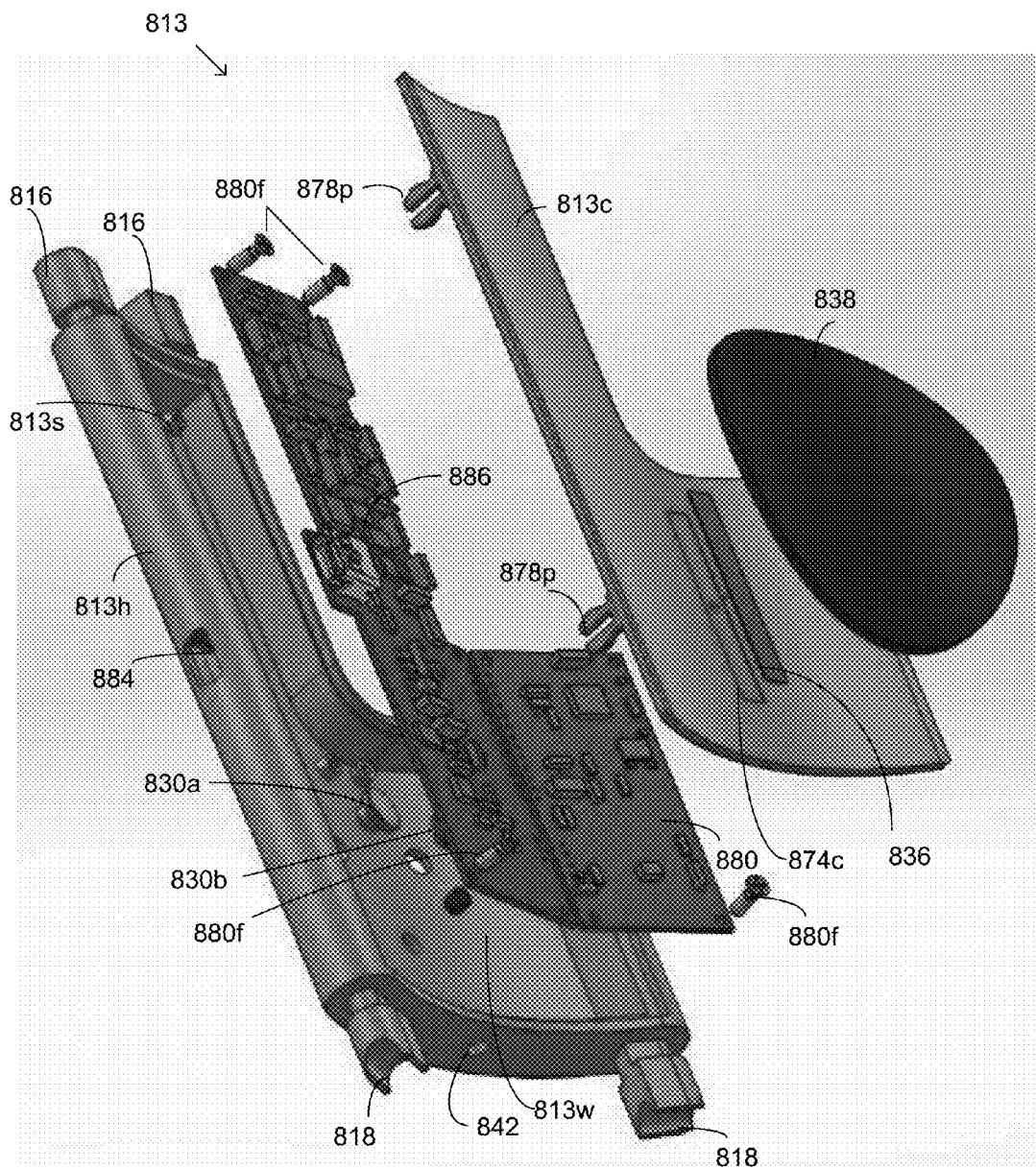

FIG. 8F is an exploded view of one of the panels of the cuff unit of FIG. 8A that houses two circuit boards and includes an electrode.

Figure 8G:
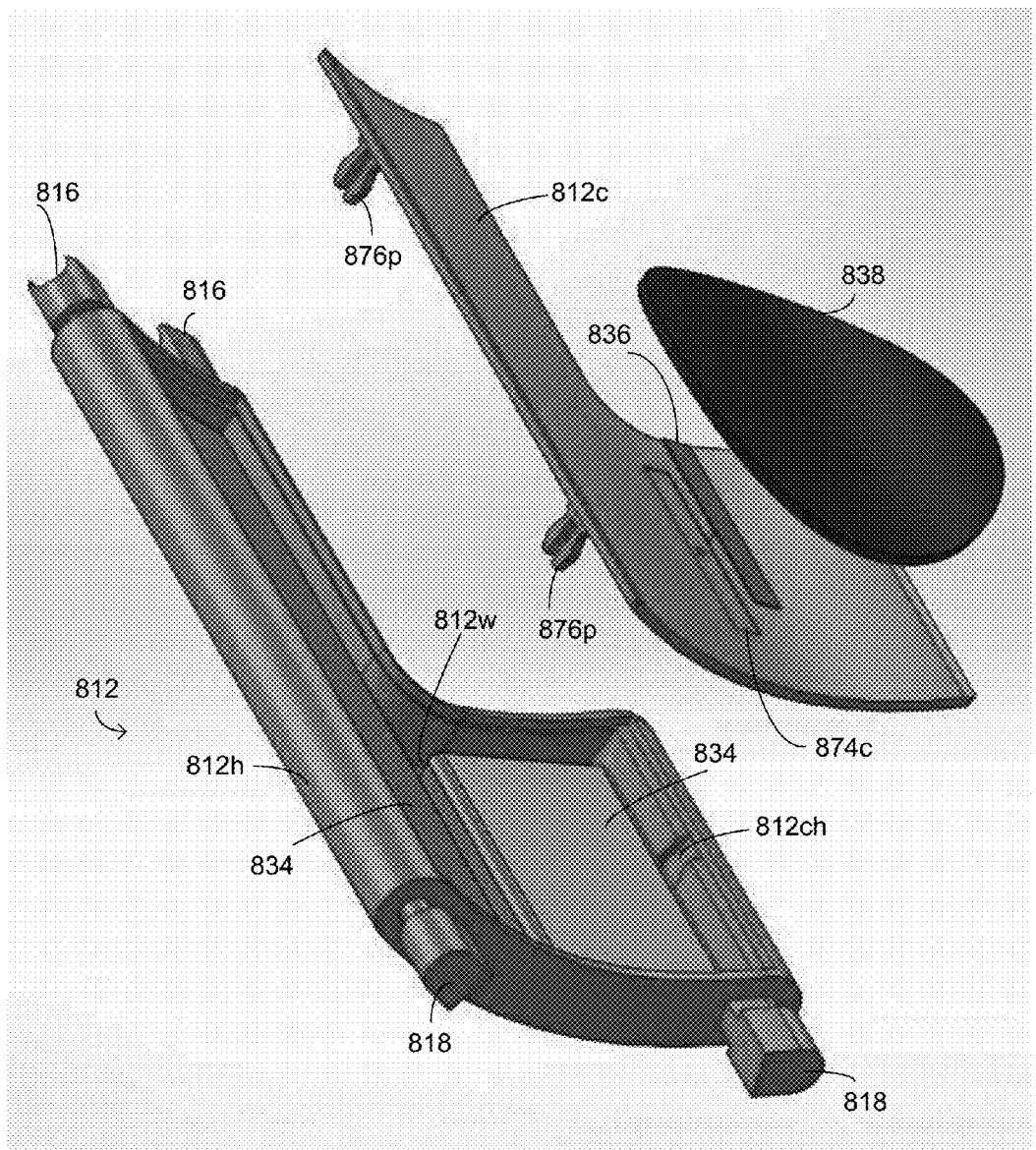

FIG. 8G is an exploded view of another one of the panels of the cuff unit FIG. 8A that houses batteries and includes an electrode.

Further aspects and features of the embodiments described herein will appear from the following description taken together with the accompanying drawings.

DESCRIPTION OF VARIOUS EMBODIMENTS

The various embodiments described herein generally relate to an apparatus that can be used with an FES system, and more particularly are related to a cuff unit for a FES orthotic system that can be used to apply stimulation signals to a user.

Various apparatuses or processes will be described below to provide an example of an embodiment of the claimed subject matter. No embodiment described below limits any claimed subject matter and any claimed subject matter may cover processes or apparatuses that differ from those described below. The claimed subject matter is not limited to apparatuses or processes having all of the features of any one apparatus or process described below or to features common to multiple or all of the apparatuses or processes described below. It is possible that an apparatus or process described below is not an embodiment of any claimed subject matter. Any subject matter that is disclosed in an apparatus or process described below that is not claimed in this document may be the subject matter of another protective instrument, for example, a continuing patent application, and the applicants, inventors or owners do not intend to abandon, disclaim or dedicate to the public any such claimed subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures and components have not been described in detail so as not to obscure the example embodiments described herein. Also, the description is not to be considered as limiting the scope of the example embodiments described herein.

It should also be noted that the terms "coupled" or "coupling" as used herein can have several different meanings depending in the context in which these terms are used. For example, the terms "coupled" or "coupling" can have a mechanical or electrical connotation. For example, as used herein, the terms "coupled" or "coupling" can indicate that two elements or devices can be directly connected to one another or connected to one another through one or more intermediate elements or devices via an electrical element, electrical signal or a mechanical element depending on the particular context.

It should also be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

At least some of the elements described that are implemented via software may be written in a high-level procedural language such as object oriented programming or a scripting language. Accordingly, the program code may be written in C, SQL or any other suitable programming language and may comprise modules or classes, as is known to those skilled in object oriented programming. It should also be understood that at least some of the elements of the various systems described herein that are implemented via software may be written in assembly language, machine language or firmware as needed. In either case, the program code can be stored on a storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

The computing devices that may be used in the various embodiments described herein generally include at least one processor, a data storage system (including volatile memory or non-volatile memory or other data storage elements or a combination thereof), and at least one communication interface. For example, and without limitation, the programmable devices (referred to herein as computing devices) may be a server, a network appliance, an embedded device, a computer expansion module, a personal computer, a laptop, a personal data assistant, a cellular telephone, a smart-phone device, a tablet computer, a wireless device or any other computing device capable of being configured to carry out the methods described herein. The particular embodiment depends on the application of the computing device. For example, a server can be used to provide a centralized database and/or a remote programming interface while an embedded device may be used for components that are worn or otherwise directly used by the wearer of an FES orthotic system.

In some embodiments, the communication interface may be a network communication interface. In embodiments in which elements are combined, the communication interface may be a software communication interface, such as those for inter-process communication (IPC). In still other embodiments, there may be a combination of communication interfaces implemented as hardware, software, and a combination thereof.

Program code may be applied to input data to perform at least some of the functions described herein and to generate output information. The output information may be applied to one or more output devices, in known fashion.

At least some of the programs may be implemented in a high level procedural or object oriented programming and/or scripting language, or both, to communicate with a computer system. However, other programs may be implemented in assembly or machine language, if desired. In any case, the language may be a compiled or interpreted language. The computer programs may be stored on a storage media or a device (e.g. ROM, magnetic disk, optical disc) readable by a general or special purpose programmable device, for configuring and operating the programmable device when the storage media or device is read by the programmable device to perform the procedures described herein. Embodiments of the system may also be considered to be implemented as a non-transitory computer-readable storage medium, configured with a computer program, where the storage medium so configured causes a computing device to operate in a specific and predefined manner to perform the functions described herein.

Furthermore, some of the programs associated with the system, processes and methods of the embodiments described herein are capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments the medium may be transitory in nature such as, but not limited to, wireline transmissions, satellite transmissions, internet transmissions (e.g. downloads), media, digital and analog signals, and the like. The computer useable instructions may also be in various formats, including compiled and non-compiled code.

Figure 1:
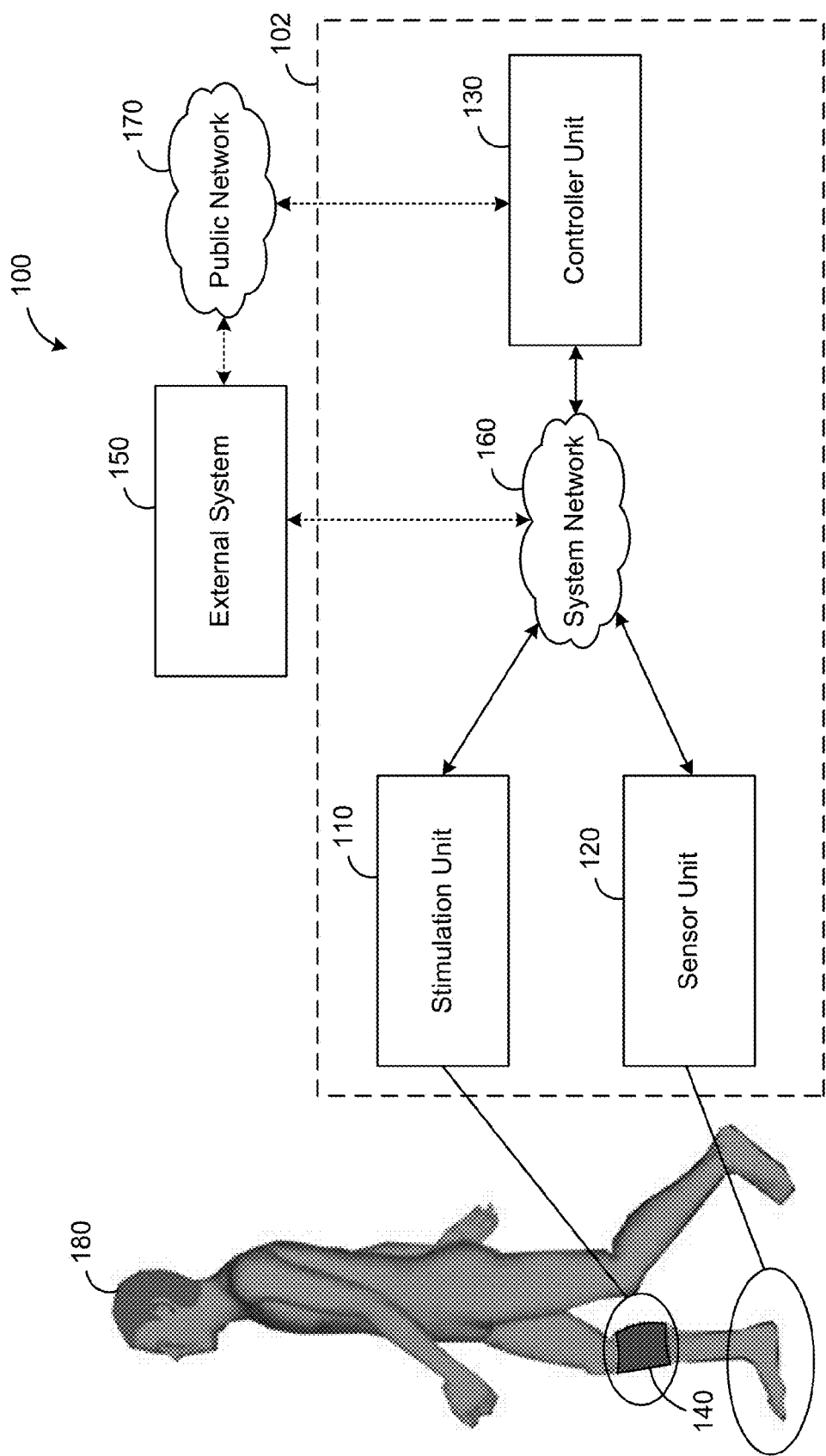
FIG. 1 is a block diagram of components including a cuff unit for a functional electrical stimulation (FES) system in accordance with an example embodiment.

Reference is first made to FIG. 1, which shows a block diagram 100 of components interacting with a functional electrical stimulation (FES) system 102 in accordance with an example embodiment. The FES system 102 generates electrical stimulation signals to assist individuals, such as a user 180, with damaged or weakened muscles in a lower leg. The FES system 102 may generate stimulation signals for various purposes, such as to facilitate movement of the user 180, to reeducate any affected muscles in the user 180, to retrain the user 180 to walk, or to retard atrophy in muscles due to disuse, for example.

When facilitating movement of the user 180, the FES system 102 can generate stimulation signals to trigger movement at affected muscles. In the case of a user 180 with foot drop, for example, the FES system 102 may generate stimulation signals that are synchronized with a swing phase of a gait of the user 180 in order to help the user 180 lift the foot and prevent the foot from dragging on the ground.

As shown in FIG. 1, the FES system 102 includes a stimulation unit 110, a sensor unit 120, a controller unit 130 and a cuff unit 140. The stimulation unit 110, the sensor unit 120 and the controller unit 130 may communicate with each other via a system network 160. As also shown in FIG. 1, the FES system 102 may also communicate with an external system 150 via the system network 160 and/or possibly via a public network 170. The FES system 102 may receive signal parameters and other operational instructions from the external system 150 and may also transmit operational data to the external system 150.

The stimulation unit 110 generates and delivers electrical stimulation signals to the user 180. As shown in FIG. 1, the stimulation unit 110 may be provided in association with the cuff unit 140 that is worn by the user 180 at a location on the user 180 that is to receive the stimulation signals. In the example of FIG. 1, the cuff unit 140 is worn on the lower leg of the user 180 to stimulate nerves located in the lower leg. The stimulation unit 110 may include various modules for generating and delivering the stimulation signal to the user 180. It will be understood that the various modules may be implemented in hardware, software, or a combination of hardware and software. The stimulation unit 110 may be implemented in several ways as is known by those skilled in the art.

The stimulation unit 110 may generate stimulation signals based on signal parameters stored at the stimulation unit 110 or signal parameters received via the system network 160 from the external system 150 or the signal parameters may be received from the controller unit 130.

To deliver the stimulation signal, the cuff unit 140 includes at least two contact members in electrical communication with the stimulation unit 110 including electrodes that are positioned substantially around a target nerve that is to receive the stimulation signal. For example, the contact members may be positioned substantially around a target nerve that is to receive the stimulation signal. Two of the contact members form a current path there between over which the stimulation signal travels to stimulate the target nerve. Accordingly, the contact members may be provided in pairs.

The stimulation unit 110 may also generate operation data, such as stimulation status data, to be displayed at the cuff unit 140 or by the controller unit 130. For example, the stimulation unit 110 may include a display component, such as an LCD display in some cases. The cuff unit 140 may include also status indicator components such as status indicators lights in some cases, for example.

The stimulation unit 110 can be provided in association with the cuff unit 140. The cuff unit 140 allows the user 180 or a medical practitioner to position the stimulation unit 110 as desired near the nerves that are to be stimulated. The cuff unit 140 can include a frame with a plurality of panels containing the stimulation unit 110, the contact members, as well as a battery module. The cuff unit 140 can provide a self-contained, compact, portable and safe apparatus for applying stimulation signals to the user 180 by housing the stimulation unit 110, the battery module and at least a portion of the contact members entirely within several panels of the frame.

The cuff unit 140 can be sealed such that all of the electronic circuit portions are contained within a waterproof frame that is able to withstand some periods of rain and fluid spills. The stimulation unit 110, the battery module and the contact members may be electrically coupled using electrical wires that can also be housed entirely within the frame of the cuff unit 140. Housing the electrical wires within the frame of the cuff unit 140 can prevent damage or deterioration that may occur if the wires were exposed. Housing the electrical wires within the frame of the cuff unit 140 also provides a more attractive appearance to the cuff unit 140 and increase safety.

The cuff unit 140 can be manufactured using various materials suitable for use in medical products with humans. In some cases, the cuff unit 140 can be manufactured from FDA approved rubber materials such as silicone rubber. The materials used in the cuff unit 140 may have flexible and elastic characteristics that allow them to flex to accommodate movements of the user 180.

The cuff unit 140 can be releasably mountable on the user 180. Accordingly, the cuff unit 140 can include various types of fasteners for releasably and securely mounting the cuff unit 140 on the user 180. In some cases, the cuff unit 140 fasteners can include various configurations of snap-fit buckles, for example. Alternatively, the cuff unit 140 may use alternative fasteners such as, but not limited to, adjustable belt fasteners, for example.

In some cases, adjustable belt fasteners can be used in conjunction with a socket provided by a support panel of the cuff unit 140. The user 180 may adjust the fit of the cuff unit 140 by pressing a tongue in the support panel socket and then fastening or loosening the adjustable belt fastener. In other cases, the adjustable belt fasteners may be used in a self-locking configuration with support posts provided on a support panel of the cuff unit 140. In other cases, the cuff unit 140 may have fasteners using a combination of adjustable belt fasteners, snap-fit buckles or other fastener types.

In some cases, the fasteners may be attached to the cuff unit 140 using fastener straps. The fastener straps can be adjustable straps that allow the user 180 to fasten or loosen the cuff unit 140 before or after it has been secured in place. In some cases, the fasteners and fastener straps may be made of elastic materials such that they are able to flex to accommodate various movements of the user 180. The fastener straps can be made of various materials suitable for use with humans such as, but not limited to, textile elastic webbing, for example. The fasteners and adjustable belts can also be made from materials similar to those used in the frame of the cuff unit 140 such as, but not limited to, silicone rubber, for example.

The controller unit 130 can define the signal parameters of the stimulation signal and transmit the signal parameters to the stimulation unit 110 via the system network 160. The controller unit 130 may define the signal parameters based on data received from the sensor unit 120, the external system 150, or parameters stored locally or received at the controller unit 130.

The external system 150 may include any computing device with at least one processor and memory, and capable of receiving, sending, and processing instructions associated with the operation of the FES system 102. The external system 150 may be directly attached to the FES system 102, such as by a USB connector port provided in some embodiments of the cuff unit 140, or may connect remotely with the FES system 102 as long as the external system 150 can communicate with the FES system 102 via the public network 170 or the system network 160.

The external system 150 may be an electronic tablet device, a personal computer, a workstation, a server, a portable computer, a mobile device, a personal digital assistant, a laptop, a smart phone, a WAP phone, an interactive television, video display terminals, gaming consoles, portable electronic devices or any combination of these.

Data associated with the usage of the FES system 102 by the user 180 may be transmitted to the external system 150 via the system network 160 or the public network 170. A third party, such as a doctor, clinician or other medical personnel, may access the external system 150 to retrieve the usage data. Based on the usage data, the third party may decide to vary and update certain signal parameters associated with the stimulation signals that are generated by the stimulation unit 110. The external system 150 may then transmit the updated signal parameters to the FES system 102 via the system network 160 or the public network 170.

The system network 160 includes any network capable of carrying data between each of the stimulation unit 110, the sensor unit 120 and the controller unit 130, as well as between the FES system 102 and the external system 150. The system network 160 may include one or more wireless communication networks, such as a Wireless Local Area Network (WLAN), a local area network implemented by using technologies such as, but not limited to, Bluetooth™ technology or may be infrared light in certain circumstances or other networks implemented using similar protocols and technologies. The system network 160 may also include multiple sub-networks. In some embodiments, the cuff unit 140 can include a wireless communication module capable of connecting to the wireless communication networks of the system network 160.

Networks implemented using Bluetooth technologies may be Personal Area Networks (PANs) and can provide enhanced security in comparison with other wireless networks. It is well known that a Bluetooth communication network is capable of exchanging data between different devices over short distances using short-wavelength radio transmissions in the ISM radio band of 2,400 to 2,480 MHz.

The public network 170 can include any network capable of carrying data between the external system 150 and the FES system 102. Generally, the public network 170 may be any long-range communication network that is used as the system network 160. Accordingly, unlike the system network 160, the public network 170 may also facilitate communication for the external system 150 when it is outside of the range of system network 160. For example, the public network 170 may be implemented using the Internet, an Ethernet, a plain old telephone service (POTS) line, a public switch telephone network (PSTN), an integrated services digital network (ISDN), a digital subscriber line (DSL), coaxial cable, fiber optics, satellite, mobile, wireless (e.g. Wi-Fi, WiMAX, 3G or 4G technologies), an SS7 signaling network, a fixed line, a local area network, a wide area network, and others, including any combination of these.

Referring now to FIG. 2, shown therein is an example embodiment of a cuff unit 200 for use with a functional electrical stimulation (FES) orthotic system. The cuff unit 200 is generally provided as a flexible housing comprising a frame and at least one panel 212. As mentioned above, the cuff unit 200 can be made of various materials that are sturdy yet have flexible, elastic properties that are suitable for use with humans. In some cases, the cuff unit 200 can be made of FDA approved silicone rubber or other FDA approved materials.

As shown in FIG. 2, the frame comprises set of horizontally extending peripheral members including a first peripheral member 202 that defines an upper periphery of the frame and a second peripheral member 204 substantially parallel to and spaced apart from the first peripheral member 202. The second peripheral member 204 defines a lower periphery of the frame.

There is a gap between ends 202a and 202b in the first peripheral member 202. There is a corresponding gap (not shown) in the second peripheral member 204. The flexibility of the cuff unit 200 along with the gaps allows it to be used as a clasp to form a friction fit around the upper portion of the lower leg of the user 180 during use.

Each of the first peripheral member 202 and the second peripheral member 204 has a width or thickness that defines a frame width for the frame. As shown in FIG. 2, each of the panels 212 extends in a substantially vertical direction between the first and second peripheral members 202 and 204. Each of the panels 212 can have a panel width that is less than or equal to the frame width. The panels 212 can thus be entirely contained within the frame.

In some cases, as is shown in FIG. 2, when the cuff unit 200 has multiple panels 212, the panels 212 can also be disposed in a spaced apart arrangement with respect to one another to define open areas within the frame that are substantially devoid of material. This can be beneficial to the user 180 of the cuff unit 200 as it can allow the area of skin underneath the open areas of the cuff unit 200 to be exposed to air.

The first peripheral member 202 can also include an alignment notch 246. The alignment notch 246 can be used to properly align the cuff unit 200 with a knee of the user 180 when the cuff unit 200 is mounted on the leg of the user 180. In some cases, the first peripheral member 202 can include other alignment indicators such as an arrow or other suitable marking to indicate the preferred alignment of the cuff unit 200 when worn during use. In some cases, an alignment indicator can be provided on other portions of the cuff unit 200 such as one of the panels 212 or the second peripheral member 204. In some cases, the cuff unit 200 may be provided without any alignment indicators.

The cuff unit 200 includes a battery module (not shown) having one or more batteries. Various types of batteries can be used with the cuff unit 200 such as alkaline batteries and lithium-ion batteries, for example. In some cases, the batteries may be rechargeable batteries that can be recharged using a USB connector port (not shown) provided on the cuff unit 200. The battery module can be contained entirely within one or more of the panels 212. Panels which include a battery module may be referred to as a battery panel.

The cuff unit 200 also includes a stimulation module (not shown in the figures), which is similar to the stimulation unit 110, and is coupled to the battery module. The stimulation module can be provided on a flexible printed circuit board (PCB) that is contained within one or more of the panels. In this example embodiment, the stimulation module may be contained within panel 213 which may be referred to as a control panel. The stimulation module may be any suitable stimulation module for use in a functional electrical stimulation (FES) orthotic system, such as the stimulation unit 110. The stimulation module is operable to generate stimulation signals to be applied to the user 180.

The stimulation signals can be generated based on signal parameters stored at the stimulation module or signal parameters received via a system network such as the system network 160, from an external system, such as the external system 150 or from a controller unit such as the controller unit 130. The stimulation module can also include a wireless communication module, such as a Bluetooth or Wi-Fi module for communicating with the system network, external system and the controller unit.

The cuff unit 200 also includes at least two contact members (not shown) that are at least partially connected to the frame. Each of the contacts members is electrically connected with the stimulation module. In use, the contacts members operate to apply the stimulation signals generated by the stimulation module to the user 180.

Each contact member can be associated with a different panel 212. The contact member may include a conductive member (not shown) that is contained within the panel 212 and an electrode 238 that is coupled to the conductive member and mounted to the associated panel 212. The conductive members can provide an electrical coupling between the stimulation module and the electrodes 238 so that the electrodes 238 can apply the stimulation signal generated by the stimulation module to the user 180.

The location of the electrodes is adjustable such that the electrodes are generally positioned substantially around a target nerve that is to receive the stimulation signals. The two electrodes form a current path therebetween over which the stimulation signal travels from the stimulation module to the target nerve for stimulation thereof and then back to the stimulation module. Accordingly, the contact members and electrodes may generally be provided in pairs.

In some cases, each contact member will be associated with a distinct panel 212. In some cases, multiple contact members can be associated with a single panel 212.

Each electrode 238 may be translatable with respect to the panel 212 to which it is mounted. Translating or adjusting the position of the electrode 238 may be beneficial so that the electrodes 238 can be aligned in a fitting session in which the cuff unit 200 is fitted to the user 180 so that the stimulation signals provided by the electrodes 238 can be targeted to the desired nerves of the user 180 when the cuff unit 200 is worn by the user 180. The conductive member provided with each contact member may extend throughout a portion of the panel 212 associated with that contact member so that the electrode 238 is maintained in electrical communication with the conductive member regardless of where it is mounted on the panel 212. The electrode 238 can be mounted to a panel 212 using an adhesive so that the position of the electrode 238 and the contact member is fixed after its proper location is determined in the fitting session.

The electrode 238 can be made using various materials suitable for use with humans. In some case, the electrodes 238 may be made from FDA approved materials. Similarly, any adhesives used with the electrodes 238 and with the cuff unit 200 in general are made from materials that are suitable for use with humans. For example, the adhesives used with the cuff unit 200 may be FDA approved for use in healthcare products. In at least some cases, the adhesives used with the cuff unit 200 may be waterproof adhesives.

In some cases, each of the panels 212 will extend in a substantially vertical direction from the first peripheral member 202 to the second peripheral member 204. Each panel 212 may have a first end that is engageable with the inner edge of the first peripheral member 202 and a second end that is engageable with the inner edge of the second peripheral member 204.

In some embodiments, the frame of the cuff unit 200 may also include a track (not shown). The track may be defined by an upper track portion (not shown) provided on an inner edge of the first peripheral member 202 and a lower track portion 208 that is provided on an inner edge of the second peripheral member 204. In some cases, the inner edge of the first peripheral member 202 is opposite to the inner edge of the second peripheral member 204. In some embodiments, the upper and lower track portions may be on an outer face of the first and second peripheral members 202 and 204 and the panels 212 and 213 include inward facing ribs or protrusions that engage the upper and lower track portions. In either of these embodiments, the upper and lower track portions are located on edges of the peripheral frames 202 and 204 that are correspond to one another such as, but not limited to, both upper and lower edges of the lower and upper peripheral members 204 and 202 or the other face or edge of the lower and upper peripheral members 204 and 202, for example.

In some cases, where the panel 212 is movable with respect to the frame, the panel 212 can be translated along the upper and lower tracks. Accordingly, the track allows the position of the panel 212 to be adjusted before use. In other embodiments, there is no track and the location of the panel 212 is not adjustable.

In some cases, the panels 212 can be re-adjustably movable with respect to the frame. In some other cases, the panels 212 are initially movable during an initial alignment of the cuff unit 200 (possibly during an initial fitting of the cuff unit 140 to the user 180) and then the panels 212 may be fixed in place using various suitable methods. For example, the panels 212 may be fixed in place using metal or plastic screws securing the panels 212 to the both the first peripheral member 202 and the second peripheral member 204.

In some cases, the panels 212 can be fixed in place using various other methods such as by using stubs or concave connector portions provided along the interior of the upper track portion and the lower track portion 208 and/or using adhesives.

In some cases, the panels may also include a status indicator light such as indicator light 232 and control buttons 230 (only one of which is labelled for ease of illustration). The indicator light 232 and the control buttons 230 provide the user 180 of the cuff unit 200 with an easily visible indication of the current status of the cuff unit 200 and a way to control the function of the cuff unit 200. For example, the indicator light 232 may be a bi-color LED indicator. One of the control buttons 230 may be used to reset the stimulation unit 110 and act as an on/off button while another of the control button 230 may be used to select a particular operating mode. For example, the user 180 can use the mode control button to select a training mode to educate their muscle without using the controller unit 130. The user 180 may also be able to use the mode control button to set the stimulation unit 110 to a walking mode of operation. In other embodiments, there may be more than two control buttons.

All of the electrical components are generally integrated within the cuff unit 200 which provides several benefits. For example, in some cases the cuff unit 200 can be sealed such that all of the electrical components are contained within a waterproof frame. A cuff unit 200 that is waterproof can be desirable to prevent deterioration or short-circuiting of the electrical components housed within the cuff unit 200 that could occur, for example when the cuff unit 200 is being used in the rain or when a user perspires.

Figure 3A:
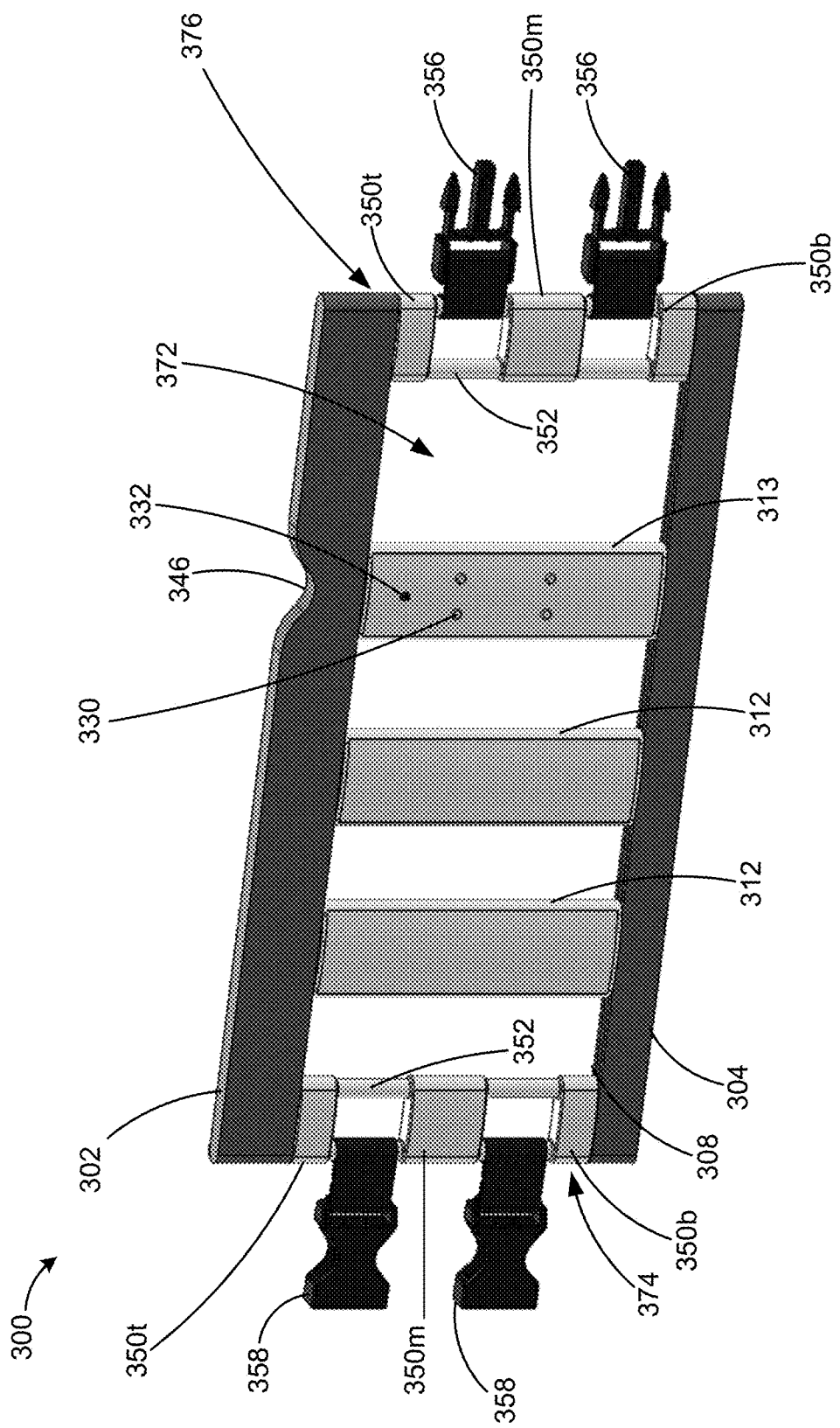
FIG. 3A illustrates another example embodiment of a cuff unit.

Referring now to FIG. 3A, shown therein is another example embodiment of a cuff unit 300. The cuff unit 300 is also a flexible cuff unit suitable for being fitted around the leg of the user 180. The cuff unit 300 includes first and second peripheral members 302 and 304. The first peripheral member 302 defines a top side or upper periphery of the frame of the cuff unit 300. The second peripheral member 304 defines a bottom side or lower periphery of the frame of the cuff unit 300. Both the first and second peripheral members 302 and 304 extend from a first end 374 of the cuff unit 300 to a second end 376. A plurality of panels 312 and 313 may extend in a substantially vertical direction from the first peripheral member 302 to the second peripheral member 304.

The cuff unit 300 may also include support panels 350 that may extend in a substantially vertical direction from the first peripheral member 302 to the second peripheral member 304. The support panels 350 can be used to attach fasteners to the frame of the cuff unit 300. In the example embodiment of the cuff unit 300, the support panels 350 include a pair of support posts 352 and separate sub-panels 350$t$, 350$m$ and 350$b$. In some cases the support panels 350 can include one or more than two support posts 352 while in other cases the support panels 350 may not have any support posts 352 and the fastener members are attached in some other way to the support panels. The fastener members can be attached to any of the support posts 352. In some alternative embodiments, the support panels 350 may include a socket that can receive a male fastener member to secure the cuff unit 300 to the user 180.

For the cuff unit 300, a female fastener member 358 and a male fastener member 356 can be attached to the support posts 352 at the first 374 end and the second end 376 of the cuff unit 300, respectively. The male and female fastener members 356 and 358 together form a snap-fit buckle type fastener. When the cuff unit 300 is placed around the leg of the user 180, the male fastener member 356 can releasably engage with the female fastener member 358 to secure the cuff unit 300 in place on the leg of the user 180 during use.

The top sub-panel 350$t$ functions to provide a space between the first peripheral member 302 and either the top male fastener 356 or the top female fastener 358. The middle sub-panel 350$m$ functions to provide a space between the top and bottom male fasteners 356 or the top and bottom female fastener members 358. The sub-panel 350$b$ functions to provide a space between the second peripheral member 304 and either the lower male fastener 356 or the lower female fastener 358.

As will be apparent to a skilled reader, various other types of fasteners or buckles can be used to secure the cuff unit 300 in place. For example, snap-fit buckle fasteners with and without adjustable straps may be used. In some cases, elasticized rubber bands can be used to provide tension that securely fastens the cuff unit 300 to the leg of the user 180.

The panels 312 and 313 as well as the support panels 350 can be spaced apart such that there are open areas between these panels, such as open area 372, that are substantially devoid of material. Accordingly, the cuff unit 300 having several open areas that are substantially devoid of material allows for more contact between skin of the user 180 and air so that the cuff unit 300 is more breathable. This can be beneficial to the user 180 when they wear the cuff unit 300 as it may prevent heat and perspiration from being trapped between the cuff unit 300 and the skin of the user 180 underneath the cuff unit 300.

The cuff unit 300 can also include a track defined by an upper track portion (not shown) and a lower track portion 308. The panels 312 and 313 can have a first end portion 316 (only one of which is labelled for ease of illustration) that is movably engageable with the upper track portion and a second end portion 318 (see FIG. 3C) that is movably engageable with the lower track portion 308. In some cases, the first and second end portions 316 and 318 can be hook shaped to engage with stubs provided on the interior of the upper track portion and the lower track portion 308. In some cases, the first and second end portions can include convex connector portions.

In some cases, the panels 312 can be translated along the track to align the electrodes to apply the stimulation signals to the desired nerve(s) of the user 180. In some cases, the panels 312 are initially movable with respect to the frame of the cuff unit 300, such as during a fitting of the cuff unit 300 to the leg of the user 180, and then may be secured in place. In some cases, the panels 312 may be re-adjustably movable with respect to the frame of the cuff unit 300. Having re-adjustably movable panels 312 can be useful to accommodate users whose legs may change shape and size over the lifespan of use of the cuff unit 300. In cases where the panels 312 are movable with respect to the frame of the cuff unit 300, the first and second end portions 316 and 318 may enable the panels 312 to be translated along the track.

At least one of the panels 312 may contain batteries and other components corresponding to a battery module. The panel 313, which may be referred to as a control panel, may contain one or more flexible printed circuit boards (PCB) including many of the components of the stimulation module. The stimulation module is coupled to the battery module and is operable to generate stimulation signals to be applied to the user 180 during use. In some cases, the stimulation module can be coupled to the battery module by one or more wires that are typically entirely contained within the first peripheral member 302 but in other embodiments may be contained within the second peripheral member or the first and second peripheral members 302 and 304.

The control panel 313 may also include a status indicator light 332 and control buttons 330 to provide a visible indication of the current status and allow for function control of the cuff unit 300, respectively. In the embodiment shown in FIG. 3A, the cuff unit 300 is provided with 4 control buttons 330. In some cases, the cuff unit 300 can have more status indicator lights 332. The control buttons 330 operate in a similar fashion as control buttons 230.

The cuff unit 300 also includes at least two contact members (not shown) that are connected to the frame and are electrically coupled with the stimulation module. The contact members are operable to apply the stimulation signals to the user of the cuff unit 300.

Figure 3B:
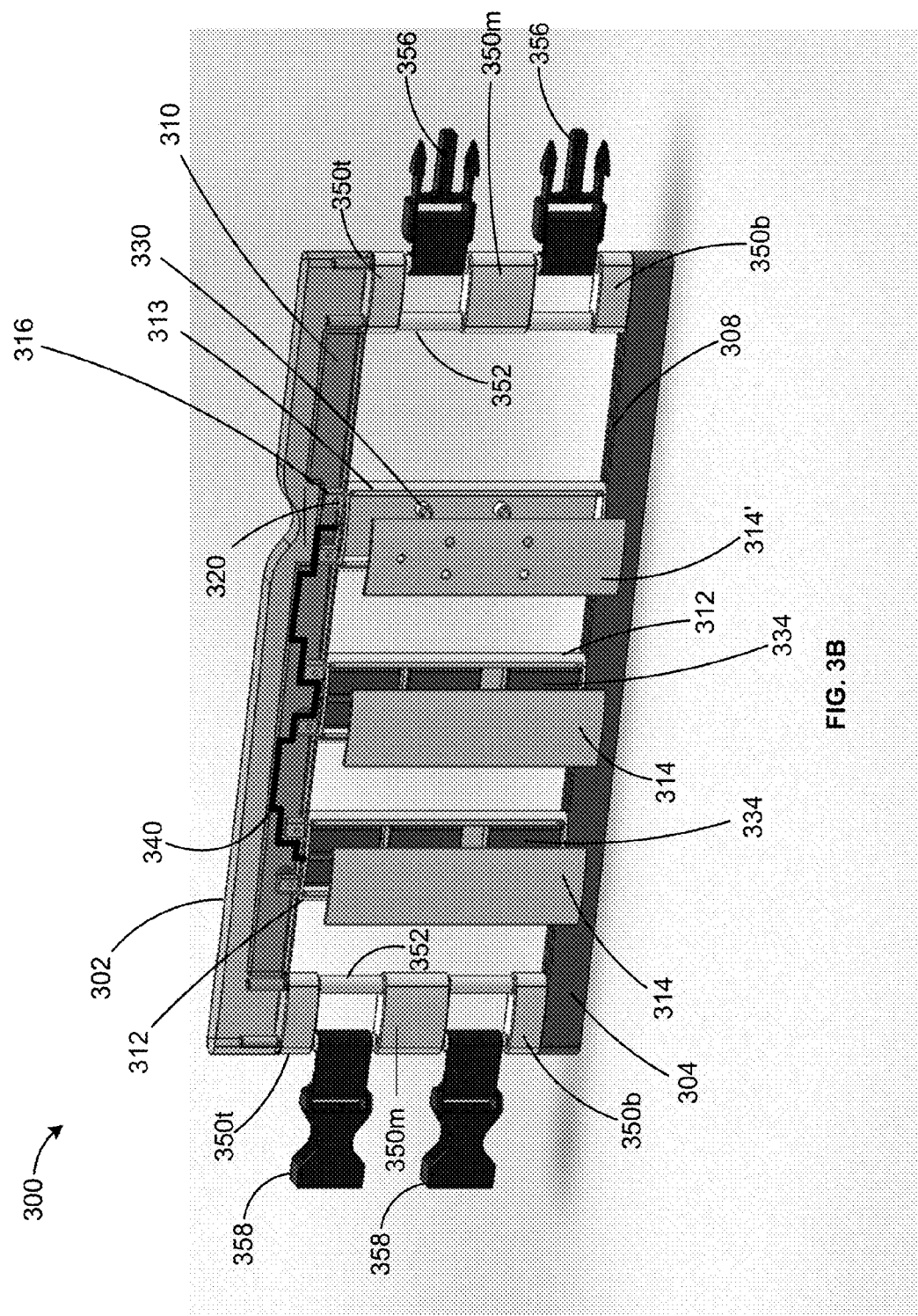
FIG. 3B illustrates a partially exploded view of the cuff unit shown in FIG. 3A.

Referring now to FIG. 3B, shown therein is a partially exploded view of the cuff unit 300. An inside portion of the first peripheral member 302 is shown as being transparent in FIG. 3B to show the interior structure of the first peripheral member 302 in accordance with at least one example embodiment of the cuff unit 300. The cuff unit 300 includes an upper track portion 310 provided on the lower inner edge of the first peripheral member 302 and a lower track portion 308 provided on the upper inner edge of the second peripheral member 304. The cuff unit 300 also includes a plurality of covers 314 for the panels 312 and cover 314' for the panel 313.

The first end portions 316 of the panels 312 and 313 can be provided with mounting holes 320. In alternative embodiments, each of the first and second end portions 316 and 318 can be provided with the mounting holes 320. The mounting holes 320 can be used to secure the panels 312 and 313 in place with screws or other suitable fasteners, such as pins or rivets, for example. In other embodiments, the first and/or second end portions 316 and 318 may not include the mounting holes 320, but may be provided with other suitable panel connectors for securing the panels 312 and 313 in place. In some embodiments, the panel connectors can be fixed in place permanently, while in other embodiments the panel connectors can be adjustable to re-align the panels 312.

In FIG. 3B, the panel covers 314 and 314' have been removed from the panels 312 and 313. A battery module having one or more batteries 334 may be provided in one or more of the panels 312. A stimulation module operable to generate stimulation signals to be applied to a user of the cuff unit 300 is also provided in the panel 313. The stimulation module can be electrically coupled to the battery module using electrical wires 340. In the example embodiment shown in FIG. 3A, electrical wires 340 are contained entirely within the first peripheral member 302. In other embodiments, the stimulation module may be housed in one of the panels 312 and the battery module may be housed in a different panel 312 while the control circuitry may be housed in the control panel 313. In some embodiments, the stimulation module and the control circuitry may be on the same printed circuit board.

The panels 312 also include at least two contact members that are electrically coupled with the stimulation module. The contact members are operable to apply the stimulation signals generated by the stimulation module to the user. The contact members can also be electrically coupled to the stimulation module using the electrical wires 340.

Housing electrical wires 340 entirely within the frame of the cuff unit 300 may provide various benefits. For instance, this feature can provide a more refined appearance to the exterior of the cuff unit 300 as there are no exposed wires. This feature can also provide some protection against physical damage to the electrical wires 340 since the wires may fray or get caught if they are on the exterior of the cuff unit 300. Furthermore, in embodiments where the frame of the cuff unit 300 is sealed to provide a waterproof cuff unit, housing the electrical wires 340 as well as the simulation module and the battery module within the panels and the frame protects these components from water damage that could be caused by water from the user perspiring or wearing the cuff unit in the rain.

Referring now to FIG. 3C, shown therein is an example embodiment of one of the panels 312. The panel 312 is elastic or flexible such that it can curve or flex when the cuff unit 300 is positioned on the user 180. The panel 312 includes first end portions 316 and second end portions 318. The first end portions 316 and second end portions 318 can be movably engageable with a track provided on the cuff unit 300.

The panel 312 shown in FIG. 3C is associated with a contact member. The panel 312 includes a conductive member 336 that extends vertically throughout a portion of the panel 312 and in this example, along a portion of the vertical center of the panel 312. An electrode can be coupled to the conductive member 336 and mounted on the panel 312. In some cases, the electrode can be mounted to the panel using an adhesive. In other embodiments, the conductive member 336 may have a different shape such as, but not limited to, fish bone or square, for example.

The conductive member 336 shown in FIG. 3C is shown as a vertically extending conductive strip. This allows the electrode to be translated with respect to the panel 312 and then the electrode may be secured for proper alignment with one or more nerves of the user 180 requiring stimulation. The conductive member 336 couples the electrode to the stimulation module. The electrode is operable to apply the stimulation signals to the user 180 of the cuff unit 300 in conjunction with at least one other contact member.

Each of the panels 312 and 313 can also include a wiring conduit 342. The wiring conduit 342 may allow at least one of the battery module, the stimulation module and the contacts members to be coupled to one another using electrical wires.

Figure 3E:
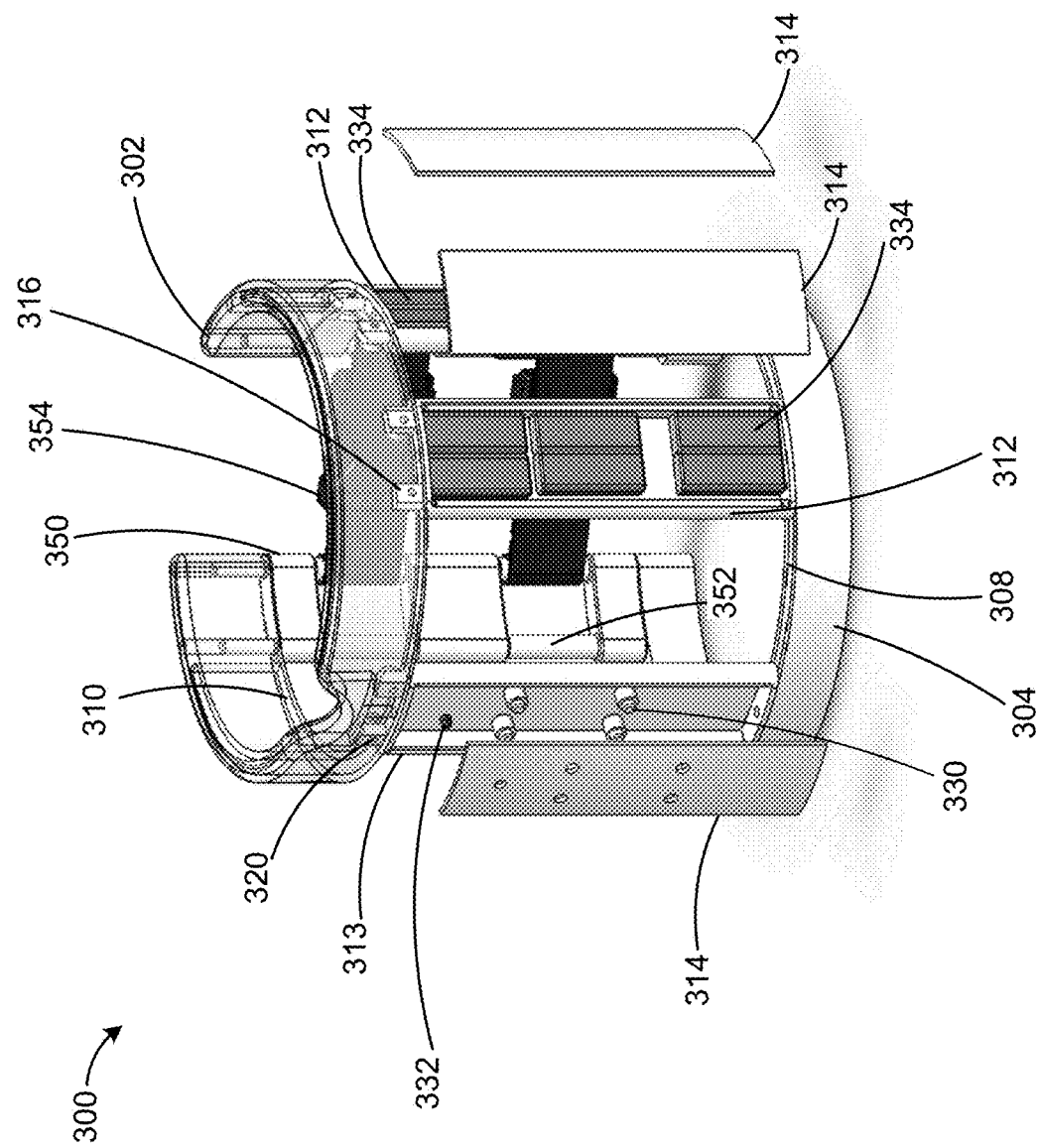
FIG. 3E illustrates a partially exploded view of the cuff unit of FIG. 3A in a closed position.

Reference is now made to FIGS. 3D and 3E. FIG. 3D shows an example embodiment of the cuff unit 300 in a closed position such as when it is mounted on the user 180. FIG. 3E shows a partially exploded view of the cuff unit 300 in a closed position with the top peripheral member 302 being transparent. The cuff unit 300 has a flexible frame that allows the cuff unit 300 to be secured about the leg of the user 180. In some cases, the stimulation module may be contained within the panels 312 and can be provided on a flexible PCB to allow the frame of the cuff unit 300 and the panels 312 greater freedom to flex as required.

A fastener portion 354 of the cuff unit 300 is shown with male and female fastener members 356 and 358 releasably matingly engaged. The fastener portion allows the user 180 to easily secure the cuff unit 300 to their leg for use and subsequently detach the cuff unit 300 when not in use. It should be understood that various other types of fastener components may be used in alternative embodiments of the cuff unit 300 to secure it in place around the leg of the user 180 during use.

In the alternative embodiment of the cuff unit 300' shown in FIG. 3D, the panels 312 have been secured in place using screws 322. In various embodiments, the screws 322 can be plastic screws, metal screws or any type of screws suitable for use in medical equipment with humans. The screws 322 are secured to the mounting holes 320 provided in at least one of the first end portion 316 and the second portion 318 of each panel 312. In other embodiments, rivets or other suitable fasteners may be used.

At least two contact members that are in electrical contact with the stimulation module are generally disposed with one or more of the panels 312. Each contact member can include a conductive member contained within a corresponding panel 312 to couple with an electrode 338 mounted on the exterior of the corresponding panel 312. The electrode 338 is mounted to the exterior of the corresponding panel 312 such that it is in contact with one or more desired nerves of the user 180 of the cuff unit 300' when in use. The contact members are operable to apply the stimulation signals generated by the stimulation module to the user 180. The panels 312 can be adjusted or translated with respect to the frame of the cuff unit 300' and then maintained in place during use such that the contact members are properly aligned with the nerve(s) of the user 180 requiring stimulation.

In some cases, the electrodes 338 can also be translated with respect to the panel 312 to which they are mounted so that they are properly aligned with the nerve(s) of the user 180 requiring stimulation. In some cases, the electrodes 338 can be initially translated with respect to the panel 312 and then secured in place. In other cases, the electrodes 338 can be re-adjustably translated with respect to the panel 312 to which they are mounted to re-position the electrodes 338 as desired.

Figure 3F:
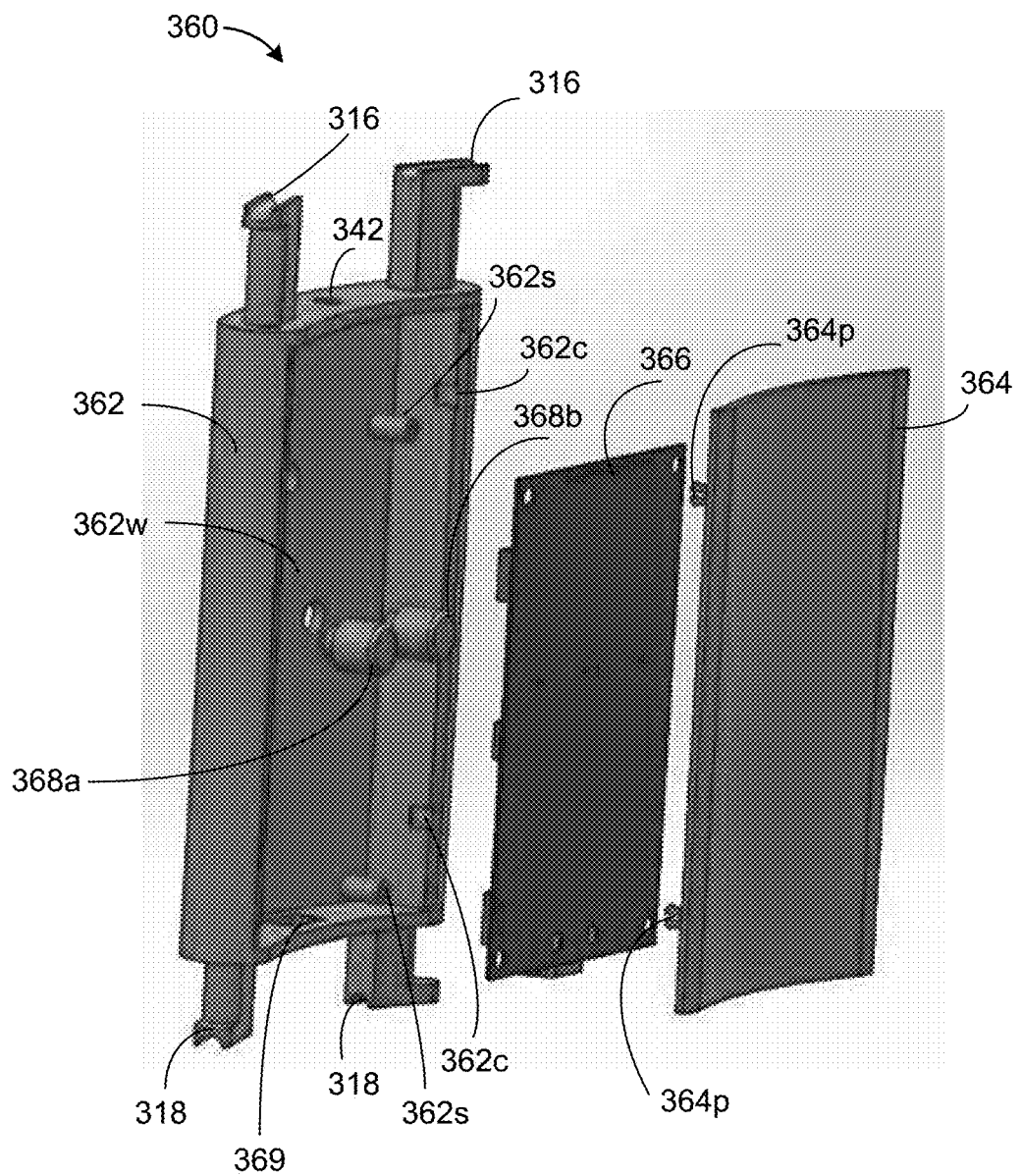
FIG. 3F illustrates an exploded view of an example embodiment of a panel that houses a circuit board that may be used with the cuff unit of FIG. 3A.

Referring now to FIG. 3F, illustrated therein is an exploded view of an example embodiment of a panel 360 that houses a circuit board 366 that may be used with the cuff unit 300. In this example, the panel 360 may be used as a control panel 313 and the circuit board 366 includes control circuitry (wiring or other electrical connections are generally not shown). The control panel 360 includes a main housing 362 with spacers 362s and channels 362c, and a cover 364 with resilient protrusions 364p. The control panel 360 also includes buttons 368a and 368b and a light element (not shown). In other embodiments, there may be more or fewer control buttons. The control buttons 368a and 368b and the light element protrude through apertures on the main wall 362w of the housing 362 when the control panel 360 is assembled. The spacers 362s provide support for the circuit board 366 so that it does not touch the main wall 362w of the housing 362 in operation. The resilient protrusions 364p of the cover 364 form a snap fit or friction fit with the channels 362c when the cover is mounted on the main housing 362. The control panel 360 also includes an aperture 369 to allow for an external hardware connection between the circuit board 366 and another electronic device. The connection may be a USB connection, for example.

Figure 3G:
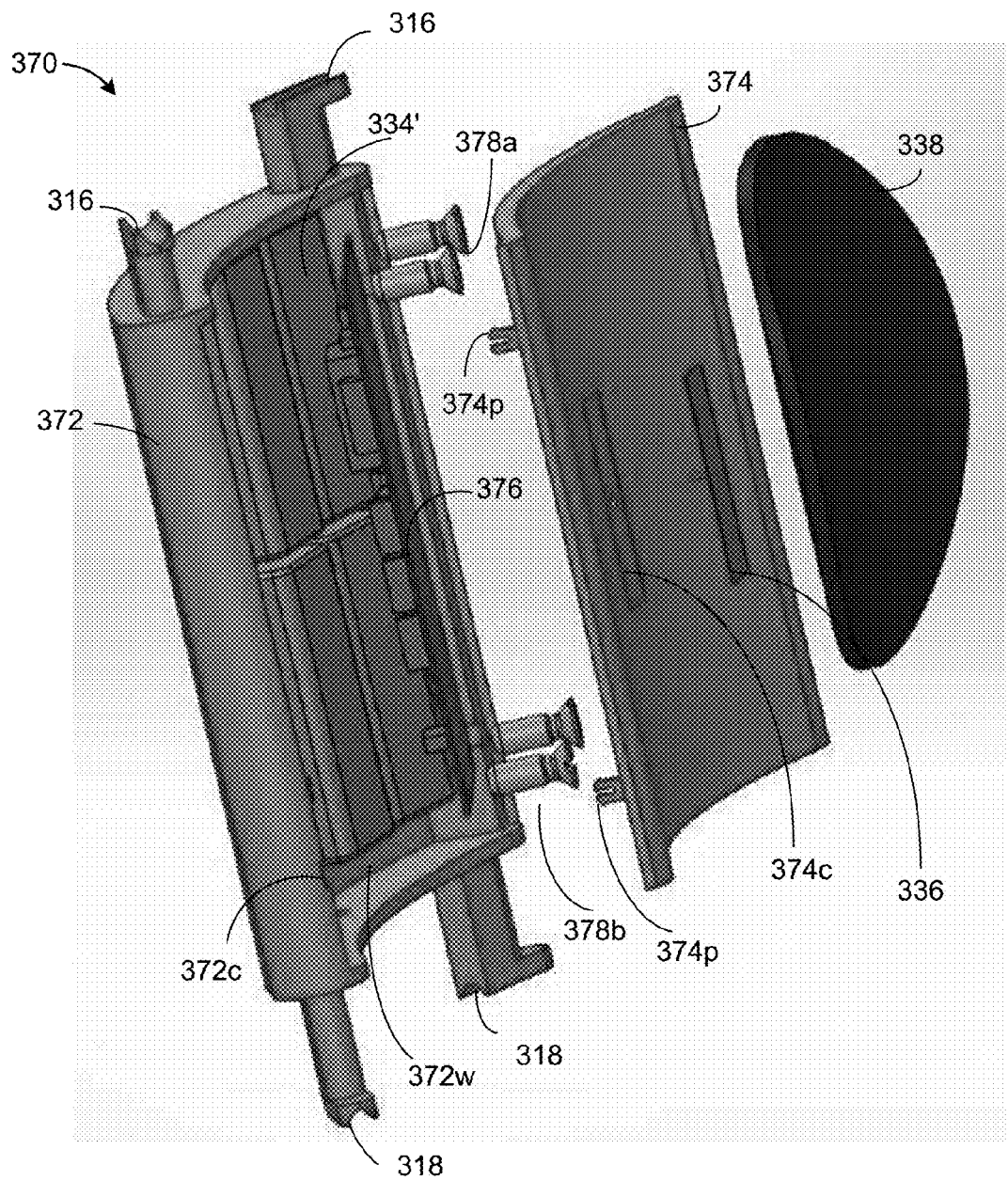
FIG. 3G illustrates an exploded view of an example embodiment of a panel that houses batteries and a circuit board that may be used with the cuff unit of FIG. 3A.

Referring now to FIG. 3G, illustrated therein is an exploded view of an example panel 370 that houses batteries 334' and a circuit board 376 that may be used with the cuff unit 300. In this example, the circuit board 376 includes the stimulation module (wiring or other electrical connections are generally not shown). The panel 370 includes a main housing 372, channels and threaded conduits (both not shown), and a cover 374 with resilient protrusions 374p. The battery cells 334' are mounted on wall 372w of the main housing 372 and then the circuit board 376 is mounted adjacent to the batteries in a side-by-side fashion. The fasteners 378a and 378b are then used to releasably engage the threaded conduits on the main housing 372 to firmly hold the circuit board 376 and the batteries 334' in place. In some embodiments, it may be possible to mount the circuit board 376 with the battery cells in a stack.

Embodiments where the stimulation module and the battery module are placed together in the same panel may have better energy properties. Typically, battery management circuitry is on the circuit board having the control circuitry. However, in some embodiments, such as the one shown in FIGS. 8A-8G, the battery module may be housed in a separate panel than the control circuit, which may help to simplify wire connections between these panels. An example of this is shown in the L-shaped panel design of FIGS. 8A-8G. Thick wires may be used to couple the stimulation module to the battery module since the stimulation module will consume most of the energy.

The resilient protrusions 374p of the cover 374 form a snap fit or friction fit with the channels 372c when the cover 374 is mounted on the main housing 372. The cover 374 also includes a channel 374c for receiving a conductive strip 336 to which electrode 338 is mounted. The channel 374c includes a small aperture to receive the conductive strip 336 and also allow the conductive strip 336 to make an electrical connection with the stimulation module on the circuit board 376.

Referring now to FIG. 3H, illustrated therein is an exploded view of another example panel 380 that houses batteries 334" that may be used with the cuff unit 300. The panel 380 includes a main housing 382 and channels 382c (only two are shown), and a cover 384 with resilient protrusions 384p. The battery cells 334" are mounted on wall 382w of the main housing 382 and then the resilient protrusions 384p of the cover 384 form a snap fit or friction fit with the channels 382c when the cover 384 is mounted on the main housing 382. The cover 384 also includes a channel 384c for receiving a conductive strip 336 to which electrode 338 is mounted. The channel 384c includes a small aperture to receive the conductive strip 336 and also allow the conductive strip 336 to make an electrical connection with the stimulation module that is in another panel. Electrical wiring or other contacts are not shown but it should be understood that there are electrical wires or electrical traces that couple the batteries 334" with the stimulation module that is in another panel. Also, there are electrical wires or electrical traces that couple the conductive strip 336 and the electrode 338 with the stimulation module that is in another panel.

It should be noted that the panels 360, 370 and 380 may be used in the cuff units 200, 400a to 400d, 400f, 400h, 700 and 800 shown and described in accordance with the teachings herein, although slight modifications may need to be made.

Figure 4A:
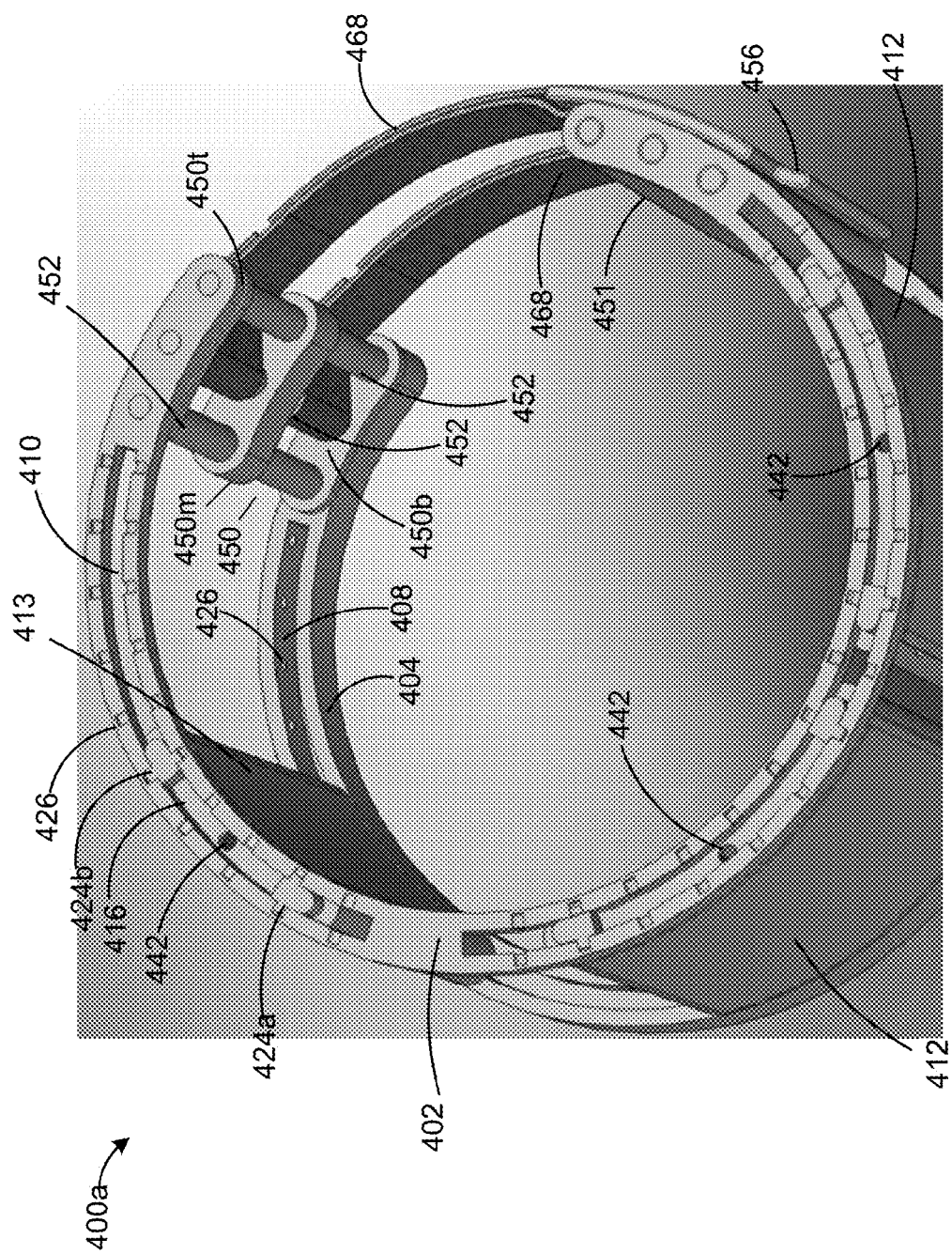
FIG. 4A illustrates an example embodiment of another cuff unit that has adjustable panels and adjustable electrodes.

Referring now to FIG. 4A, shown therein is another example embodiment of a cuff unit 400a that has adjustable panels and adjustable electrodes and a sectional view of first peripheral member 402 for displaying the structure of the upper track portion 410 (the lower track portion has similar structure). The frame of the cuff unit 400a has a first peripheral member 402 and a second peripheral member 404 extending substantially parallel to the first peripheral member 402. The cuff unit 400a also includes a plurality of panels 412 and 413 as well as support panels 450 and 451. The panels 412 and 413 extend in a substantially vertical direction from the first peripheral member 402 to the second peripheral member 404. The support panel 450 generally comprises members 450t, 450m and 450b and several posts 452. In alternative embodiments, the panels 412, 450 and 451 may have different shapes.

The frame of the cuff unit 400a can also include a track with an upper track portion 410 and a lower track portion 408. The upper track portion 410 may be provided on a lower inner edge of the first peripheral member 402 opposite a lower track portion 408 that is provided on an upper inner edge of the second peripheral member 404. Each of the panels 412 can include a first end portion 416 that is engageable with the upper track portion 410 and a second end portion (not shown) that is engageable with the lower track portion 408.

In some cases, the panel 412 can be movably engaged with the track of the cuff unit 400a. In these cases, the panel 412 can be translated along the track to adjust its position with respect to the frame of the cuff unit 400a. In some cases, the panel 412 is initially movable with respect to the frame and then subsequently fixed in place. In other cases, the panel 412 can be re-adjustably movable with respect to the frame to allow the panel 412 to be re-positioned after the cuff unit 400a has been initially aligned for a user. In some embodiments, panel 413 may be movable in a similar fashion.

As shown in FIG. 4A, the first end portions 416 of each panel 412 can include a pair of connector portions 424a and 424b (only one pair of which are numbered for simplicity). Similarly, the second end portions of each panel 412 can also include a pair of connector portions 424a and 424b (both not shown). The connector portions 424a and 424b are engageable with corresponding connector portions 426 (only a few of which are labeled for simplicity) provided along the upper track portion 410 and the lower track portion 408. The panels 412 can be translated along the track and secured into place by engaging the connector portions 424a and 424b with the concave connector portions 426. In this example embodiment, the connector portions 424a and 424b have a convex outer end and two tabs on either side while the connector portions 426 are slots sized to receive the tabs of the connector portions 424a and 424b.

The cuff unit 400a includes a battery module with one or more batteries that is contained within one or more of the panels 412. The cuff unit 400a also includes a stimulation module coupled to the battery module and contained within one or more of the other panels 412. The stimulation module can be any suitable stimulation module operable to generate stimulation signals to be applied to a user of the cuff unit 400a such as stimulation unit 110. The cuff unit 400a also includes control circuitry that is within the control panel 413. The cuff unit 400a also includes at least two contact members as was described previously for cuff units 140, 200 and 300.

Each of the panels 412 can also include a wiring conduit 442. The wiring conduit 442 may allow at least one of the battery module, the stimulation module, control circuitry and the contacts members to be coupled to one another using electrical wires. The wiring conduit 442 enables the cuff unit 400a to maintain all of the electrical wires within a sealed frame of the cuff unit 400a. The electrical wires can be housed within the first peripheral member 402 as shown above in FIG. 3B with regard to electrical wire 340. In some cases, the electrical wires may be housed within the second peripheral member 404. In some cases, the electrical wires may be housed within both the first and second peripheral members 402 and 404.

The cuff unit 400a includes support panels 450 and 451 having three support posts 452. In other embodiments, the support panels 450 and 451 can include one, two or more than three support posts 452. The support panel 450 comprises sub-panels 450t, 450m and 450b. The support panel 450 can be used to attach a fastener portion comprising fastener straps 468 to the frame of the cuff unit 400a. In some cases, the fastener straps 468 can be used in conjunction with various types of fasteners to secure the frame around a leg of the user 180. The fastener straps 468 can be attached to any of the support posts 452 of the support panels 450.

The support panel 451 includes a socket for a male fastener member 456 that is provided with the fastener straps 468. The male fastener member 456 can be engaged with the socket provided in the support panel 451, as shown, when a user secures the cuff unit 400a in place for use. A more detailed view of a similar support panel 451' is shown in FIG. 4E. One end of the fastener straps 468 may loop around buckles 456b and be secured in place perhaps using a clip or using loop and hook surfaces (e.g. Velcro) for opposing surfaces of the fastener strap 468 on the outer circumference of the cuff unit 400a.

Figure 4B:
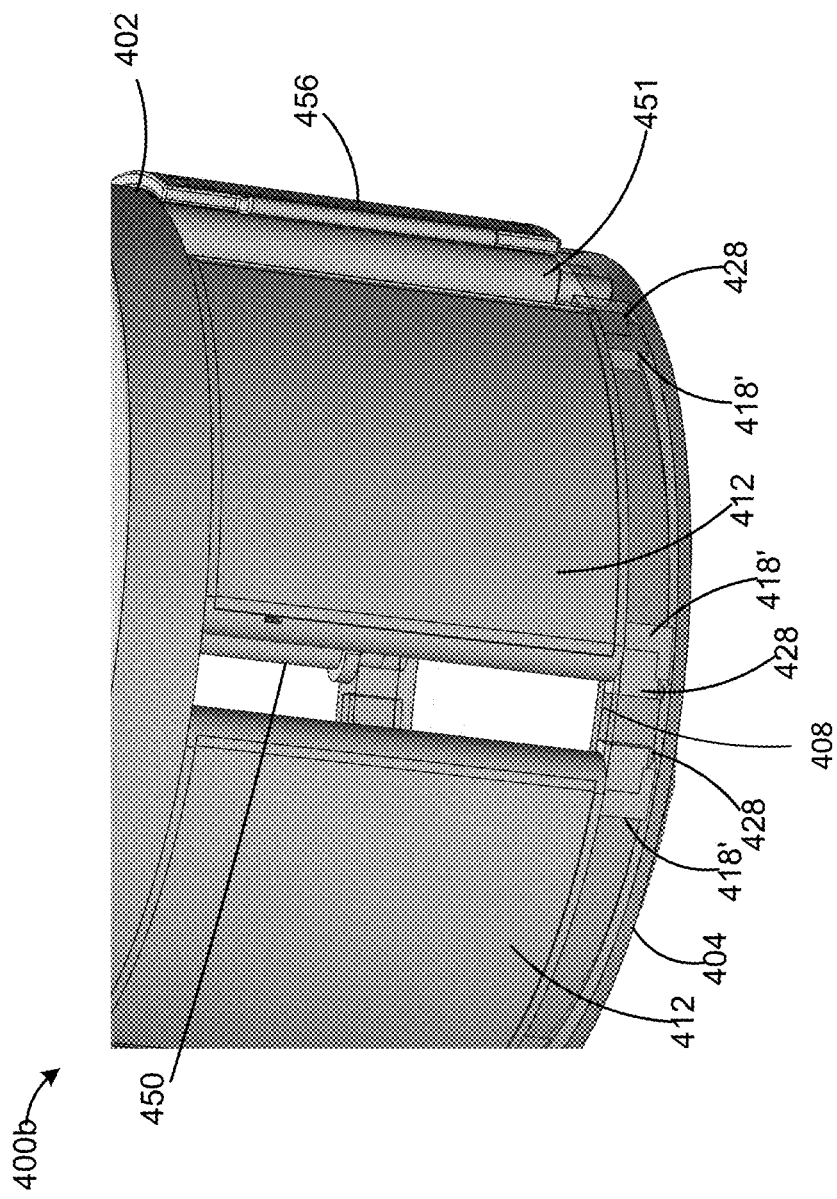
FIG. 4B illustrates another example embodiment of a cuff unit that has adjustable panels and adjustable electrodes.
Figure 4E:
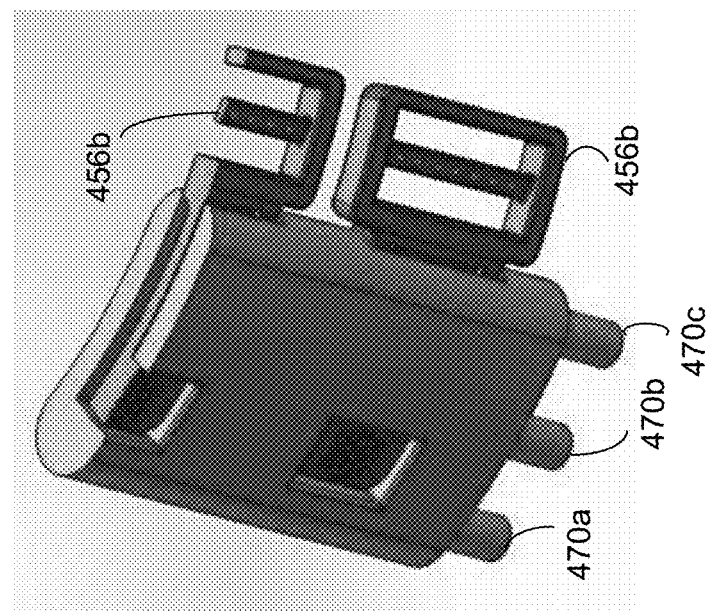
FIG. 4E illustrates a portion of a support panel that may be used with a cuff unit.

Referring now to FIG. 4B, shown therein is another example embodiment of a cuff unit 400b that has adjustable panels and adjustable electrodes. The cuff unit 400b is similar to the cuff unit 400a except that the cuff unit 400b includes stub connector portions 428 along the interior of the lower track portion 408. Similarly, stub connector portions 428 are also provided along the interior of the upper track portion provided on the inner edge of the first peripheral member 402

(not shown). The second end portions 418' of the panels 412 are shown with a hook or a flange configuration that is engageable with the stub connector portions 428. In some cases, the panel 412 can be translated along the track of the cuff unit 400b without any stub connector portions 428 being in place. Once the panels 412 have been properly aligned for the user 180, the stub connector portions 428 can be secured in the upper track portion 410 and the lower track portion 408, for example using an adhesive or other fastener, or structures such 428. The stub connector portions 428 can be secured in the upper and lower track portions 410 and 408 in a mating relationship with the first and second end portions 416' (not shown) and 418' of the panel 412 to maintain the panel 412 in the desired alignment.

Referring now to FIG. 4C, shown therein is an example embodiment of other fasteners in a cuff unit 400c. The cuff unit 400c is similar to the cuff units 400a and the cuff unit 400c is shown with having circular electrodes 438 (only one of which is shown) mounted to the corresponding panels 412. In alternative embodiments, the electrodes 438 may be rectangular, square or any other shape that is suitable for applying the stimulation signals to the user 180.

The cuff unit 400c may also include a port 444 for coupling the cuff unit 400c to a computer or a charging station. In some embodiments, the port 444 can be a USB connector port. The port 444 can be positioned at various points along the frame of the cuff unit 400c such that it is coupled to the battery module and the stimulation module. For example, the port 444 can be provided on the underside of the second peripheral member 404 as shown in FIG. 4C where the control panel 413 is located. In some embodiments, the port 444 may be located at the side of a panel that houses both the control circuitry and the stimulation module.

Alternative fasteners are also shown in FIG. 4C. In particular, a pair of male fastener members 456b are shown matingly engaged with corresponding sockets provided in support panel 451'. The male fastener members 456b are shown attached to the end of fastener straps 468 that are attached to the frame of the cuff unit 400c using the support posts 452 and the sub-panels 450t, 450m and 450b provided by the support panel 450.

Figure 4D:
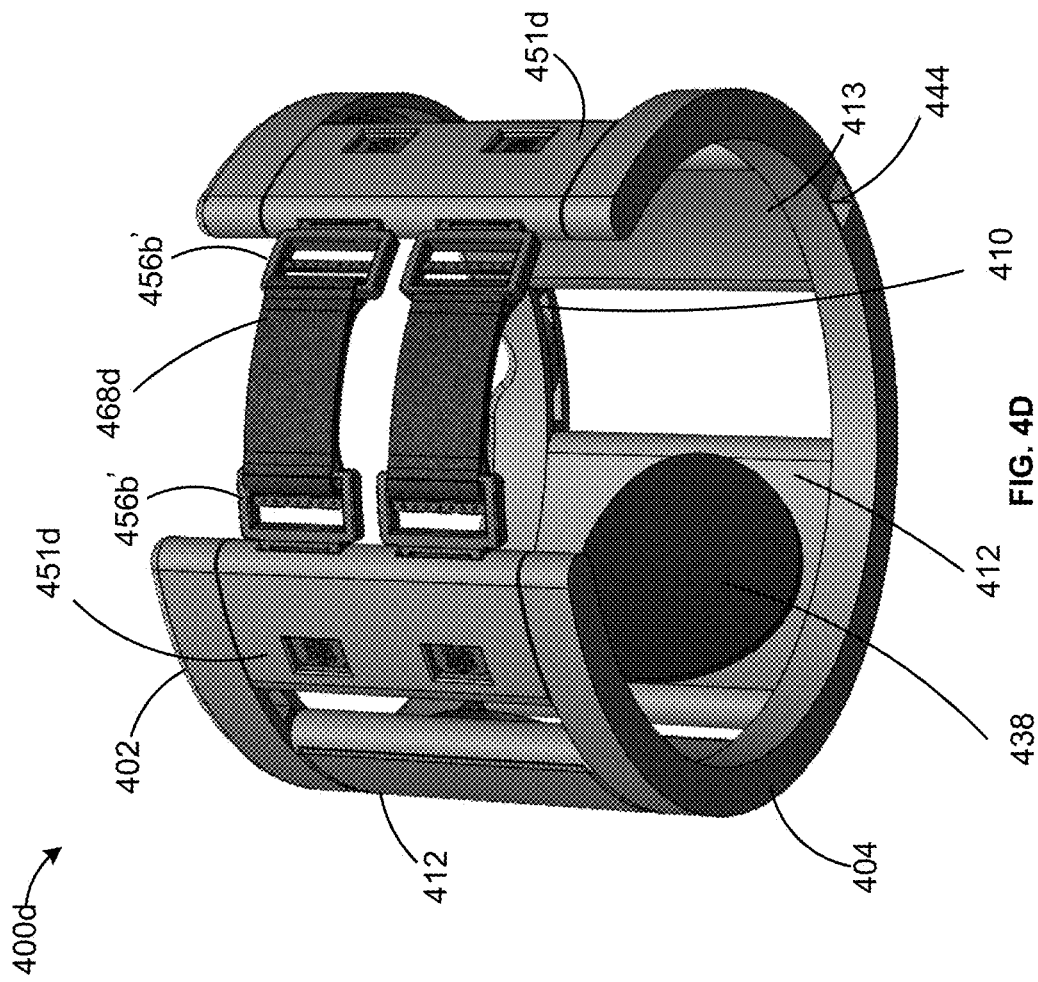
FIG. 4D illustrates another example embodiment of fasteners used in another cuff unit.

Referring now to FIG. 4D, shown therein is another example embodiment of the cuff unit 400d where fastener straps 468d are provided with male fastener members 456b' at both ends. The fastener straps 468d can be used to securably fasten the cuff unit 400d around the leg of a user. In this embodiment, the cuff unit 400d is provided with two support panels 451d that both have sockets to engage with the male fastener members 456b'. In some cases, the fastener straps 468d may also be adjustable to fasten and loosen the cuff unit 400d for the user 180. For example, one end of the straps 468d can be held in a fixed position at the fastener members 456b' and the other end of the straps 468d may be looped around the corresponding fasteners 456b' such that the length of the straps 468d may be adjusted so that the cuff unit 400d is comfortably maintained in place on the leg of the user 180 during use. Alternatively, the straps 468d may be elastic and are held fixedly in place at both sets of fasteners 456b' and the straps 468d may be stretched by a person placing the cuff unit 400d on the user 180 so that the cuff unit 400d can be placed on the leg of the user 180 and then the person releases the straps 468d so that they snugly fit around the leg of the user 180.

Referring now to FIG. 4E, shown therein is a portion of a support panel 451' that may be used with the some of the cuff units described herein. FIG. 4E illustrates how to lock and release the buckles 456b' from the support panels 451d. There is a convenient benefit to the user 180 of being able to lock and release the cuff unit from the leg of the user 180 at any end of the fastener straps 468d as elements 451d and 456b can be placed at both ends of the fastener strap 468d. This makes it easier for the user 180 to mount and remove the cuff unit from their leg. For example, one end of the buckles 456b (or 456b') having the tongue may be inserted into the support panel 451d (or 451') and the tongue of the buckle 456b may be locked by a corresponding female member of the support panel 451d. The vanes on the both sides of the tongue of the buckle 456b will force the tongue elastic to the window of the support panel 451 thereby releasably locking the buckle 456b into the support panel 451d. The tongue of the buckle 456b may be pulled out when desired when the user presses the tongue down. This description also applies to buckles 456b' and support panels 451' and 451". FIG. 4J shows the tongue more clearly for the support panel 451" that is similar to support panel 451' with the exception of having different shaped buckles 456b'.

Referring now to FIG. 4F, shown therein is another example embodiment of a cuff unit 400f having a male fastener member 456f that can be used to securely fasten the cuff unit 400f to the user 180. The male fastener member 456f is a square shaped buckle that can engage with a socket provided by support panel 451. A female fastener member 467 will lock into the male faster member 456f when the female fastener member 467 is pressed forward to the male fastener member 456f by the elastic character of tabs 453 and 453'. The female fastener member 467 may be released from the locked position when it is pulled from the male fastener member 456f when a pull force is applied thereto which is larger than the friction force provided by the tabs 453 and 453'. The male fastener member 456f is attached to two fastener straps 468 that are attached to the frame of the cuff unit 400f at the support post 452 provided by the support panel 450. The straps 468 of the cuff unit 400f may be adjusted to hold the cuff unit 400f in place on the leg of the user 180 as was described for the cuff unit 400d.

Figure 4G:
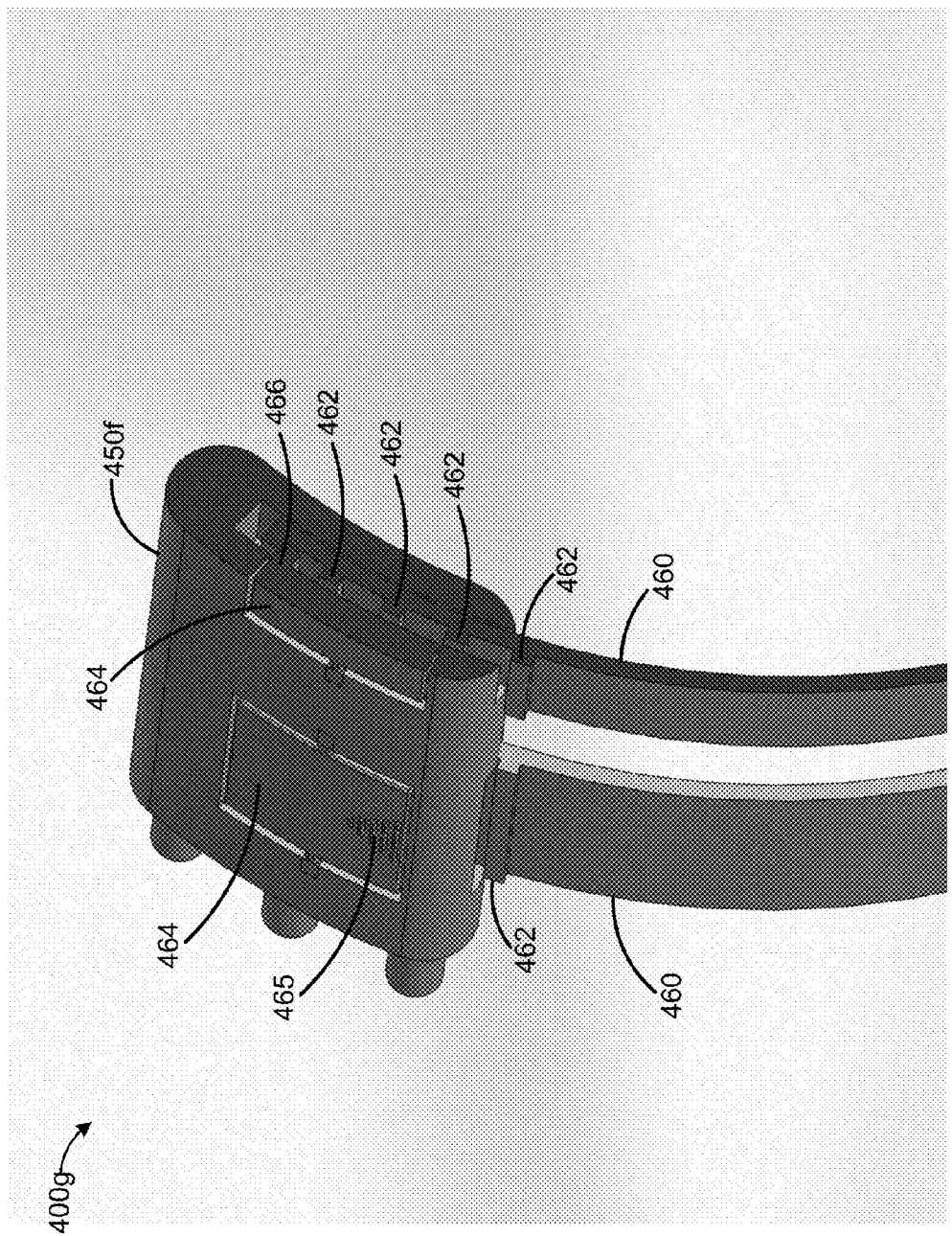
FIG. 4G illustrates another example embodiment of fasteners used with another cuff unit.

Referring now to FIG. 4G, shown therein is an enlarged view of an alternative ribbed belt fastener 460 engaged with a socket provided in a support panel 450f that can be used with a cuff unit such as cuff unit 400h. Each of the ribbed belt fasteners 460 includes a plurality of fastening teeth 462. The socket provided in the support panel 450f includes a tongue 464 with a locking tooth 466 that is engageable with the fastening teeth 462. When the user 180 wishes to fasten or loosen the cuff unit 400f, they can press a tongue release 465 that functions as a lever to raise the locking tooth 466 such that the position of the ribbed belt fastener 460 can be adjusted. When the user 180 releases the tongue release 465, the locking tooth 464 engages with the fastening teeth 462 such that the ribbed belt fastener 460 is secured in place. In alternative embodiments, the ribbed belt fasteners 460 may include fastening teeth 462 throughout their length. In other embodiments, the ribbed belt fasteners 460 may include a portion substantially devoid of fastening teeth 462, as is shown in FIG. 4G.

Referring now to FIG. 4H, shown therein is another example embodiment of a cuff unit 400h. The cuff unit 400h is somewhat similar to the cuff unit 400f except that the cuff unit 400h uses the fastener straps 400g. The cuff unit 400h has a first peripheral member 402 and a substantially parallel second peripheral member 404. The cuff unit 400h includes a plurality of panels 412 and 413 extending from the first peripheral member 402 to the second peripheral member 404. The cuff unit 400h includes a track defined by an upper track portion 410 and a lower track portion (not shown) provided on the inner edge of the second peripheral member 404.

The cuff unit 400h also includes a battery module including at least one battery that is contained within one or more of the panels 412. The cuff unit 400h also includes a stimulation module that may be contained in control panel 413. The stimulation module is coupled to the battery module and is operable to generate stimulation signal to be applied to the user 180. The cuff unit 400h includes a USB connector port 444 that may allow the user 180 to connect the stimulation module to an external system or to recharge the batteries in the battery module.

The cuff unit 400h also includes at least two contact members. Each contact member is associated with one of the panels 412. The contacts members may include a conductive member disposed on a corresponding panel 412 and an electrode 438 coupled to the conductive member and mounted on the panel 412. It may be possible for more than one electrode to be on the same panel in some embodiments. There may be embodiments in which the conductive members and electrodes are not on panels that house the stimulation module.

The cuff unit 400h also includes a pair of ribbed belt fasteners 460' having a plurality of ribs or teeth. The ribbed belt fasteners are attached to the cuff unit 400h at both ends using sockets provided by the support panels 451h. The user 180 of the cuff unit 400h can fasten or loosen the ribbed belt fasteners 460' using the tongues 464' to adjust the fit of the cuff unit 500. The ribbed belt fasteners 460' and the tongues 464' operate in a similar manner as for the embodiment shown in FIG. 4G except that the ribbed belt fasteners 460' are adjustable at both support panels 451. Otherwise, the cuff unit 400h can be provided with various similar structural features as the cuff units 140, 200, 300, 300', 400a-400d, and 400f.

Figure 4I:
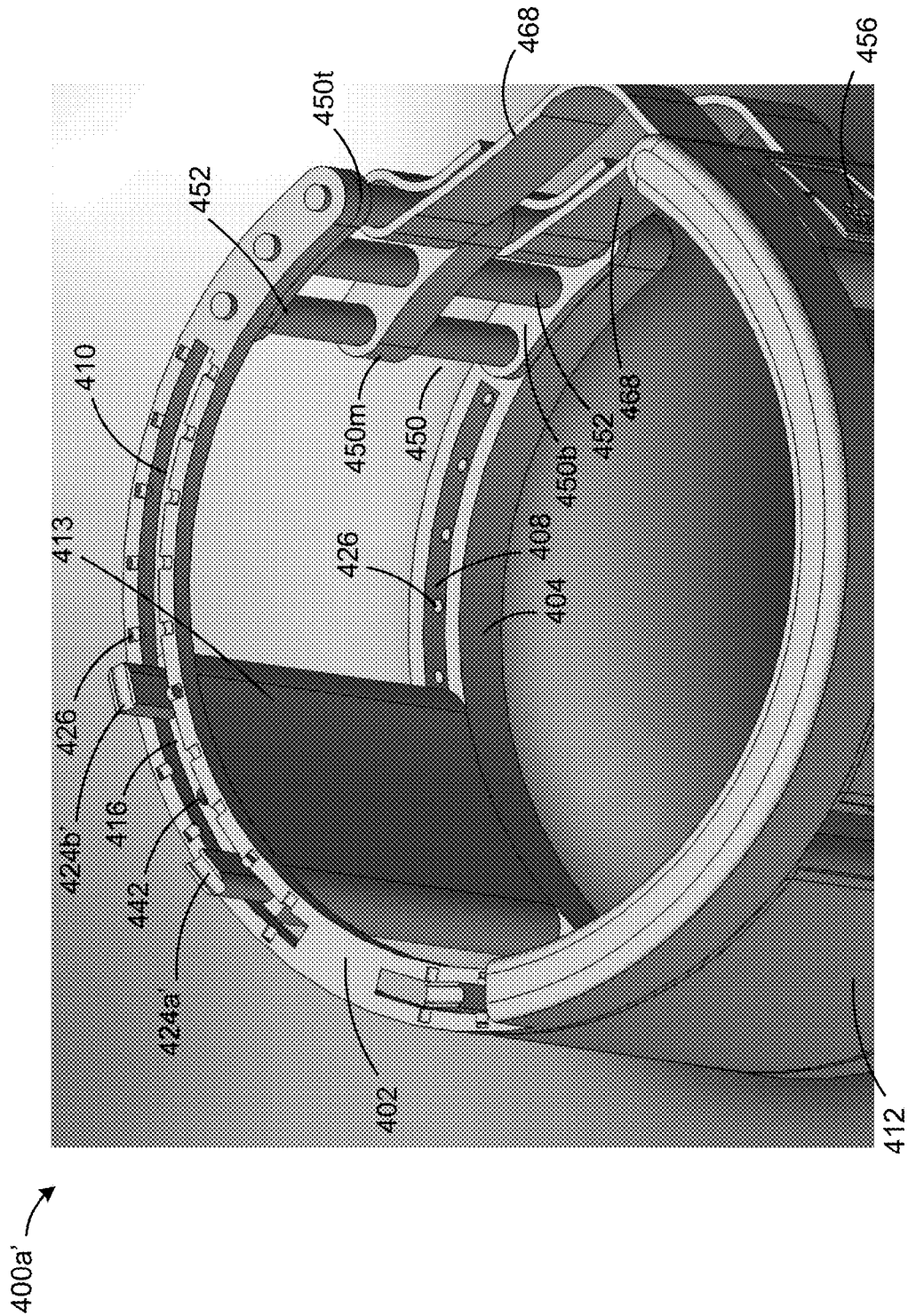
FIG. 4I illustrates an example of an alternative embodiment of the cuff unit of FIG. 4A that has adjustable panels and adjustable electrodes.
Figure 4J:
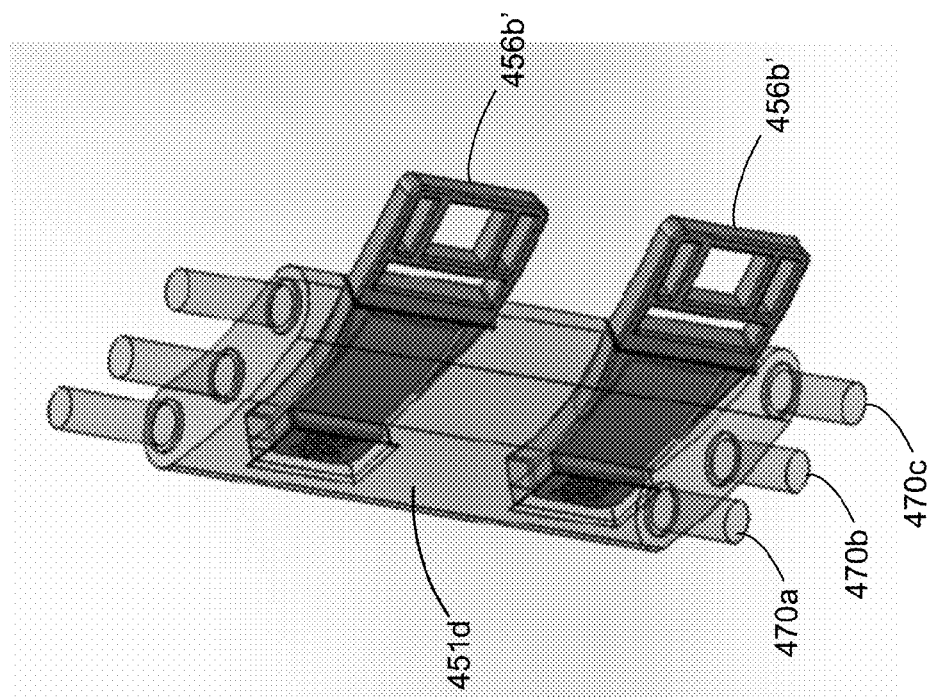
FIG. 4J illustrates an example of an alternative embodiment of the support panel of FIG. 4E that may be used with a cuff unit.

Referring now to FIG. 4I, shown therein is an example of an alternative embodiment of a cuff unit 400a' that has adjustable panels and adjustable electrodes. The cuff unit 400a' is similar to the cuff unit 400a shown in FIG. 4A. However, the cuff unit 400a'; comprises panel 413 having first end portions 424a' and 424b' that protrude through the groove of the upper track portion 410 and have posts that protrude generally horizontally and engage corresponding connector portions 426. Although not shown, the other end of panel 413 may have similar structure to engage the lower peripheral member and panel 412 may have similar structure as the ends of panel 413. Accordingly, the positions of the panels 412 and 413 may be adjusted before they are fixed in place so that there is an adjustable gap between the panels 412 and 413 as well as between these panels and the support panels 450 and 451.

Referring now to FIG. 4J, shown therein is an example of an alternative embodiment of the support panel 451" that may be used with a cuff unit. The support panel 451" is similar to the cuff unit 451'. However, different shaped buckles 456b' are used. The buckles 456b' operate similarly as buckles 456b as was described in relation to FIG. 4E.

Figure 5A:
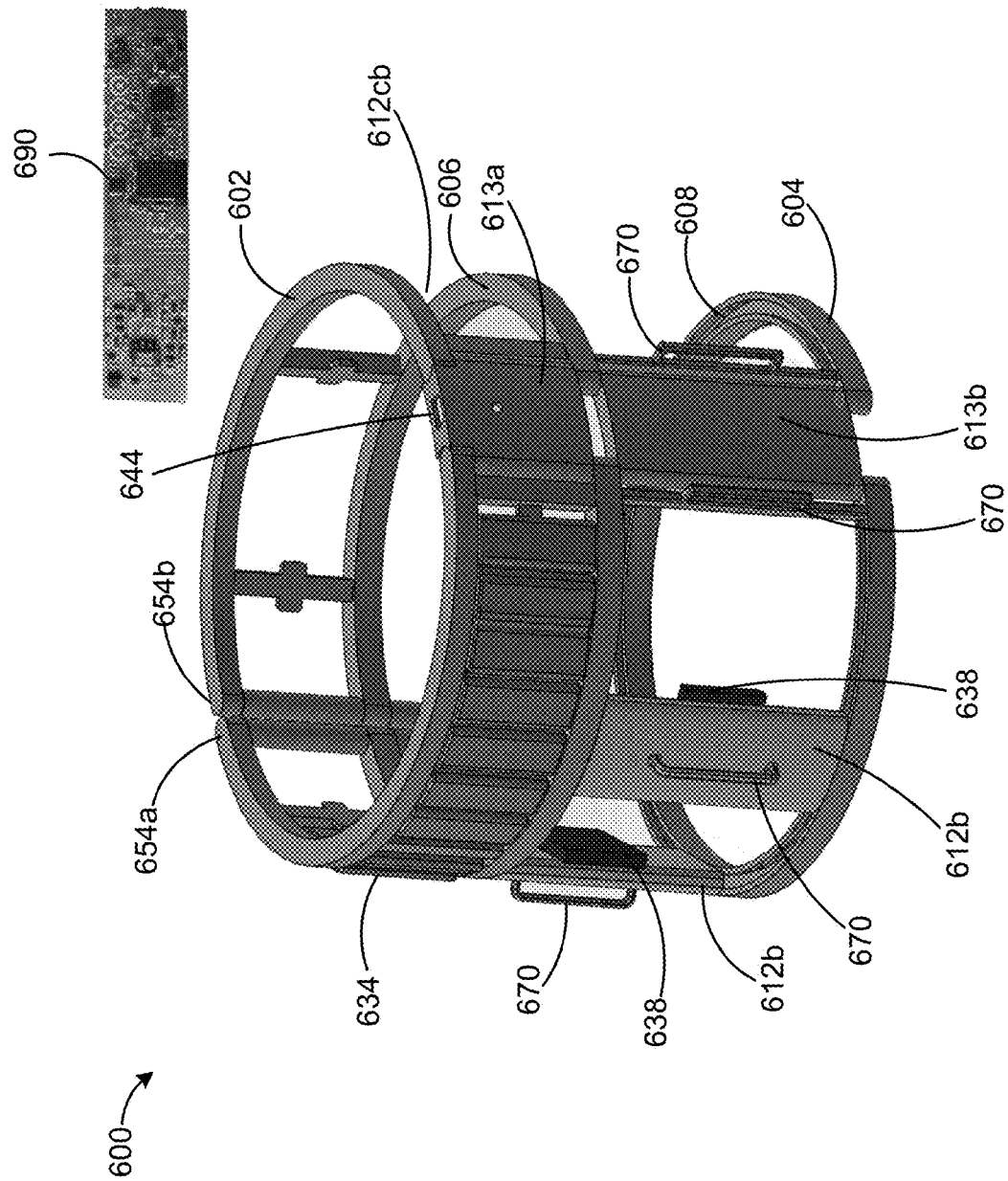
FIG. 5A illustrates a partial transparent view of another example embodiment of a cuff unit with a different circuit integration layout.
Figure 5B:
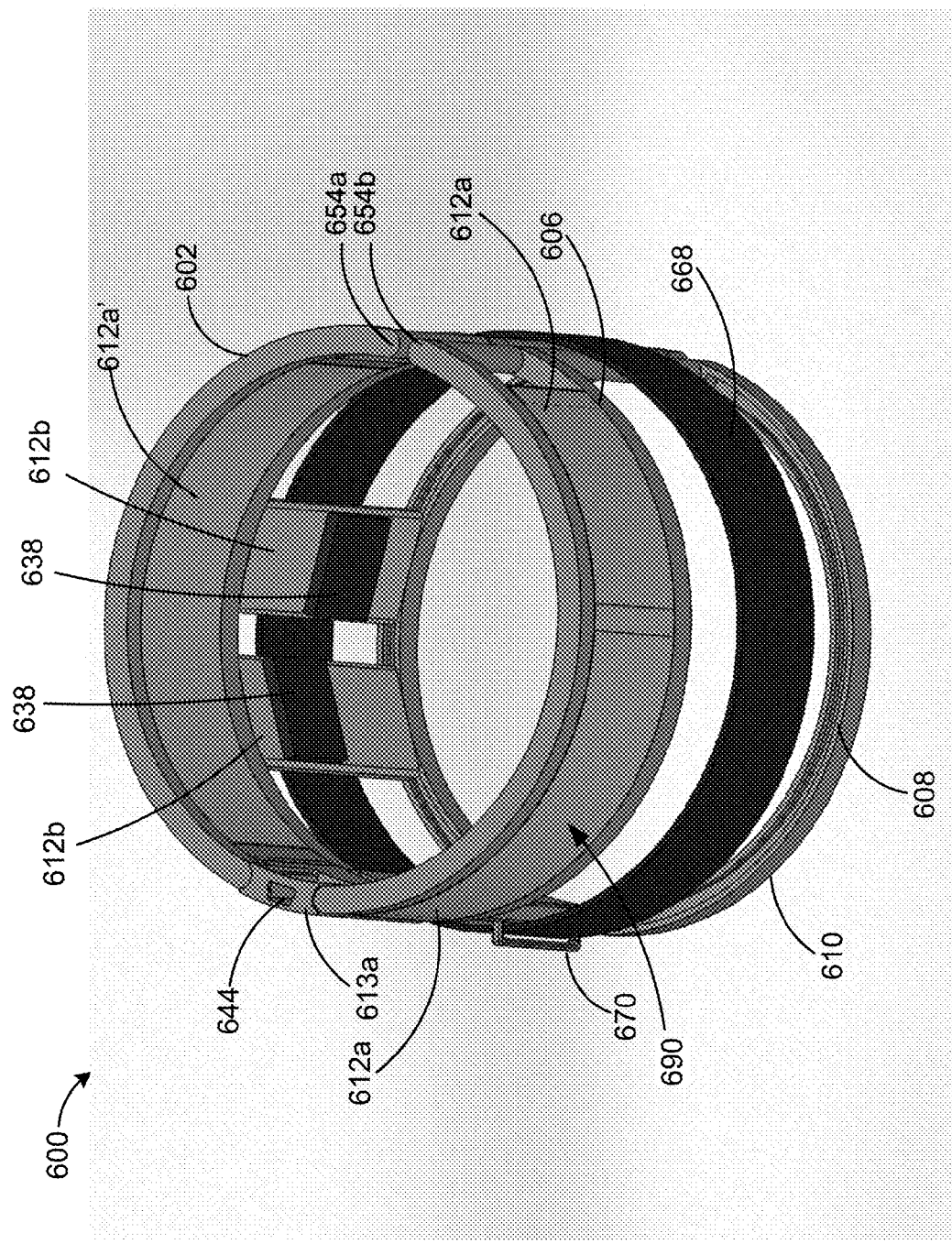
FIG. 5B illustrates the cuff unit of FIG. 5A with panel covers and a belt fastener.

Referring now to FIGS. 5A and 5B, shown therein is another example embodiment of a cuff unit 600. FIG. 5A shows a view of the cuff unit 600 without panel covers and a belt fastener and having a different circuit integration layout. FIG. 5B shows the cuff unit 600 with the panel covers and the belt fastener. The cuff unit 600 includes a first peripheral member 602, a second peripheral member 604 and a third peripheral member 606. The cuff unit 600 also includes a stimulation module and a battery module having one or more batteries 634. The stimulation module and battery module for the cuff unit 600 can have the same general properties as the stimulation module and battery modules of the previous cuff units.

The cuff unit 600 can also include a track that is defined by a lower track portion 608 provided on the inner edge of the second peripheral member 604 and an upper track portion (not shown) provided on the inner edge of the third peripheral member 606 facing the lower track portion. The cuff unit 600 may also include a first set of panels 612a and a second set of panels 612b. The panels 612a extend from the first peripheral member 604 to the third peripheral member 606 and the panels 612b extend from the third peripheral member 602 to the second peripheral member 606. The second set of panels 612b may be used to mount the electrodes.

The stimulation module and the batteries 634 of the battery module for the cuff unit 600 may be contained in one or more of the panels 612a located between the first peripheral member 602 and the third peripheral member 606. The stimulation module may be provided as a flexible PCB 690, which may be mounted between the peripheral members 602 and 606 in the space 612cb (see FIG. 5A for example) and housed within the panel 612a'.

The cuff unit 600 also includes at least two contact members, each contact member being associated with one of the panels 612b. The contact members generally include a conductive member disposed on the inner surface of one of the panels 612b that faces the skin of the user 180 during use. Each contact member also generally includes an electrode 638 that is coupled to the conductive member and mounted on the associated panel 612b. In this example embodiment, the electrodes 638 are shown having a rectangular shape but other shapes can be used in other embodiments.

The electrode 638 can be translated with respect to the panel 612b on which it is mounted using various mechanisms such as those that were described with respect to previous cuff units described in accordance with the teachings herein, such as the cuff unit 300. It should be noted that the translation mechanisms for the electrodes of cuff unit 300 may be used for the other cuff unit embodiments described herein. As was described for the other cuff units, the electrodes 638 may be adjusted initially to properly align the electrodes 638 with the nerve(s) of the user requiring stimulation and then these electrodes 638 may be adhesively secured in place for use thereafter by the user 180.

The panels 612b in the second set of panels may be movable with respect to the frame of the cuff unit 600. In some cases, the panels 612b can initially be moved with respect to the frame of the cuff unit 600 and then secured in place using various methods, such as the various methods that were previously described for securing the moveable panels for the other cuff units described herein. Accordingly, the panels 612b may have first end portions and second end portions that are engageable with the upper track portion and the lower track portion 608, respectively. The first and second end portions may take various forms and may include various connector portions such as the various connector portions described herein for the other cuff embodiments. In some cases, the panels 612b may be re-adjustably movable with respect to the frame of the cuff unit 600 over time. This can allow the panels to be re-adjusted if the shape of the legs of the user 180 changes over time such that the contact members require re-positioning.

The cuff unit 600 also includes control panels 613a and 613b. The support panel 613a may be used to house an interface for a USB connector port 644. The USB connector port 644 may be provided on the top side of the support panel 613a as shown. The USB connector port 644 may also be provided in various other locations such that the USB connector port 644 may be coupled to at least one of the battery module and the stimulation module using wires that are typically contained entirely within the frame of the cuff unit 600. Accordingly, all of the controller functions including indicators, operation buttons, charging port and the like may be distributed between control panels 613a and 613b, port 644, and circuit board 690.

The frame of the cuff unit 600 is generally structured so that it takes the form of a clasp having ends 654a and 654b which can separate from one another when the cuff unit 600 is placed on a leg having a circumference that is greater than the circumference of the cuff unit 600 when not in use. In this case, the ends 654a and 654b of the cuff unit 600 move away from each other and the cuff unit forms a friction fit with the leg of the user 180.

The cuff unit 600 may further comprise a plurality of fastener supports 670 arranged around the exterior of the frame of the cuff unit 600. In this example, the fastener supports 670 are disposed on the panels 612b and on either side of the control panel 613b. The fastener supports 670 can be used to support a fastener strap 668, as is shown in FIG. 5B, that is used to apply tension to the exterior of the cuff unit 600 when it is secured around a leg of the user 180. The fastener strap 668 is typically elasticized so that it can expand when the cuff unit 600 is mounted on a leg of the user 180 having a greater circumference then the circumference of the cuff unit 600 when it is not in use.

In some embodiments, the panels 613a and 613b may mechanically operate as hinges. The fastener supports 670 and the upper portion of the cuff unit 600 between peripheral members 602 and 606 forms the frame of the cuff unit 600. This allows the cuff unit 600 to be opened and closed between ends 654a and 654b so that the cuff unit may be placed onto or removed from the leg of the user 180.

Figure 6A:
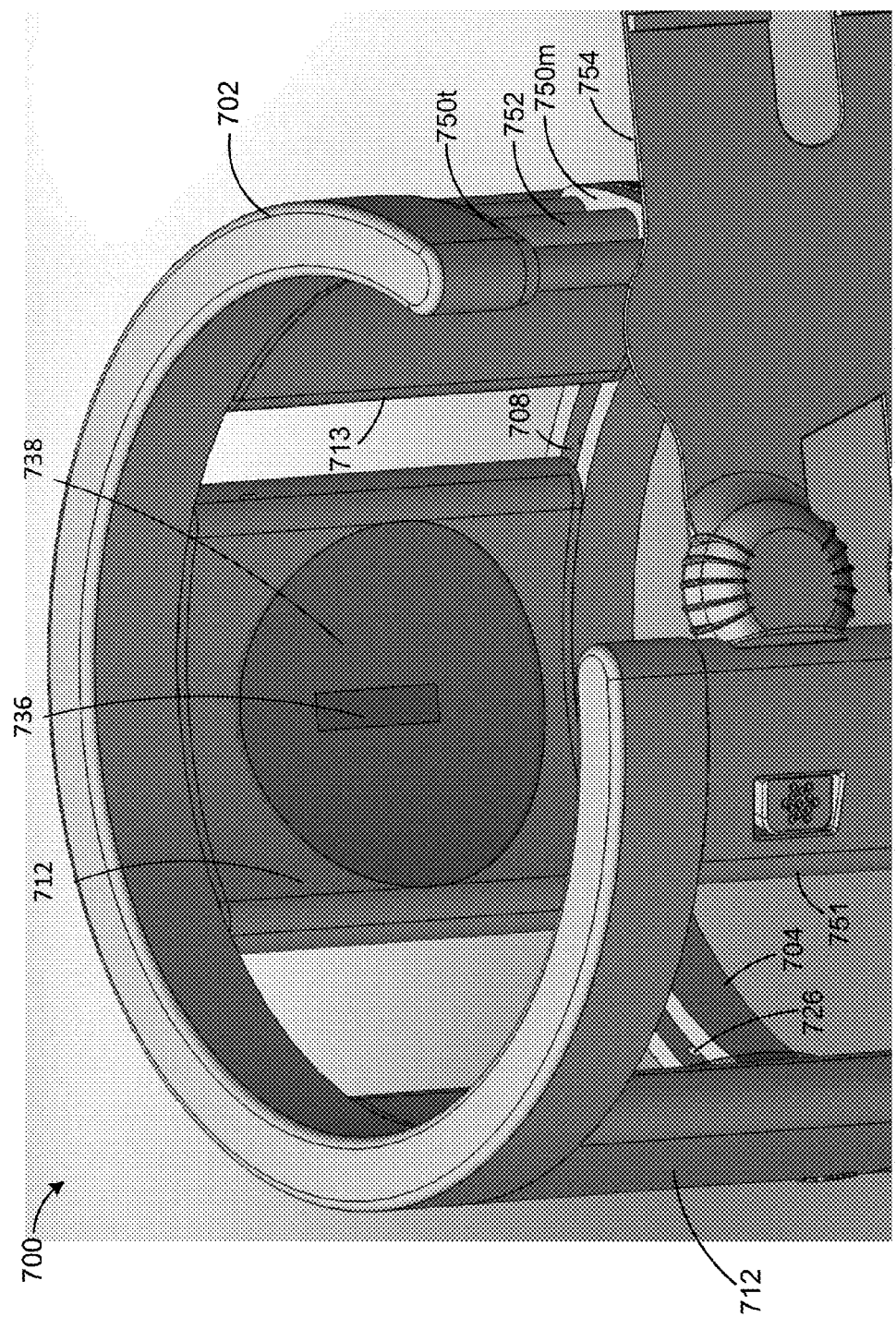
FIG. 6A illustrates another example embodiment of a cuff unit.

Referring now to FIG. 6A, shown there is another example embodiment of a cuff unit 700. The cuff unit 700 is somewhat similar to the cuff units 140, 200, 300, 300', 400a-400d, 400f, 500 and 600. Accordingly, the cuff unit 700 comprises a first peripheral member 702, a second peripheral member 704 and a plurality of panels 712 and 713. The cuff unit 700 also includes a fastener 754 that has a ribbed belt as well as a male fastener member that can engage with a socket provided by support panel 751, which is shown in more detail in FIGS. 6B and 6C.

The cuff unit 700 has a track defined by an upper track portion provided on the inner edge of the first peripheral member 702 and a lower track portion 708 provided on the inner edge of the second peripheral member 704. The track includes apertures 726 that are adaptable to receive corresponding tab or post connector portions that may be provided on the first and second end portions of panels 712 and 713. The cuff unit 700 also includes a stimulation module, a battery module and at least two contact members that can be provided in various configurations as described above.

FIG. 6A illustrates the relationship between a conductive member 736 of a contact member and an electrode 738 in accordance with an example embodiment. Please note that the electrode 738 is shown as being transparent in this view. The conductive member 736 is provided as a vertical strip of conductive material. The conductive member 736 couples the electrode 738 to the stimulation module such that the electrode 738 is operable to apply the stimulation signals generated by the stimulation module to the user.

The electrode 738 can be translated with respect to the panel 712 to properly align the electrode to apply the stimulation signals to nerve(s) of the user 180 that require stimulation. The conductive member 736 is provided with a sufficient length to ensure that regardless of the position of the electrode 738 it will remain in electrical communication with the stimulation module. Once the electrode 738 has been properly aligned, it can be secured in place using any suitable means such as an electrically conductive adhesive.

Figure 6B:
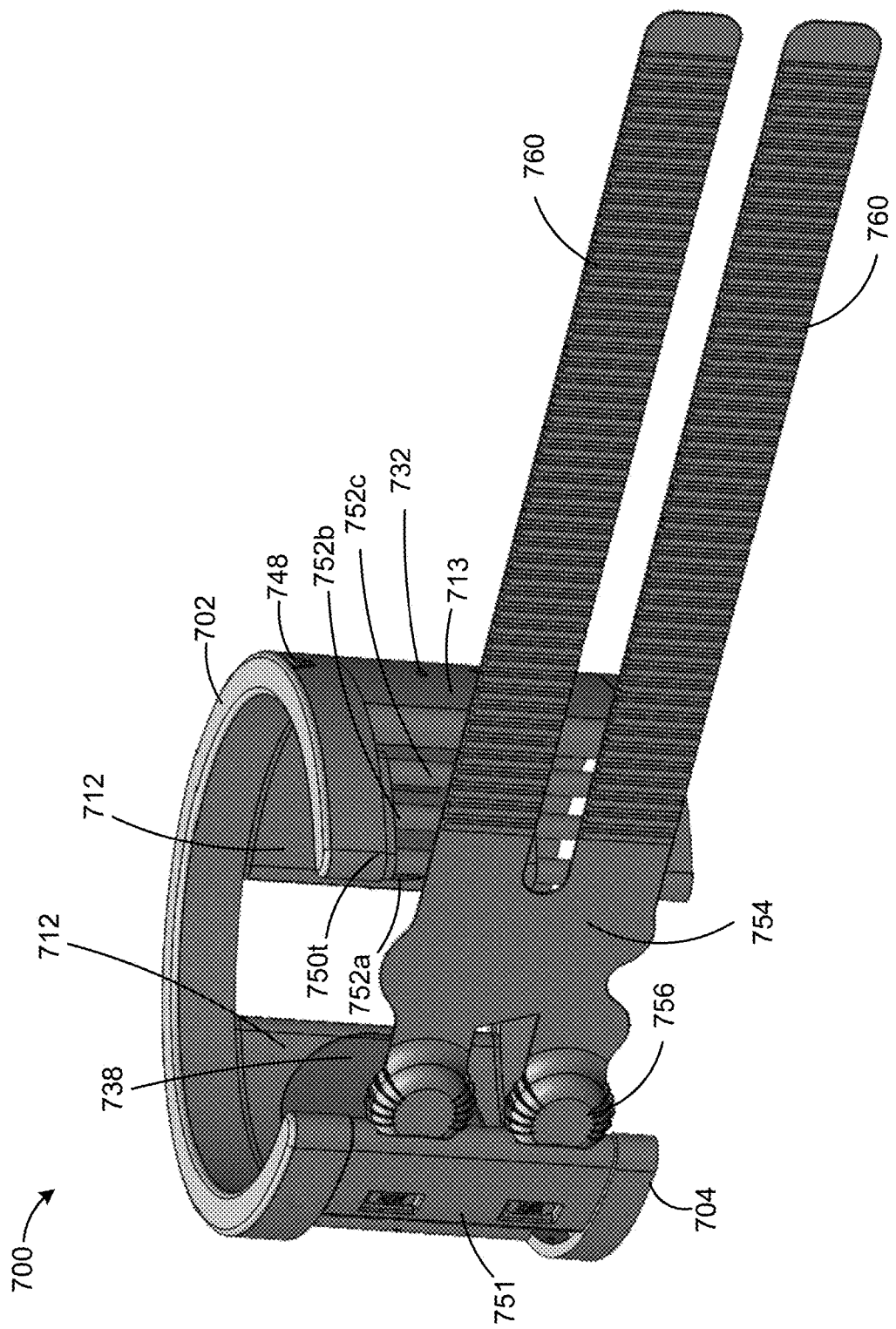
FIG. 6B is a view of the cuff unit of FIG. 6A in an open configuration.

Referring now to FIG. 6B, shown therein is a view of the cuff unit of FIG. 6A in an open configuration. The fastener 754 includes a pair of ribbed belt fasteners 760 and a pair of male fastener members 756. The cuff unit 700 also includes a support panel 750 along with a first support post 752a, a second support post 752b and a third support post 752c. The male fastener members 756 are engageable with sockets provided by the support panel 751. The ribbed belt fasteners 760 can function as self-locking fasteners so that the user 180 can entwine the ribbed belt fasteners 760 around the first support post 752a, the second support post 752b and the third support post 752c such that the fastening teeth 762 interlock as is shown in FIG. 6C.

The cuff unit 700 also includes an alignment marker 748 that can be used to properly position the cuff unit 700 for use, such as by aligning the alignment marker 748 with a knee cap of the user 180. Alternative alignment markers can also be used with the cuff unit 700 such as an alignment notch 246 or any other suitable alignment indicators. The cuff unit 700 also includes an indicator light 732 and control buttons 730.

Figure 6C:
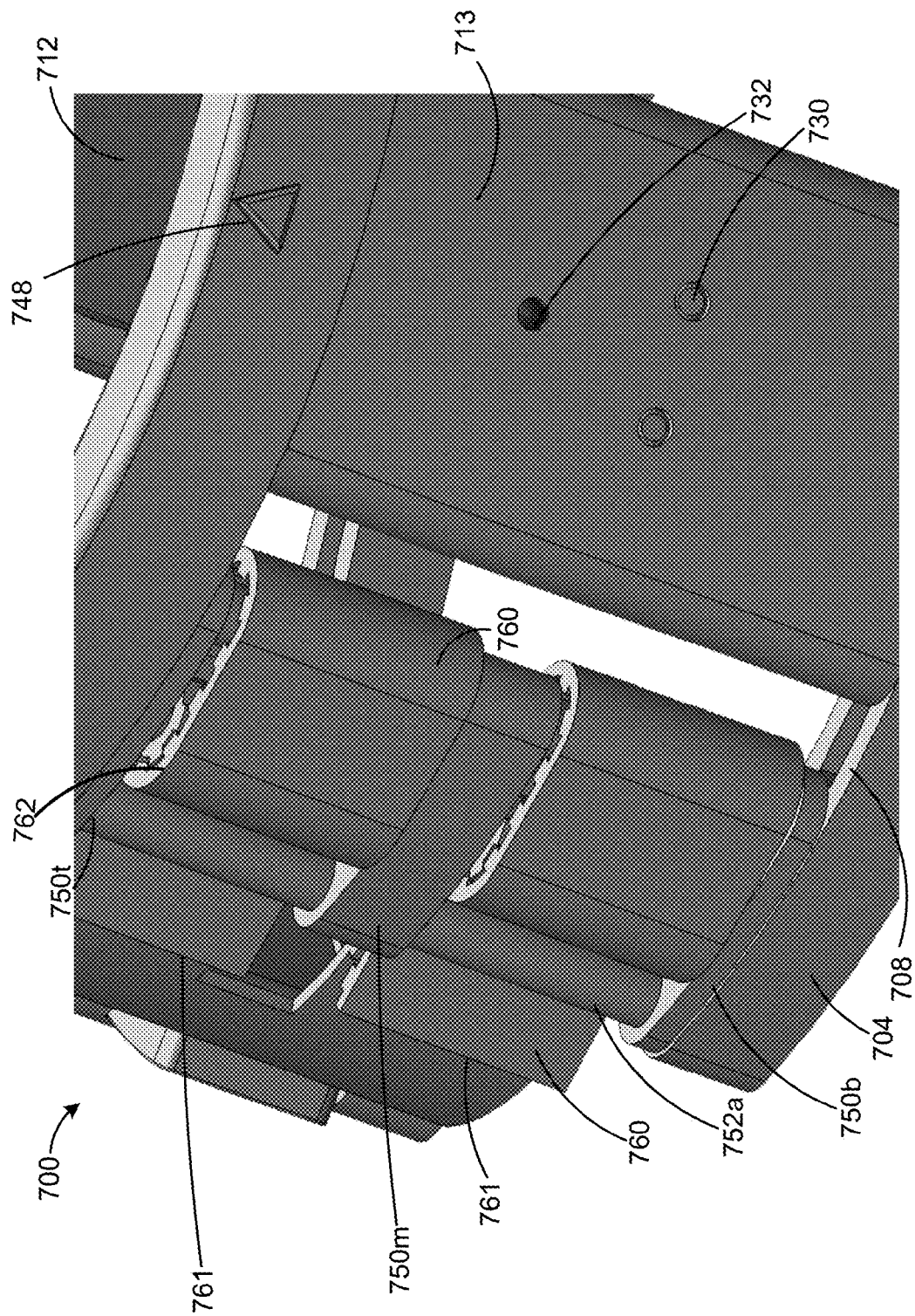
FIG. 6C is a view of the cuff unit of FIG. 6A in a closed configuration.

Referring now to FIG. 6C, shown therein is a view of the cuff unit 700 in a closed configuration such as when the cuff unit 700 is worn by the user 180. The ribbed belt fastener 760 has been entwined around the first support post 752a, the second support post 752b and the third support post 752c such that the fastening teeth 762 have engaged with one another and secured the ribbed belt fastener 760 in place.

An example configuration for securing the ribbed belt fastener 760 in a self-locking arrangement will now be described. However, it should be understood that various other suitable configurations may also be used. As shown in FIG. 6C, the first end 761 of each ribbed belt fastener 760 initially passes the first support post 752a on the inner surface of the frame of the cuff unit 700 with the fastening teeth 762 facing outward from the frame. The first end 761 is then wrapped around the outer surface of the second support post 752b and passes the third support post 752c on the inner surface of the cuff unit 700 with the fastening teeth 762 facing outward.

The ribbed belt fastener 760 is then looped around the third support post 752c with the fastening teeth 762 in contact with the third support post 752c. The ribbed belt fastener 760 then passes the second support post 752b on the outer surface of the cuff unit 700 with the fastening teeth 762 facing inward. The ribbed belt fastener 760 is then passed by an inner surface of the first support post 752a with the fastening teeth 762 facing inward. The first end 761 of the ribbed belt fasteners 760 can then be pulled to the desired position to secure the ribbed belt fasteners in place.

As the fastening teeth 762 pass the second support post 752b and face inward, they engage with the outward facing fastening teeth 562 that were positioned when the ribbed belt fastener 760 initially passed the outer surface of the second support post 752b. The tension provided by the ribbed belt fastener 760 will then cause the engaged fastening teeth 762 to act as a self-locking mechanism that secures the cuff unit 700 on the user 180. If desired, the user 180 can further tighten the cuff unit 700 by pulling on the first end 761 of the ribbed belt fastener 760.

Figure 6D:
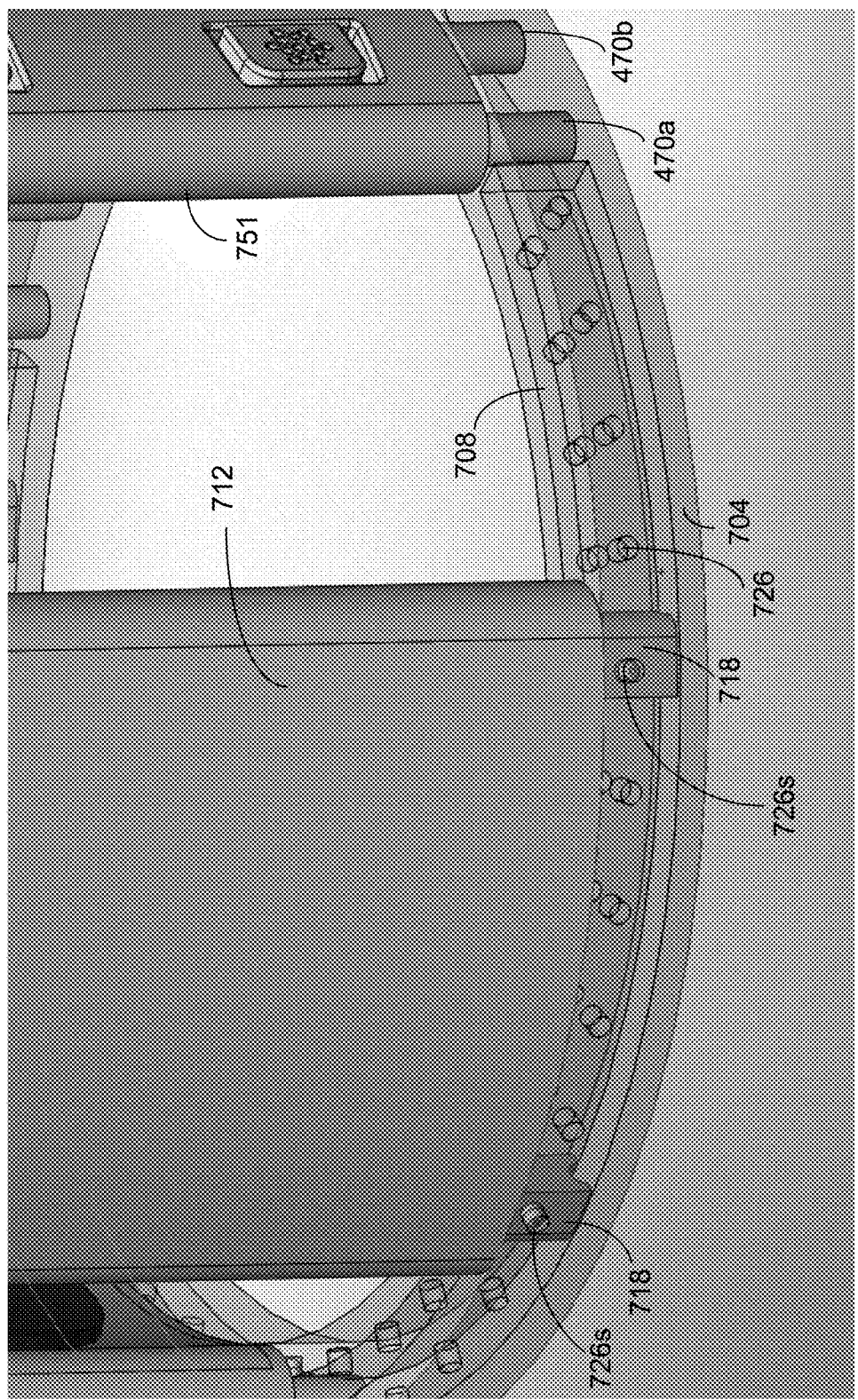
FIG. 6D is a magnified view showing the interaction between a panel and a peripheral member of the cuff unit of FIG. 6A.

Referring now to FIG. 6D, shown therein is a magnified view showing the interaction between a panel 712 and a peripheral member 704 of the cuff unit 700. The peripheral member 704 comprises a track 708 and a plurality of connector portions 726, which in this example are apertures. The panel 712 has second end portions 718 with connectors 726s, which in this example are studs or posts. The part of the second end portions 718 below the connectors 726s are moved along the tack 708 until the panel 712 is at the desired location. At this point, the panel 712 may be pushed downwards so that the connectors 726s of the second end portions 718 engage the connector portions 726 of the peripheral member 704. At this point, an adhesive may also be used to further maintain the panel 712 in place during use.

Referring now to FIG. 7, shown therein is an example of two ways of aligning a cuff unit on the user 180. In this example, the cuff unit 400 is worn on the right leg 180a of the user 180 and the cuff unit 700 is worn on the left leg 180b of the user 180. The alignment notch 446 of the cuff unit 400 may be used to align the cuff unit 400 with the knee on the right leg 180a of the user 180. The alignment marker 748 of the cuff unit 700 may be used to align the cuff unit 700 with the knee on the left leg 180b of the user 180. The cuff units 400 and 700 are releasably secured in place as was described previously. It should be understood that there may be embodiments without an alignment indicator in alternative embodiments. It should also be understood that in alternative embodiments other fastening mechanisms may be used.

The indicator lights 432 and 732 and the control buttons 430 and 730 can be located such that they will be facing outward from the leg of the user 180 when the cuff units 400 and 700 are worn. This positions of the indicator lights 432 and 732 and the control buttons 430 and 730 are convenient so that the user is able to quickly and easily assess the status of the cuff units 400 and 700 and control the cuff units 400 and 700. For example, the user 180 can turn the cuff units 400 and 700 on by pressing a reset button. Also, the user 180 may select the mode operation (e.g. training or working) by pressing the mode button for different time durations where the different time durations may be associated with different modes of operation. For example, the mode button may be depressed for a long time (e.g. more than 3 seconds) to enter turn off mode. The indicator and a sound (e.g. from a buzzer) of the cuff units 400 and 700 may be used to indicate the status of the operating mode of the cuff units 400 and 700.

While the cuff units 400 and 700 have been shown mounted on the legs 180a and 180b of the user 180, it should be understood that each of the cuff units described herein may be modified to be worn on other body parts of the user 180. For example, one of the cuff units described herein can be modified to be worn on an arm of the user 180.

Referring now to FIGS. 8A to 8G, shown therein is another example embodiment of a cuff 800 unit having adjustable panels 812 and 813. The cuff unit 800 is similar to the cuff unit 700. Accordingly, similar reference numbers are associated with similar elements in these two cuff units such as ribbed belt fastener 760 and 860, for example. The cuff unit 800 comprises a first peripheral member 802, a second peripheral member 804 and panels 812 and 813. The cuff unit 800 also includes a fastener 854 that has a ribbed belt as well as a male fastener member that can engage with a socket provided by support panel 851, which is shown in more detail in FIGS. 8D and 8E.

The cuff unit 800 has a track defined by an upper track portion provided on the inner edge of the first peripheral member 802 and a lower track portion 808 provided on the inner edge of the second peripheral member 804. The lower and upper track portions may include connectors that are adaptable to receive corresponding connectors that may be provided on the first and second end portions of panels 812 and 813. The cuff unit 800 also includes a stimulation module, a battery module and two contact members.

It should be noted that the cuff unit 800 only uses two panels 812 and 813. Furthermore, the panels 812 and 813 have complementary shapes such that the panels 812 and 813 may releasably engage one another in an interlocking fashion. The panels 812 and 813 may be considered to have an L shape and are arranged such that the panel 813 is flipped vertically and flipped horizontally to face the panel 812. In other words, adjacent panels have an L shape and an L-shape rotated 180 degrees, respectively. This provides additional structural strength for the cuff unit 800. However, the panels 812 and 813 are adjustable so that they can be moved apart from one another such that there is a space or an air gap between them but they are still adjacent to one another and touching such that they support one another and provide additional structural strength for the cuff unit 800. An example of this spaced apart position for the panels 812 and 813 is shown in FIG. 8B.

Referring now to FIGS. 8C and 8D, shown therein is a view of the cuff unit 800 in an open configuration. The fastener 854 includes a pair of ribbed belt fasteners 860 and a pair of male fastener members 856. The cuff unit 800 also includes a support panel 850 along with a first support post 852a, a second support post 852b and a third support post 852c. The male fastener members 856 are engageable with sockets provided by the support panel 851. The ribbed belt fasteners 860 can function as self-locking fasteners so that the user 180 can entwine the ribbed belt fasteners 860 around the first support post 852a, the second support post 852b and the third support post 852c such that the fastening teeth 862 interlock (similar to what was shown in FIG. 6C and explained for cuff unit 700).

The cuff unit 800 also includes an alignment marker 848 that can be used to properly position the cuff unit 800 for use, such as by aligning the alignment marker 848 with a knee cap of the user 180. Alternative alignment markers can also be used with the cuff unit 800 such as an alignment notch 246 or any other suitable alignment indicators. The cuff unit 800 also includes an indicator light 832 and control buttons 830.

Referring now to FIG. 8E, shown therein is a rear exploded view of the cuff unit 800 with the panels slightly apart. The bottoms of the posts 872a, 872b and 872c of the support panel 850 engage corresponding apertures 870a, 870b, and 870c in the upper surface of the lower peripheral member 804. A similar physical arrangement applies for the tops of the posts 872a, 872b and 872c of the support panel 850 engaging corresponding apertures (not shown) in the lower surface of the top peripheral member 802.

The cuff unit 800 may also include spacer members 802a and 804a that fit within the upper and lower track portions respectively of the upper and lower peripheral members 802 and 804. The space members 802a and 804a may be used to maintain a certain spaced relationship between the control panel 813 and the support panel 850. The upper and lower peripheral members 802 and 804 may also include a rib (such as rib 804r for example), that is fixed in place to prevent the side of the control panel 813 that is opposite the spacer members 802a and 804a from moving. These structural features may be seen more clearly in FIG. 8E.

Referring now to FIG. 8F, shown therein is an exploded view of the panel 813 of the cuff unit 800 that houses two circuit boards and has an electrode. In this example, the panel 813 may be used as a control panel, the circuit board 880 includes control and communication circuitry and the circuit board 886 includes the stimulation module with electrical components for generating stimulation signals for the user 180 during use (wiring or other electrical connections are generally not shown). The control panel 813 includes a main housing 813h with spacers 813s (only one is labelled for simplicity) and channels (not shown), and a cover 813c with resilient protrusions 878p.

The control panel 813 also includes buttons 830a and 830b and a light element (not shown). In other embodiments, there may be more or fewer control buttons. The control buttons 830a and 830b and the light element protrude through apertures on a main wall 813w of the housing 813h when the control panel 813 is assembled.

The spacers 813s of the control panel 813 provide support for the circuit board 880 so that it does not touch the main wall 813w of the housing 813h in operation. The resilient protrusions 878p of the cover 813c form a snap fit or friction fit with the channels (not shown) of the main housing 813h when the cover 813c is mounted on the main housing 813h.

The control panel 813 also includes an aperture 884 to allow for an external hardware connection between the circuit board 880 and another electronic device. The connection may be a USB connection, for example. In this example embodiment, the aperture 884 is located at the side of the panel 813 that houses both the control circuitry and the stimulation module. Fasteners 880f, such as screws or rivets, may be to secure the circuit boards 880 and 886 to the main housing 813h of the control panel 813.

The control panel 813 also includes a channel 874c for receiving a conductive strip 836 to which electrode 838 is mounted. The channel 874c includes a small aperture to receive the conductive strip 836 and also allow the conductive strip 836 to make an electrical connection with the stimulation module on the circuit board 880.

Referring now to FIG. 8G, shown therein is an exploded view of panel 812 of the cuff unit 800 that houses batteries and includes an electrode. The panel 812 includes a main housing 812h and channels 812ch (only one of which are shown), and a cover 812c with resilient protrusions 876p. Battery cells 834 are mounted on wall 812w of the main housing 812h and then the resilient protrusions 876p of the cover 812c form a snap fit or friction fit with the channels 812ch when the cover 812c is mounted on the main housing 812h. The battery cells 834 may be of different sizes and shaped to complement the shape of the panel housing 812h as shown in FIG. 8G so as to efficiently and fully utilize the space within the panel housing 812h.

The cover 812c also includes a channel 874c for receiving a conductive strip 836 to which electrode 838 is mounted. The channel 874c includes a small aperture to receive the conductive strip 836 and also allow the conductive strip 836 to make an electrical connection with the stimulation module that is in the panel 813. Electrical wiring or other contacts are not shown but it should be understood that there are electrical wires or electrical traces that couple the batteries 834 with the stimulation module that is in the panel 813. Also, there are electrical wires or electrical traces that couple the conductive strip 836 and the electrode 838 with the stimulation module that is in the panel 813.

FIGS. 8E-8G also illustrate the relationship between the conductive member 836 of a contact member and the electrode 838 in accordance with an example embodiment. The conductive member 836 is provided as a piece of conductive material. The conductive member 836 couples the electrode 838 to the stimulation module such that the electrode 838 is operable to apply the stimulation signals generated by the stimulation module to the user 180.

The electrode 838 can be translated with respect to the panels 812 and 813 to properly align the electrode to apply the stimulation signals to nerve(s) of the user 180 that require stimulation. The conductive member 836 is provided with a sufficient size to ensure that regardless of the position of the electrode 838 it will remain in electrical communication with the stimulation module. Once the electrode 838 has been properly aligned, it can be secured in place using any suitable means such as an electrically conductive adhesive.

It should be noted that the various embodiments of the cuff units described according to the teachings herein share certain features. For example, these various cuff units are generally portable and provide electronic circuit integration within the cuff housing with no external electrical components other than electrodes. The size, weight and design of the various cuff units herein make the cuff units more convenient to use and to wear and by the use of panels that have air gaps between the may provide increased air flow to the user's leg where the cuff unit is being worn making the cuff unit more comfortable to wear. Also, since the electronics are integrated within the housing of the cuff unit, there may be protection from certain amounts of rain, certain amounts of fluid spills and certain amounts of user perspiration.

The various embodiments of the cuff units described in accordance with the teachings herein may also be more user-friendly and easier to operate and fit to a user given the use of at least one of adjustable panels, adjustable electrodes and adjustable buckles depending on the particular cuff embodiment. The adjustable panels and buckles allow the size of the cuff unit to be changed to accommodate users with different sized legs. Some cuff units described herein provide all three of these features while others provide a subset of these features.

Various example embodiments of a cuff unit that can be used with an FES system have been described herein by way of example only. Various modifications and variations may be made to these example embodiments without departing from the spirit and scope of the embodiments, which is limited only by the appended claims.

The invention claimed is:

1. An apparatus for a functional electrical stimulation (FES) system, the apparatus comprising:
    a flexible housing comprising a frame having a plurality of panels entirely contained within the housing, the housing being releasably mountable on a user, at least one of the panels being adjustably movable with respect to the frame;
    a battery module having one or more batteries, each battery module being contained within a first one or more of the panels;
    a stimulation module coupled to the battery module and contained within a second one or more of the panels, the stimulation module being operable to generate stimulation signals to be applied to the user;
    control circuitry disposed within the flexible housing and coupled to the battery module and the stimulation module to control the apparatus; and
    at least two contact members movably connected to the frame and in electrical contact with the stimulation module, the at least two contact members being operable to apply the stimulation signals to the user.

2. The apparatus of claim 1, wherein each contact member is associated with one of the panels and each contact member comprises:
    a conductive member disposed along a surface of the associated panel; and
    an electrode coupled to the conductive strip and mounted to the associated panel.

3. The apparatus of claim 2, wherein the electrode is translatable with respect to the panel to which it is mounted.

4. The apparatus of claim 1, wherein the frame comprises a set of horizontally extending peripheral members comprising
- a first peripheral member defining an upper periphery of the frame; and
- a second peripheral member substantially parallel to and spaced apart from the first peripheral member, the second peripheral member defining a lower periphery of the frame;

wherein each of the first and second peripheral members has a peripheral member width dimension defining a frame width for the frame.

5. The apparatus of claim 4, wherein each panel has a panel width and the frame width is at least equal to the panel width.

6. The apparatus of claim 4, wherein each panel extends in a substantially vertical direction between the first and second peripheral members.

7. The apparatus of claim 4, wherein the frame comprises:
- a track defined by an upper track portion provided on an edge of the first peripheral member and a lower track portion provided on a corresponding edge of the second peripheral member; and
- a first end of each panel is moveably engageable with the upper track portion of the first peripheral member and a second end of each panel is moveably engageable with the second track portion of the second peripheral member, the second end being opposite to the first end, and the first and second end portions of the panels include connectors that engage connector portions in the upper and lower track portions respectively.

8. The apparatus of claim 4, wherein the housing further comprises:
- a third peripheral member substantially parallel to the first peripheral member between the first and second peripheral members;
- a first set of panels of the plurality of panels movably positioned between the first peripheral member and the third peripheral member; and
- a second set of panels of the plurality of panels movably positioned between the second peripheral member and the third peripheral member.

9. The apparatus of claim 8, wherein each contact member is associated with one of the panels in the second set of panels.

10. The apparatus of claim 8, wherein the batteries are contained in one or more of the panels in the first set of panels.

11. The apparatus of claim 1, wherein at least one of the panels is initially movable with respect to the frame and subsequently fixed in place for later use by the user.

12. The apparatus of claim 1, wherein the panels have a complementary shape to engage one another in an interlocking fashion.

13. The apparatus of claim 12, wherein adjacent panels have an L shape and an L-shape rotated 180 degrees.

14. The apparatus of claim 1, wherein the panels are spaced apart along the frame and air gaps are provided between the panels.

15. The apparatus of claim 1, wherein a given panel comprises at least one battery and a circuit board to provide the stimulation module.

16. The apparatus of claim 1, wherein a given panel comprises at least one circuit board to provide the stimulation module and the control circuitry.

17. The apparatus of claim 16, wherein the given panel further comprises a given electrode.

18. The apparatus of claim 1, wherein one of the panels is a control panel comprising control circuitry and control buttons to allow a user to control the apparatus.

19. The apparatus of claim 18, wherein the control panel further comprises an indicator light for providing a visual indication of a status of the apparatus.

20. The apparatus of claim 1, wherein the frame is releasably securable around a leg of the user.

21. The apparatus of claim 1, wherein the apparatus further comprises a USB connector port coupled to at least one of the battery module and the stimulation module.

22. An apparatus for a functional electrical stimulation (FES) system, the apparatus comprising:
- a flexible housing comprising a frame that is releasably mountable on a user, the frame having:
  - a first end;
  - a second end opposite to the first end;
  - a first peripheral member extending from the first end to the second end defining a top side;
  - a second peripheral member extending from the first end to the second end substantially parallel to and spaced apart from the first peripheral member defining a bottom side; and
  - a plurality of panels coupled to the frame and extending between the first peripheral member and the second peripheral member, the plurality of panels being adjustable and spaced apart to define at least one area that is substantially devoid of material, at least one of the panels being initially movable with respect to the frame and subsequently fixed in place for later use by the user;
- a battery module disposed within the frame;
- a stimulation module disposed within the frame; and
- control circuitry coupled to the battery module and the stimulation module.

23. A cuff unit for a functional electrical stimulation (FES) system, the cuff unit comprising:
- a flexible housing comprising a frame that is releasably mountable on a user of the FES system; and
- a plurality of panels coupled to the frame, the plurality of panels being adjustable in location and at least one of the panels is configured to house a battery module, at least one of the panels is configured to house a stimulation module and at least one of the panels is configured to house control circuitry, and the panels have a complementary shape to engage one another in an interlocking fashion.

24. The cuff unit of claim 23, wherein at least some of the panels are adjustably spaced apart to define at least one area that is substantially devoid of material between adjacent panels.

25. The cuff unit of claim 23, wherein the frame comprises:
- a first end;
- a second end opposite to the first end;
- a first peripheral member extending from the first end to the second end defining a top side of the frame; and
- a second peripheral member extending from the first end to the second end substantially parallel to and spaced apart from the first peripheral member defining a bottom side of the frame, wherein the panels are arranged in a substantially vertical orientation between the first and second peripheral members.

* * * * *